United States Patent [19]

Mundy et al.

[11] Patent Number: 5,408,041
[45] Date of Patent: Apr. 18, 1995

[54] PROCESS OF PURIFYING ANTLER-DERIVED BONE GROWTH FACTORS

[75] Inventors: Gregory R. Mundy; Gloria E. Gutierrez; Ian R. Garrett, all of San Antonio, Tex.; Massimo Sabatini, Neuilly-sur-Seine, France; Elzbieta Izbicka, San Antonio, Tex.; Wilson Burgess, Gaithersburg, Va.; Gregg R. Crumley, Philadelphia; Clarence C. Morse, King of Prussia, both of Pa.; Timothy R. Arnett, San Antonio, Tex.

[73] Assignees: Rhone-Poulenc Rorer Pharmaceuticals Inc.; OsteoSA Inc., both of Collegeville, Pa.

[21] Appl. No.: 180,572

[22] Filed: Jan. 13, 1994

Related U.S. Application Data

[63] Continuation of Ser. No. 855,415, Mar. 18, 1992, abandoned.

[51] Int. Cl.⁶ .......................... C07K 1/00; C07K 3/00; C07K 15/00
[52] U.S. Cl. .................................. 530/413; 530/412; 530/414; 530/416; 530/417; 530/422
[58] Field of Search ............... 530/412, 413, 414, 416, 530/417, 422

[56] References Cited

U.S. PATENT DOCUMENTS 4,795,804 8/1985 Urist et al. .
5,106,626 10/1989 Parsons et al. .
5,108,753 9/1990 Kuberasampath et al. .

OTHER PUBLICATIONS

Sempere, A. J. et al., *Endocrinology*, 125(5):2312–2319, 1989.
Bubenik, G. A. et al., *Calcif. Tissue Int.*, 41:38–43, 1987.
J. Biol. Chem. 261:12665–12674, 1986, Hauschka, Mavrakos, Iafrati, Doleman, Klagsbrun.
J. Biol. Chem. 262:1946–1949, 1987. Seyedin, Segarini, Rosen, Thompson, Bentz, Graycar, Cartilage-inducing Factor-B is a Unique Protein Functionally Related to TFG-beta.
J. Biol. Chem. 264:20805–20810, 1989 Bentz, Nathan, Rosen, Armstrong, Thompson et al. Purification and Characterization of a Unique Osteoinductive Factor from Bovine Bone.

*Primary Examiner*—Garnette D. Draper
*Assistant Examiner*—Marianne Porta Allen
*Attorney, Agent, or Firm*—Rosanne Goodman; Martin F. Savitzky

[57] ABSTRACT

The present invention relates to the development of bone growth factors as therapeutics for the prevention and treatment of pathological conditions involving bone tissue. The present invention provides biologically active proteinaceous factors comprising polypeptides containing the amino acid sequence M-A-G-L-G-D-E-F-G-D, [SEQ ID NO: 1], (X) F E T L F G A/V E D V I/D A L Q F V C G D, [SEQ ID NO: 2], or A-Y-I-P-I-E-T-L-E-G-I/G-E-L-V-D/Q-T-G/L-Q-F, [SEQ ID NO: 3], or biologically active fragments or sequence analogues thereof. Among the biological properties of the proteinaceous materials of the present invention is the capability to promote the growth and/or differentiation of osteoblastic cells.

3 Claims, 35 Drawing Sheets

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Met Ala Gly Leu Gly Asp Glu Phe Gly Asp
    1               5                      10

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        -( A ) NAME/KEY: Modified-site
        ( B ) LOCATION: 12
        ( D ) OTHER INFORMATION: /note="either I or D"

( i x ) FEATURE:
        ( A ) NAME/KEY: Modified-site
        ( B ) LOCATION: 8
        ( D ) OTHER INFORMATION: /note="either A or V"

( x i ) SEQUENCE DESCRIPTION: SEQ ID NO:2:

```
Xaa  Phe  Glu  Thr  Leu  Phe  Gly  Ala  Glu  Asp  Val  Ile  Ala  Leu  Gln  Phe
 1                  5                        10                       15

Val  Cys  Gly  Asp
              20
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 11
        ( D ) OTHER INFORMATION: /note="either I or G"

( i x ) FEATURE:
        ( A ) NAME/KEY: Modified-site
        ( B ) LOCATION: 15
        ( D ) OTHER INFORMATION: /note="either D or Q"

( i x ) FEATURE:
        ( A ) NAME/KEY: Modified-site
        ( B ) LOCATION: 17
        ( D ) OTHER INFORMATION: /note="either G or L"

( x i ) SEQUENCE DESCRIPTION: SEQ ID NO:3:

```
Ala  Tyr  Ile  Pro  Ile  Glu  Thr  Leu  Glu  Gly  Ile  Glu  Leu  Val  Asp  Thr
 1                  5                        10                       15

Gly  Gln  Phe
```

( 2 ) INFORMATION FOR SEQ ID NO:4:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Ala  Tyr  Arg  Pro  Ser  Glu  Thr  Leu  Cys  Gly  Gly  Glu  Leu  Val  Asp  Thr
 1                  5                        10                       15

Leu  Gln  Phe
```

( 2 ) INFORMATION FOR SEQ ID NO:5:

( i ) SEQUENCE CHARACTERISTICS:

(A) LENGTH: 70 amino acids
(B) TYPE: amino acid
(D) TOPOLOGY: linear (ii) MOLECULE TYPE: peptide (xi) SEQUENCE DESCRIPTION: SEQ ID NO:5:

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Lys Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

(2) INFORMATION FOR SEQ ID NO:6:

(i) SEQUENCE CHARACTERISTICS:
(A) LENGTH: 28 amino acids
(B) TYPE: amino acid
(D) TOPOLOGY: linear (ii) MOLECULE TYPE: peptide (xi) SEQUENCE DESCRIPTION: SEQ ID NO:6:

```
Ala Tyr Arg Pro Ser Glu Thr Leu Xaa Gly Gly Glu Leu Val Asp Thr
1               5                   10                  15

Leu Gln Phe Val Xaa Gly Asp Xaa Xaa Phe Tyr Phe
                20                  25
```

(2) INFORMATION FOR SEQ ID NO:7:

(i) SEQUENCE CHARACTERISTICS:
(A) LENGTH: 71 amino acids
(B) TYPE: amino acid
(D) TOPOLOGY: linear (ii) MOLECULE TYPE: peptide (xi) SEQUENCE DESCRIPTION: SEQ ID NO:7:

```
Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ser
                20                  25                  30

Ser Arg Ile Asn Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
    50                  55                  60

Lys Ser Glu Arg Asp Val Ser
65                  70
```

(2) INFORMATION FOR SEQ ID NO:8:

(i) SEQUENCE CHARACTERISTICS:
(A) LENGTH: 67 amino acids
(B) TYPE: amino acid
(D) TOPOLOGY: linear (ii) MOLECULE TYPE: peptide (xi) SEQUENCE DESCRIPTION: SEQ ID NO:8:

```
Ala Tyr Arg Pro Ser Glu Thr Leu Cys Gly Gly Glu Leu Val Asp Thr
1               5                   10                  15
```

```
        Leu Gln Phe Val Cys Gly Asp Arg Gly Phe Tyr Phe Ser Arg Pro Ala
                    20              25              30

Ser Arg Val Ser Arg Arg Ser Ala Gly Ile Val Glu Glu Cys Cys Phe
                    35              40              45

Arg Ser Cys Asp Leu Ala Leu Leu Glu Thr Tyr Cys Ala Thr Pro Ala
                    50              55              60

Lys Ser Glu
        65
```

(2) INFORMATION FOR SEQ ID NO:9:

(i) SEQUENCE CHARACTERISTICS:
        (A) LENGTH: 67 amino acids
        (B) TYPE: amino acid
        (D) TOPOLOGY: linear (ii) MOLECULE TYPE: peptide (xi) SEQUENCE DESCRIPTION: SEQ ID NO:9:

```
        Ala Tyr Gly Pro Gly Glu Thr Leu Cys Gly Gly Glu Leu Val Asp Thr
        1               5               10              15

Leu Gln Phe Val Cys Ser Asp Arg Gly Phe Tyr Phe Ser Arg Pro Ser
                    20              25              30

Ser Arg Ala Asn Arg Arg Ser Ala Gly Ile Val Glu Glu Cys Cys Phe
                    35              40              45

Arg Ser Cys Asp Leu Ala Leu Leu Glu Thr Tyr Cys Ala Thr Pro Ala
                    50              55              60

Lys Ser Glu
        65
```

(2) INFORMATION FOR SEQ ID NO:10:

(i) SEQUENCE CHARACTERISTICS:
        (A) LENGTH: 67 amino acids
        (B) TYPE: amino acid
        (D) TOPOLOGY: linear (ii) MOLECULE TYPE: peptide (xi) SEQUENCE DESCRIPTION: SEQ ID NO:10:

```
        Ala Tyr Arg Pro Ser Glu Thr Leu Cys Gly Gly Glu Leu Val Asp Thr
        1               5               10              15

Leu Gln Phe Val Cys Ser Asp Arg Gly Phe Tyr Phe Ser Arg Pro Ser
                    20              25              30

Ser Arg Ala Asn Arg Arg Ser Ala Gly Ile Val Glu Glu Cys Cys Phe
                    35              40              45

Arg Ser Cys Asp Leu Ala Leu Leu Glu Thr Tyr Cys Ala Thr Pro Ala
                    50              55              60

Lys Ser Glu
        65
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 10..12
        (D) OTHER INFORMATION: /note="CTN or TTR"

( x i ) SEQUENCE DESCRIPTION: SEQ ID NO:11:

ATGGCNGGNC TNGGNGAYGA RTTYGGNGAY 30

( 2 ) INFORMATION FOR SEQ ID NO:12:

( i ) SEQUENCE CHARACTERISTICS:
        ( A ) LENGTH: 60 base pairs
        ( B ) TYPE: nucleic acid
        ( C ) STRANDEDNESS: single
       -( D ) TOPOLOGY: linear ( i i ) MOLECULE TYPE: cDNA ( i x ) FEATURE:
        ( A ) NAME/KEY: misc_feature
        ( B ) LOCATION: 13..15
        ( D ) OTHER INFORMATION: /note="CTN or TTR"

( i x ) FEATURE:
        ( A ) NAME/KEY: misc_feature
        ( B ) LOCATION: 34..36
        ( D ) OTHER INFORMATION: /note="GAY or ATH"

( i x ) FEATURE:
        ( A ) NAME/KEY: misc_feature
        ( B ) LOCATION: 40..42
        ( D ) OTHER INFORMATION: /note="CTN or TTR"

( x i ) SEQUENCE DESCRIPTION: SEQ ID NO:12:

NNNTTYGARA CNCTNTTYGG NGYNGARGAY GTNGAYGCNC TNCARTTYGT NTGYGGNGAY 60

( 2 ) INFORMATION FOR SEQ ID NO:13:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 22..24
        ( D ) OTHER INFORMATION: /note="CTN or TTR"

( i x ) FEATURE:
        ( A ) NAME/KEY: misc_feature
        ( B ) LOCATION: 31..33
        ( D ) OTHER INFORMATION: /note="ATH or GGN"

( i x ) FEATURE:
        ( A ) NAME/KEY: misc_feature
        ( B ) LOCATION: 37..39
        ( D ) OTHER INFORMATION: /note="CTN or TTR"

( i x ) FEATURE:
        ( A ) NAME/KEY: misc_feature
        ( B ) LOCATION: 43..45
        ( D ) OTHER INFORMATION: /note="GAY OR CAR"

( i x ) FEATURE:
        ( A ) NAME/KEY: misc_feature
        ( B ) LOCATION: 49..51
        ( D ) OTHER INFORMATION: /note="GGN or CTN or TTR"

( x i ) SEQUENCE DESCRIPTION: SEQ ID NO:13:

GCNTAYATHC CNATHGARAC NCTNGARGGN ATHGARCTNG TNGAYACNGG NCARTTY 57

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single (D) TOPOLOGY: linear (ii) MOLECULE TYPE: cDNA (xi) SEQUENCE DESCRIPTION: SEQ ID NO:14:

CTGGATCCAG AGACCCTCTG CGGGGC  26

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CTGCGGAATT CAGCACTCAT CCACGAT  27

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

ATGGGGATCC CAGTGGGGAA GTCGAT  26

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CTCTTCAGTT CGTCTGTGGA GACAGCGGCT T  31

(2) INFORMATION FOR SEQ ID NO:18:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:18:

Ala Tyr Arg Pro Ser Glu Thr Leu Cys Gly Gly Glu Leu Val Asp Thr
1               5                  10                  15

Leu Gln Phe Val Cys Gly Asp Arg Gly Phe Tyr Phe Ser Arg Pro Ser
            20                  25                  30

Ser (2) INFORMATION FOR SEQ ID NO:19:

(i) SEQUENCE CHARACTERISTICS:
        (A) LENGTH: 99 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:19:

GCTTACCGCC CCAGTGAGAC CTTGTGCGGC GGGGAGCTGG TGGACACCCT CCAGTTTGTC    60

TGTGGGGACC GCGGCTTCTA CTTCAGCCGA CCATCCAGC    99

(2) INFORMATION FOR SEQ ID NO:20:

(i) SEQUENCE CHARACTERISTICS:
        -(A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GCTTACCGCC CCAGTGAGAC CCTGTGCGGC GGGGAGCTGG TGGACACCCT CCAGTTCGTC    60

TGTGGGGACC GCGGCTTCTA CTTCAGCAGG CCCGCAAGC    99

(2) INFORMATION FOR SEQ ID NO:21:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:21:

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20              25                  30

Ser (2) INFORMATION FOR SEQ ID NO:22:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /note="A or V"

(ix) FEATURE:
        (A) NAME/KEY: Modified-site
        (B) LOCATION: 12
        (D) OTHER INFORMATION: /note="either I or D"

(xi) SEQUENCE DESCRIPTION: SEQ ID NO:22:

Xaa Phe Glu Thr Leu Phe Gly Ala Glu Asp Val Ile Ala Leu
1               5                   10

PROCESS OF PURIFYING ANTLER-DERIVED BONE GROWTH FACTORS

This is a continuation of application Ser. No. 07/855,415 filed on Mar. 18, 1992, now abandoned.

BACKGROUND OF THE INVENTION

Field of the Invention

The present invention relates to the development of bone growth factors as therapeutics for the prevention and treatment of pathological conditions involving bone tissue, for example osteoporosis, Paget's disease, osteopetrosis, fracture repair, periodontal disease and healing of bone defects. The factors of the present invention may also be useful for promoting wound healing and in anti-tumor treatments.

Living bone tissue is continuously being replenished by the process of resorption and deposition of calcium minerals. This process, termed the resorption-formation cycle, is facilitated primarily by two cell types, the osteoblasts and the osteoclasts. The osteoclast is a multinucleated cell (a cell with more than one nucleus) and is the only cell in the body known to have the capacity to degrade (or resorb) bone. This resorption activity is accomplished by the osteoclast forming pits (resorption lacunae) in bone tissue, and, in fact, osteoclast activity in cell culture is measured by their capacity to form these pits on slices of mineralized tissue such as bone or sperm whale dentine. The osteoclast is derived from a hematopoietic precursor which it shares with the formed elements of the blood (Mundy & Roodman (1987) Osteoclast ontogeny and function. In *Bone and Mineral Research V*: 209–280. (ed. Peck) Elsevier). The precursor for the osteoclast is a mononuclear cell (cell with a single nucleus) which is found in the bone marrow and which forms the mature and unique multinucleated osteoclast after undergoing replication and differentiation by means of cell fusion. The mature osteoclast is distinguished from other multinucleated cells by the presence of the enzyme tartrate-resistant acid phosphatase (TRAP) which is often used as an osteoclast cell marker.

Among the pathological conditions associated with an abnormal osteoclast development or function are conditions wherein increased bone resorption results in the development of fragile and/or brittle bone structure, such as osteoporosis, or increased bone formation results in the development of excess bone mass, such as osteopetrosis. It is believed that the development of excess or deficient populations of osteoclasts or osteoblasts may result from a corresponding lack or excess of specific protein factors called cytokines.

REPORTED DEVELOPMENTS

Cytokines have been identified by their biological characteristics and their unique amino acid sequences and each cytokine presents a unique spectrum of characteristics utilized to distinguish it from other cytokines. In general, the cytokines stimulate the growth and/or differentiation of specific types of cells, and some of them can also target cancerous cells for destruction. Examples of such cytokines include granulocyte-colony-stimulating factor (G-CSF), granulocyte-macrophage CSF(GM-CSF), macrophage CSF (M-CSF), interleukin-1 beta, interleukin-3, interleukin-6, interferon-gamma, tumor necrosis factor, lymphotoxin, leukemia inhibitory factor, and transforming growth factor-alpha.

Many of the known cytokines stimulate or inhibit blood cells. Several growth regulatory cytokines, such as M-CSF, transforming growth factor alpha, interleukin-1 and tumor necrosis factor, have been shown to stimulate marrow mononuclear cell proliferation. Although cytokines such as interleukin-1 (IL-1), tumor necrosis factor (TNF) and interleukin-6 (IL-6) may influence osteoclast formation and differentiation (Mundy (1990) Trends Endo. Metab. 1:307–311), these factors are not specific osteoclast growth regulatory factors.

Although there is much information available on the factors which influence the breakdown and resorption of bone, information is more limited on factors which can actually stimulate the formation of new bone. Bone itself has been found to contain factors which have the capacity for stimulating the growth and/or differentiation of bone cells. Thus, extracts of bone tissue contain not only structural proteins which are responsible for maintaining the structural integrity of bone, but also biologically active bone growth factors which stimulate bone cells to proliferate. Among the known factors which stimulate proliferation of bone cells are transforming growth factor $\beta$, the heparin binding growth factors (acidic and basic fibroblast growth factor), the insulin-like growth factors (insulin-like growth factor 1 and insulin-like growth factor II) and a recently described family of proteins called bone morphogenetic proteins. These factors also cause proliferation of non-bone cell types.

The growth of deer antler represents a special type of bone formation known as endochondral bone formation. The deer antler represents the most rapidly growing form of bone in mammalian tissues. This growth is similar to that which occurs in long bone shafts of vertebrates during adolescence and to bone growth which is responsible for the repair of bone injuries following fracture. However, the factors responsible for controlling antler growth like those controlling bone growth in other vertebrates have not been identified or characterized.

The present invention relates to the isolation of biologically active polypeptides from deer antler tissue and characterization of these polypeptides. The biological activity of these peptides includes stimulation of cellular proliferation and/or differentiation.

SUMMARY OF THE INVENTION

The present invention provides biologically active proteinaceous factors comprising polypeptides containing the amino acid sequence M-A-G-L-G-D-E-F-G-D [SEQ ID NO: 1], (X) F E T L F G A/V E D V I/D A L Q F V C G D [SEQ ID NO: 2], or A-Y-I-P-I-E-T-L-E-G-I/G-E-L-V-D/Q-T-G/L-Q-F [SEQ ID NO: 3] or biologically active fragments or sequence analogues thereof. Among the biological properties of the proteinaceous materials of the present invention is the capability to promote the growth and/or differentiation of osteoblastic cells.

The present invention provides proteinacious factors which are purified from antler tissue utilizing the isolation techniques described hereinbelow and which are useful in the treatment of bone diseases characterized by abnormal osteoblast function such as osteoporosis. Antibodies which bind to the proteinaceous factors of this invention are useful for (1) the treatment of diseases where there is over-growth of bone such as osteopetrosis, and (2) as reagents in assays, which measure quantitatively and/or qualitatively the presence and amount of said factors, and which assays are useful in the clinical diagnosis, assessment and monitoring treatment efficacy of those diseases in which abnormal production of said factors occurs.

Other and further objects, features and advantages will be apparent from the following description of the preferred embodiments of the invention given for the purpose of disclosure when taken in conjunction with the following drawings.

DESCRIPTION OF THE PREFERRED EMBODIMENTS

Figure 1A:
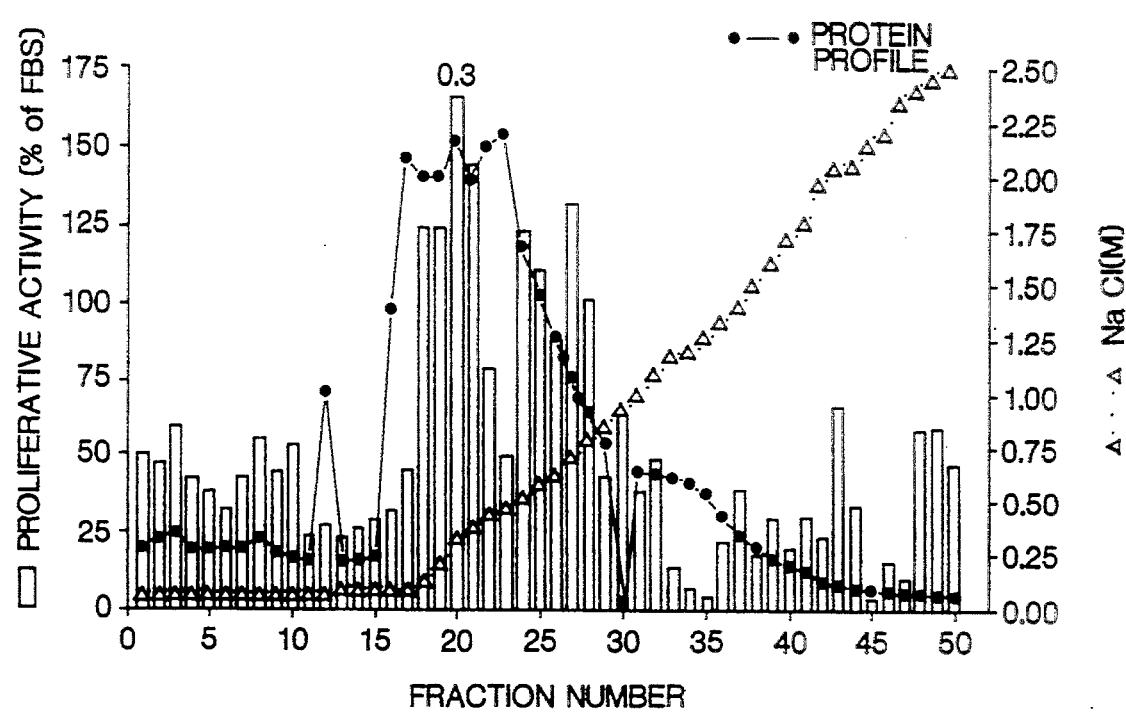
FIGS. 1a and 1b describe the heparin Sepharose chromatography elution profiles of OT-1 and proliferative activity of EDTA-extracted antler preparations on MG-63 cells.

The present invention also provides biologically active proteinaceous bone growth factors in substantially homogeneous form by means of biochemical purification from antler tissue. The invention encompasses these naturally occurring bone growth factors in partially purified as well as substantially homogeneous form, as well as synthetically produced bone growth factors, biologically active fragments thereof, and pharmaceutically acceptable salts and derivatives thereof.

"Substantially purified" is used herein as "substantially homogeneous" which is defined as a proteinaceous material which is substantially free of compounds normally associated with it in its natural state (e.g., other proteins or peptides, carbohydrates, lipids). Most preferably, it means a polypeptide which may be glycosylated or non-glycosylated and which is characterizable by a single molecular weight and/or multiple set of molecular weights, chromatographic response and elution profiles, amino acid composition and sequence and biological activity. "Substantially purified" is not meant to exclude artificial or synthetic mixtures with other compounds. The term is also not meant to exclude the presence of impurities which do not interfere with biological activity, and which may be present, for example, due to incomplete purification or compounding with a pharmaceutically acceptable preparation.

The term "biologically active polypeptide" means naturally occurring polypeptide per se, as well as biologically active analogues thereof, including synthetically produced polypeptides and analogues thereof, as well as natural and pharmaceutically acceptable salts and pharmaceutically acceptable derivatives thereof.

The term biologically active polypeptide also encompasses biologically active fragments thereof, as well as biologically active sequence analogues thereof. Different forms may exist in nature. These variations may be characterized by differences in the nucleotide sequence of the structural gene coding for proteins of identical biological function.

The term "biologically active sequence analogue" includes non-naturally occurring analogues having single or multiple amino acid substitutions, deletions, additions, or replacements. All such allelic variations, modifications, and analogues resulting in derivatives which retain one or more of the native biologically active properties are included within the scope of this invention.

As used herein the term "salts" refers to both salts of carboxy groups of the polypeptide or protein chain and to acid addition salts of amino groups of the poly-peptide chain. Salts of the carboxy group may be formed with either inorganic or organic bases by means known in the art per se. Inorganic salts include, for example, sodium, calcium, ammonium, ferric or zinc salts, and the like. Salts with organic bases include those formed, for example, with amines such as triethanolamine, arginine, lysine, piperidine, caffeine, procaine and the like. Acid addition salts include, for example, salts with mineral acids such as, for example, hydrochloric acid or sulfuric acid, and salts with organic acids such as, for example, acetic acid or oxalic acid.

Derivatives may also be prepared from the functional groups which occur at side chains on the residues of the N- or C-terminal groups, by means known in the art, and are included in the invention as long as they remain diagnostically or therapeutically acceptable.

Both the salts and the derivatives encompassed by the invention are those which are therapeutically or diagnostically acceptable, i.e., those which do not eliminate the biologic or immunogenic activity. Therapeutically useful salts and derivatives are further non-toxic to the human or other animal patient in the appropriate dosage utilized in treatment.

The term "specific activity" refers to the activity in assays described in this application and other assays known in the art that measure proliferative activity of osteoblast and osteoblast-like cells. This term is related to the amount of biologically active protein by weight in a sample and more precisely understood to be a measure of purity of active protein/total sample protein calculated without considering the presence of intentionally added protein materials such as albumin. The measurement of one of the biological activities of the proteinaceous factors of the present invention is described in the assay procedure of Example 1.

The biologically active proteinaceous factors of the present invention (hereinafter also referred to as "OTs" or "antlerins") OT-1,2, and 3 were isolated from extracts of deer antler tissue and the biologically active proteinaceous factor OT-4 was isolated from conditioned medium in which deer antler cells were cultured. OT-2 (or Antlerin-2) and OT-4 (or Antlerin-4), have been characterized as having molecular weights of about 6 kd to about 7 kd. In addition, the deer forms of the growth factor IGF-I and IGF-II have been isolated from antler tissue and from deer serum.

Each OT has been purified to homogeneity. OT-1, OT-2 and OT-3 are characterized by having molecular weights of less than 50,000 daltons and have been partially purified and purified in homogeneous form. OT-4 is characterized by having a molecular weight of from about 5000 daltons to about 15000 daltons.

The OTs are distinct from known bone growth factors which have been shown to promote proliferation of human bone cells. The partial amino acid sequences of the polypeptides of three of these proteinaceous factors have been determined and are identified above and in further detail hereinbelow. Although the amino acid sequence of two of these polypeptides shows partial homology to insulin-like growth factor 1 (IGF-I) of human, bovine and rodent species, these proteins are distinct from IGF-I and other known bone growth factors.

The N-terminal sequence analysis of OT-1, OT-2, and OT-4 is provided herein. Purification of OT-1, OT-2 and OT-3 is achieved by a affinity chromatography, gel permeation chromatography and reverse phase chromatography. The affinity chromatography matrices comprise heparin Sepharose matrices, binding proteins coupled to matrices and specific antibodies coupled to solid matrices. The gel permeation matrices are selected from Sephacryl S-100 and SP Sephadex C50. High pressure liquid chromatography (HPLC) is performed using $C_4$, $C_6$, $C_8$ and $C_{18}$ HPLC resins.

The isolation of purified OT-1 is achieved by the sequential use of EDTA extraction of deer antler tissue, affinity chromatography on heparin Sepharose resin, gel permeation chromatography on Sephacryl S-100 resin and HPLC chromatography sequentially on $C_{18}$ and $C_8$ resins.

The isolation of purified OT-2 is achieved by the sequential use of EDTA extraction of deer antler tissue, affinity chromatography on heparin Sepharose resin, gel permeation chromatography on Sephacryl S-100 resin and HPLC on $C_{18}$, $C_4$, and $C_8$ resins.

The isolation of purified OT-3 is achieved similarly by affinity chromatography on heparin Sepharose, gel permeation chromatography on Sephacryl S-100 resin and HPLC on $C_{18}$ and $C_4$ resins.

The isolation of purified OT-4 is achieved by the sequential use of heparin Sepharose chromatography, Sephacryl S-100 chromatography, SP Sephadex C50 chromatography, IGF-BP3 affinity chromatography and C4 high performance liquid chromatography.

Under suitable circumstances, chromatographic procedures may be carried out, preferably in a narrow bore column containing a fine particle resin under increased pressure to enhance the effectiveness of separation, i.e., by high pressure liquid chromatography.

Concentration and salt removal are commonly used precursors to certain chromatographic or separation techniques employed in the invention.

Salt removal is generally necessary if ion exchange or other techniques which depend on total ionic strength are employed. Salt removal may be performed by, for example, dialysis or gel filtration or by control pore glass (CPG) chromatography.

A number of gel filtration and concentration techniques are also used. Certain commercially available materials are especially useful. Sephacryl, Sephadex, and Bio-Gel are examples of gel filtration media commonly used to isolate and purify proteins and characterize their properties.

Detectably labelling of homogeneous OT and the monoclonal antibodies thereto of the present invention is performed with a radiolabel, an enzyme label, or a fluorescent label. Preferably, the purified OTs are labelled with $^{125}I$ using the Bolton/Hunter reagent which involves succinylation of free N-terminal amino acids and lysine. See, for example, Chard, *An Introduction To Radioimmunoassay And Related Techniques,* North-Holland Publishing Co., Amsterdam-NY-Oxford (1978), *The Enzyme-Linked Immunoadsorbent Assay (ELISA)* by Voller, A., et al., Dynatech Europe Borough House, Rue du Pre, Guernsey, Great Britain, and *Radioiodination* Techniques Review 18, Amersham Corporation, by A. E. Bolton, all herein incorporated by reference.

Another aspect of the present invention relates to monoclonal and polyclonal antibodies to OTs, their fragments and/or their antigenic epitopes, and their therapeutic, diagnostic assay, and treatment monitoring assay uses. The anti-OT antibodies are useful in the diagnosis and monitoring of diseases where osteoblast function is altered, such as osteoporosis. A further aspect of the present invention relates to the antibody antagonists to OT which are capable of neutralizing OT biological activity, and the therapeutical use thereof. Antibodies against one of more of the proteinaceous factors of the present invention can be utilized to block the binding of ligands thereto and to target drugs or other agents (such as labels) to the cells expressing these factors.

Anti-OT monoclonal antibodies may be prepared using the method of Mishell, B. B., et al., *Selected Methods In Cellular Immunology,* (W. H. Freeman, ed.) San Francisco (1980), herein incorporated by reference.

The invention also encompasses compositions comprising OT, such as pharmaceutical and diagnostic compositions, and methods of using these factors in treatment and diagnosis of bone proliferative disorders. Several of the biologically active proteinaceous factors of the present invention, such as the OT factors described herein, stimulate the growth of human cells with the osteoblast phenotype. In one embodiment, the present invention provides a proteinaceous growth factor which stimulates proliferation of human C433 stromal cells and human MG-63 osteosarcoma cells, and which therefore is believed to be useful in the treatment of human and animal disorders characterized by an abnormally reduced level of osteoblastic cell proliferation.

Administration of the proteinaceous factors of the present invention may be by parenteral, intravenous, intramuscular, subcutaneous, rectal or any other suitable means. The dosage administered may be dependent upon the age, weight, kind of concurrent treatment, if any, and nature of the bone pathology being treated.

The biologically active proteinaceous factor of the present invention useful in the therapeutic method of the present invention may be employed in such forms as liquid solutions, suspensions, elixirs, or sterile liquid forms such as solutions or suspensions. Suitable carriers include diluents or fillers, sterile aqueous media and various non-toxic organic solvents. The compositions may be formulated in the form of powders, aqueous suspensions, or solutions, injectable solutions, elixirs, syrups and the like and may contain one or more stabilization agents such as human serum albumin, sugar or amino acid, antibacterial, and preserving agents in order to provide a pharmaceutically acceptable preparation. Any inert carrier is preferably used, such as saline, or phosphate-buffered saline, or any such carrier in which the factors used in the method of the present invention have suitable solubility properties for use in the method of the present invention.

The particular carrier and the ratio of active compound to carrier are determined by the solubility and chemical properties of the proteinaceous factors, the particular mode of administration and standard pharmaceutical practice. For parental administration, solutions or suspensions of these factors in aqueous alcoholic media or in sesame or peanut oil or aqueous solutions of the soluble pharmaceutically acceptable salts can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of about 0.1 mg/kg to about 500 mg/kg, preferably about 1 mg/kg to about 250 mg/kg, and most preferably about 5 mg/kg to about 100 mg/kg of body weight in injectable form; such may, of course, be given in divided doses. With other forms of administration equivalent or adjusted doses will be administered depending on the route of administration.

The following examples describe the isolation, purification and measurement of biological activity of the proteinaceous factors and antibodies of the present invention and are not intended to be limiting unless so expressly stated.

EXAMPLE 1

Assay for OT Biological Activity

The proliferative effects of OT on MG-63 human osteosarcoma cells and C433 human stromal cells is assessed by measuring the incorporation of tritiated thymidine into cellular DNA.

MG-63 human osteosarcoma cells, obtained from the American Type Culture Collection (Rockville, Md.), are cultured in Eagle's minimum essential medium (EMEM) supplemented with 10% fetal bovine serum (FBS). MC-3T3EI mouse osteoblasts, provided by Dr. T. Suda (Showa University, Tokyo), are cultured in alpha modification of Eagle's medium ($\alpha$MEM) supplemented with 10% FBS. C433 cells, a stromal cell line derived from a human giant cell tumor of bone, are cultured in Iscove's modified Dulbecco's medium (IMDM) supplemented with 10% FBS. All cultures are maintained at 37° C, in a humidified atmosphere of 5% $CO_2$ in air.

C433 cells are seeded at $2 \times 10^4$ cells/50 $\mu$l/well in 96 well plates in serum free IMDM containing 0.1% BSA.

Fifty μl/well of a sample of OT in DMEM/F12 50/50 (v/v) medium containing 0.1% BSA is added to each test wells. MG-63 and MC3T3 are seeded at $5\times10^3$ cells/100 μl/well in 96 well plates in 10% FBS EMEM or αMEM respectively. After incubation for approximately 18–24 hours, the cells are washed with 200 μl/well of phosphate buffered saline (PBS), re-fed with 50 μl/well of serum free 0.1% BSA in EMEM or αMEM and 50 μl/well of a sample of OT diluted in 0.1% BSA in DMEM/F12 is added. Baseline controls (50 μl/well of 0.1% BSA in DMEM/F12 50/50) as well as positive controls (50 μl/well of 20% FBS in DMEM/F12 50/50) are run in each plate in parallel with the test sample. About 44 hours after the addition of the sample and controls, the cells are pulsed with 1 μCi/well of [methyl $^3$H] thymidine for 4 hours. After 4 hours, the cells are collected and rinsed on filter paper discs using a PHD cell harvester (Cambridge Technology, Watertown, Mass.). The radioactivity retained by the filters is measured as cpm using a liquid scintillation counter (Beckman, Fullerton, Calif.).

The proliferative activity of each sample (run in duplicate) is expressed as percentage of the stimulation of incorporation of $^3$H thymidine caused by the positive control, by using the formula:

$$\frac{\text{cpm sample} - \text{cpm baseline control}}{\text{cpm positive control} - \text{cpm baseline control}} \times 100$$

The known bone-derived growth factors (TGFβ, PDGF, acidic and basic FGF, IGF-I, IGF-II) stimulate thymidine incorporation in MG-63 cells. IGF-I and IGF-II have also been reported to stimulate thymidine incorporation in C433 cells. OT-2 and OT-4, the isolation and purification of which are described hereinbelow, stimulate C433 cell proliferation.

EXAMPLE 2

Isolation of OT-1 from Deer Antler Tissue 1.5 antlers from male red deer are obtained during the growing season and immediately frozen in dry ice. The fur is removed with a scalpel. The velvet (Zone A) is separated from the hard tissue. The hard tissue (Zone B) is cut with a saw into smaller pieces. The tissue is crushed inside a steel cylinder using a hammer, and then pulverized with a coffee grinder.

48.8 g of hard tissue are extracted (1:2.5 w/v) by stirring at 4° C. for 72 hours in 125 ml of extraction buffer containing 0.5 M EDTA, 20 mM Tris, 25 mM benzamidine, 1 μg/ml leupeptin, 1 mM PMSF (dissolved in 100% isopropanol), adjusted to a final pH of 7.0. After 72 hours, the extract is centrifuged at 6000 rpm for 20 min at 4° C. The supernatant is removed and frozen at −70° C.

A second extraction of the pellet is performed by adding 250 ml of fresh extraction buffer to the pellet and stirring the mixture at 4° C. for another 24 hours. After this period, the extract is centrifuged at 6000 rpm for 20 min at 4° C., supernatants from the first and second extractions are combined and centrifuged at high speed at 15,000 g for 1 hr at 4° C.

The supernatant is removed, and dialyzed against 50 mM ammonium bicarbonate, lypholized and reconstituted in 200 ml 10 mM Tris, 0.1M NaCl, pH 7.0. Protein concentration is determined by the absorbance at 280 and 260 mm.

Figure 1B:
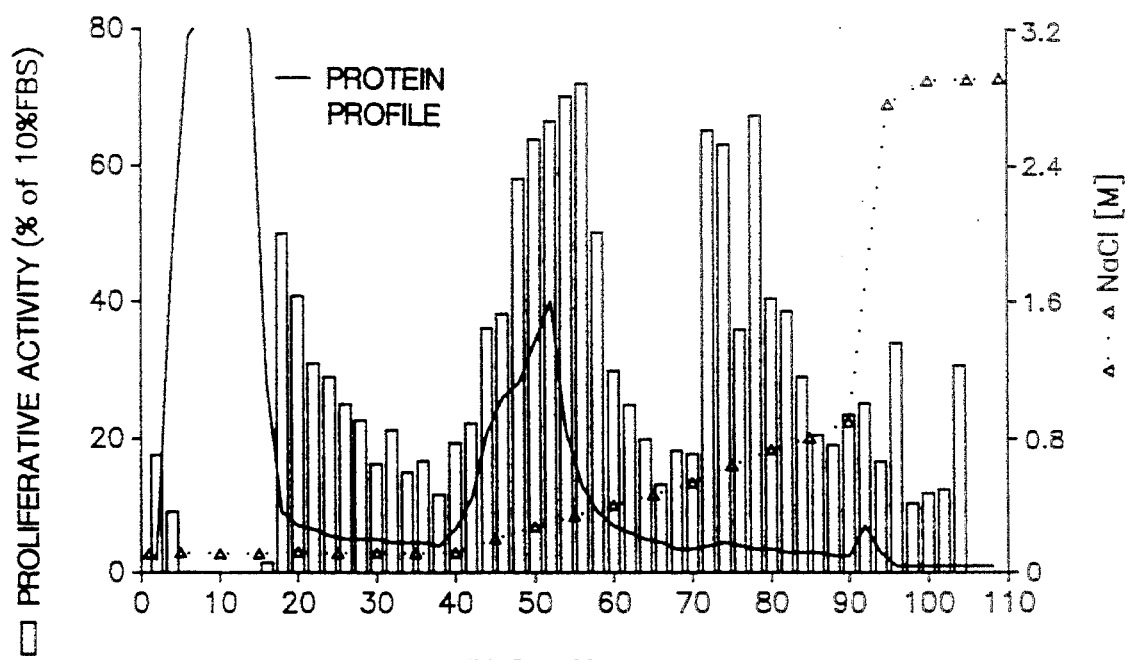
Figure 2:
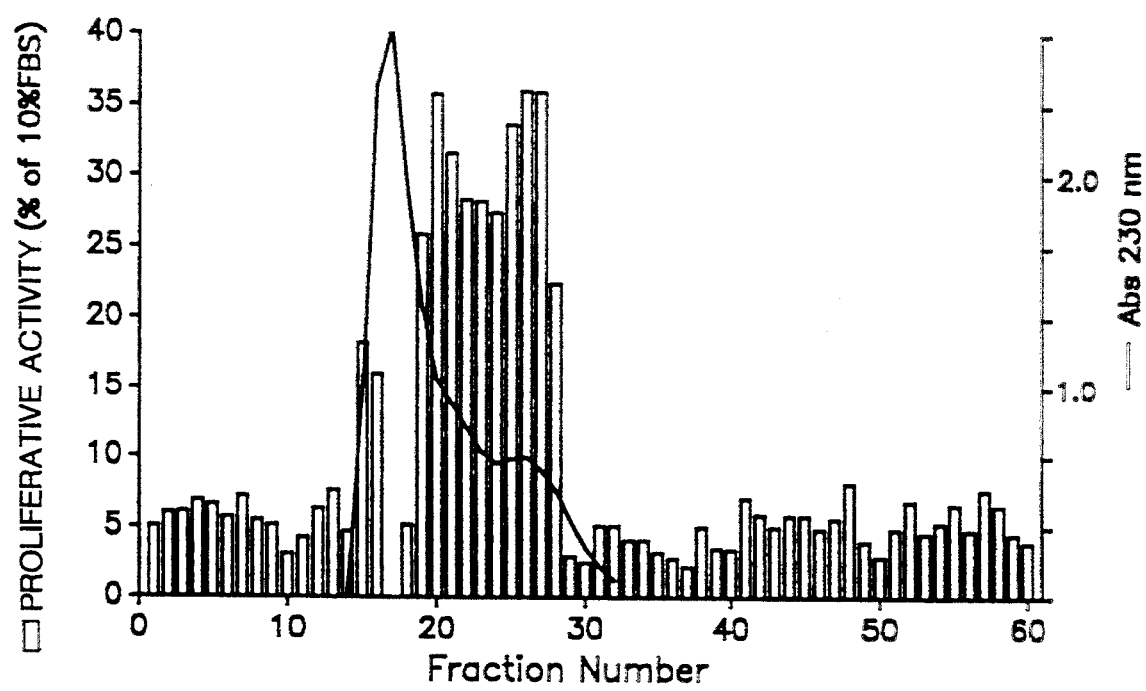
FIG. 2 describe the proliferative activity of OT-1 on MG-63 cells after Sephacryl S100 chromatography.

A 4.8×30 cm column is packed with heparin Sepharose CL-6B and equilibrated with a buffer containing 0.1M NaCl, 10 mM Tris HCl, pH 7. The final extract (approx. 200 ml of hard tissue extract) is applied to the column. The column is washed with the same buffer and a linear gradient from 0.1–3.0M NaCl in 10 mM Tris HCl, pH 7, is applied. Twelve ml fractions are collected. Aliquots of each fraction are assayed in the MG-63 proliferative assay. FIG. 1a describes that active fractions eluted at approximately 0.3M NaCl. These fractions (17–22) are pooled, dialyzed against 0.1M NaCl, 10 mM Tris HCl, pH 7, and reapplied to the same column. Active fractions (1–38) (FIG. 1b) eluting at 0.1M NaCl are pooled, dialyzed in 50 mM ammonium bicarbonate, lyophilized, reconstituted in 200 mM NH$_4$HCO$_3$ and applied to a Sephacryl S-100 column. Five ml fractions are collected and aliquots of each fraction are assayed on MG-63 cells for proliferative activity. The results are described in FIG. 2. The active fractions had an apparent molecular weight of less than about 20 kD. Fractions 19–28 are pooled, lyophilized and reconstituted in 1 ml 0.1% TFA.

HPLC chromatography is performed using C$_{18}$ RP HPLC (10×250 cm) with a gradient of 0.1% TFA (buffer A) and 0.1% TFA/70% acetonitrile (buffer B) at a flow rate of 2 ml/min.

Figure 3:
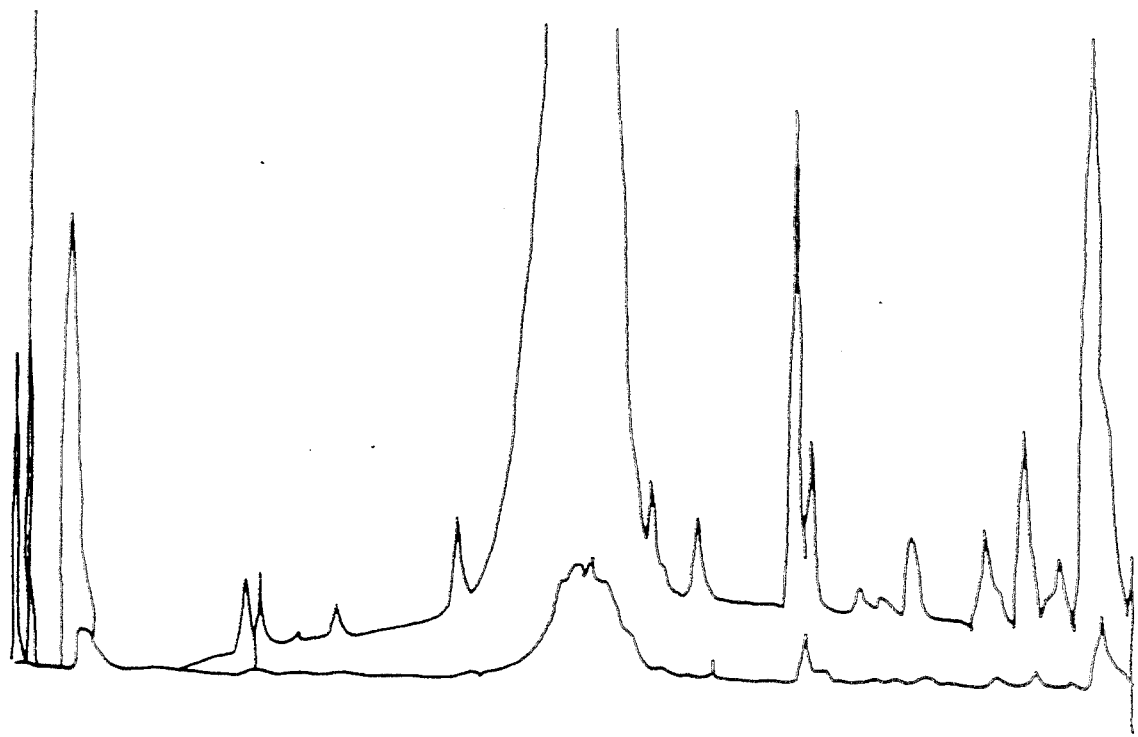
FIG. 3 describe the elution profile of OT-1 after chromatography on a C8 reverse phase HPLC column.

The fractions eluting at 37% acetonitrile stimulated proliferation of MG-63 and C433 cells. Fractions having this activity (32–33) are rechromatographed on a C8 reverse phase HPLC column and fractions are collected by hand (FIG. 3).

The partial amino acid sequence of fraction 17 is determined to be M-A-G-L-G-D-E-F-G-D [SEQ ID NO: 1], and comprises the partial amino acid sequence of the proteinaceous factor referred to herein as OT-1.

EXAMPLE 3

Isolation of OT-2 from Deer Antler Tissue

Seven antlers are obtained from male deer (red and axis deer) during the growing season and immediately frozen in dry ice. The fur is removed with a scalpel. Antlers are thawed to remove the velvet (zone A) and then immediately frozen in liquid nitrogen. The hard tissue (zone B) is cut with a saw into smaller pieces (approx. 1 to 1.5 inches long). The tissue is crushed inside a steel cylinder using a hammer and pulverized in a small coffee grinder. The whole procedure is performed in liquid nitrogen. The total weight of Zone A (velvet) and of Zone B (hard tissue) is 198.0 g and 506.1 g, respectively.

The hard tissue is extracted (1:2.5 w/v) by stirring at 4° C. for 48 hours in 1250 ml of extraction buffer containing 0.5M EDTA, 20 mM Tris, 25 mM benzamidine, 1 μg/ml leupeptin, 1 mM PMSF (dissolved in isopropanol, 100%) adjusted to a final pH of 7.0. After 48 hours, the extract is centrifuged at 6000 rpm for 20 min at 4° C. The supernatant is removed and frozen at −70° C.

A second extraction of the pellet is performed by adding 500 ml of fresh extraction buffer to the pellet and stirring the mixture at 4° C. for another 48 hours. After this period, the extract is centrifuged at 6000 rpm for 20 min at 4° C., supernatants from the first and second extractions are combined and centrifuged at high speed at 15,000 g for 1 hr at 4° C.

The supernatant is removed, and dialyzed against 10 mM Tris, 0.1M NaCl, pH 7.0. Protein concentration is determined by the absorbance at 280 and 260 mm. The dialysate had a total volume of 4.61 and contained 44.2 g of total protein (9.6 mg/ml).

EXAMPLE 3A

Purification of the Biological Activity of OT-2

Figure 4:
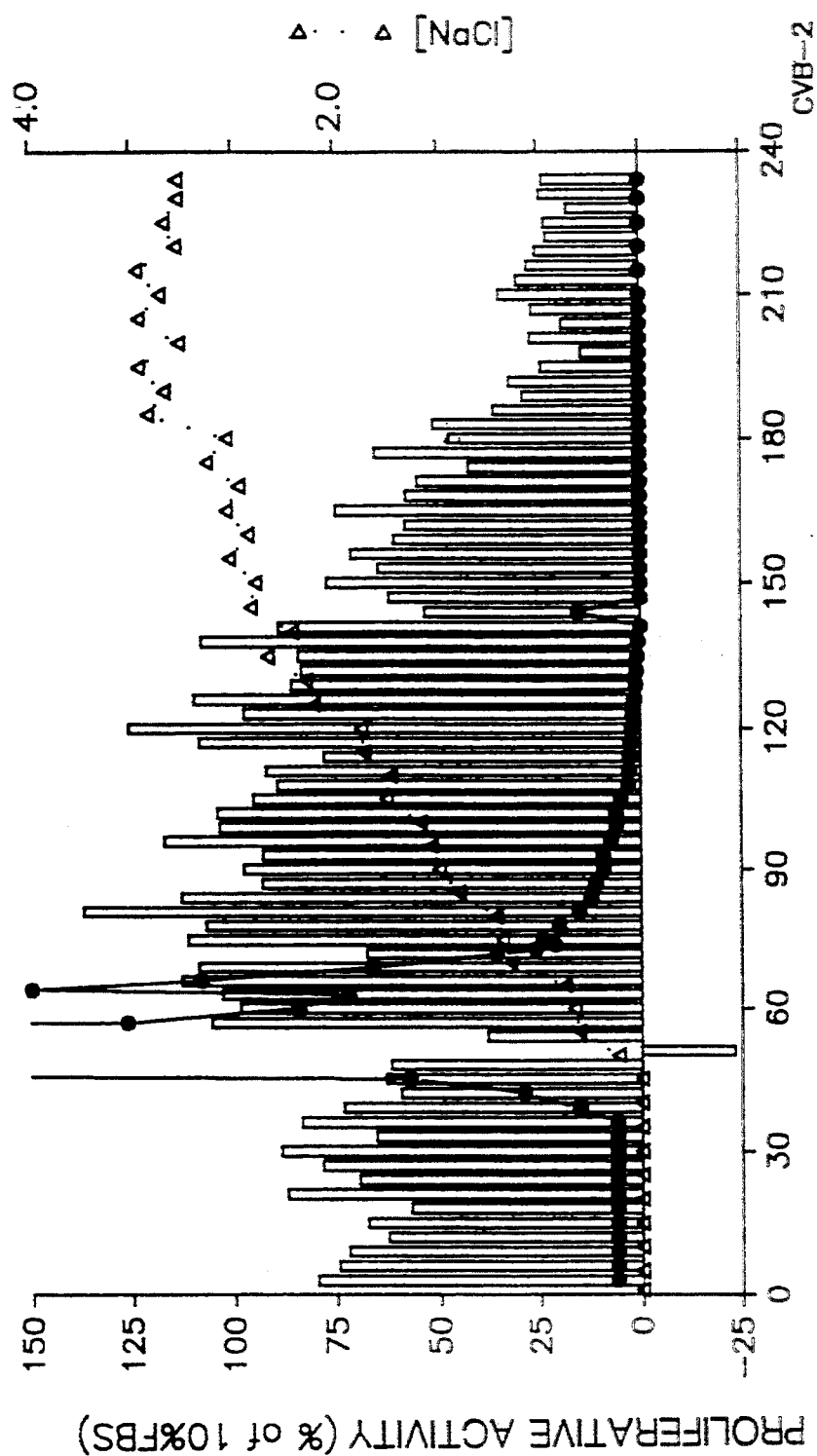
FIG. 4 describes the heparin Sepharose chromatography elution profile and proliferative activity of OT-2 on MG-63 cells.

A 4.8×30 cm column is packed with 308 ml of heparin Sepharose CL-6B and equilibrated with a buffer comprising 0.1M NaCl, 10 mM Tris HCl, pH 7. The final dialysate (4.6 l of hard tissue extract) of Example 3 containing OT-2 is applied to the column. The column is then washed with 1.5 l of buffer comprising 0.1M NaCl, 10 mM Tris HCl, pH 7, at a flow rate is 150 ml/hr. Twelve ml fractions are collected. The unbound material is collected for further chromatography. The bound material is eluted with a linear gradient from about 0.1 to about 3M NaCl in 10 mM Tris HCl, pH 7.0. The column is then washed with 4M NaCl wash. Aliquots of each fraction are assayed for proliferative activity on MG-63 cells (FIG. 4). The activity of each fraction is compared to that of 10% fetal bovine serum (FBS). One hundred units (100 u) is defined as the proliferative activity equivalent to 10% FBS. The specific activity of OT-2 at this stage of the isolation is 51 U/mg.

The unbound material is extensively dialyzed against 50 mM NH$_4$HCO$_3$, lyophilized, reconstituted in 630 ml of 0.1M NaCl, 10 mM Tris HCl, pH 7 and reapplied to the same column, then washed with 4 l of same buffer at 150 ml/hr flow rate. The bound material is eluted with a 2 l linear gradient from 0.1 to 3M NaCl, followed by a 4M NaCl wash in the same buffer. Fraction volume is 12.5 ml. Three hundred μl of 4 consecutive fractions are pooled, added to 120 μl of 1% BSA, dialyzed in 3.5 kD mw cut-off membranes versus 10 l PBS for 24 hours and two changes of 5 l of DMEM/F12 media for 36 hours. The samples are then sterilized through 0.2 μm membrane filters and assayed on MG-63 cells for proliferative activity.

Figure 5:
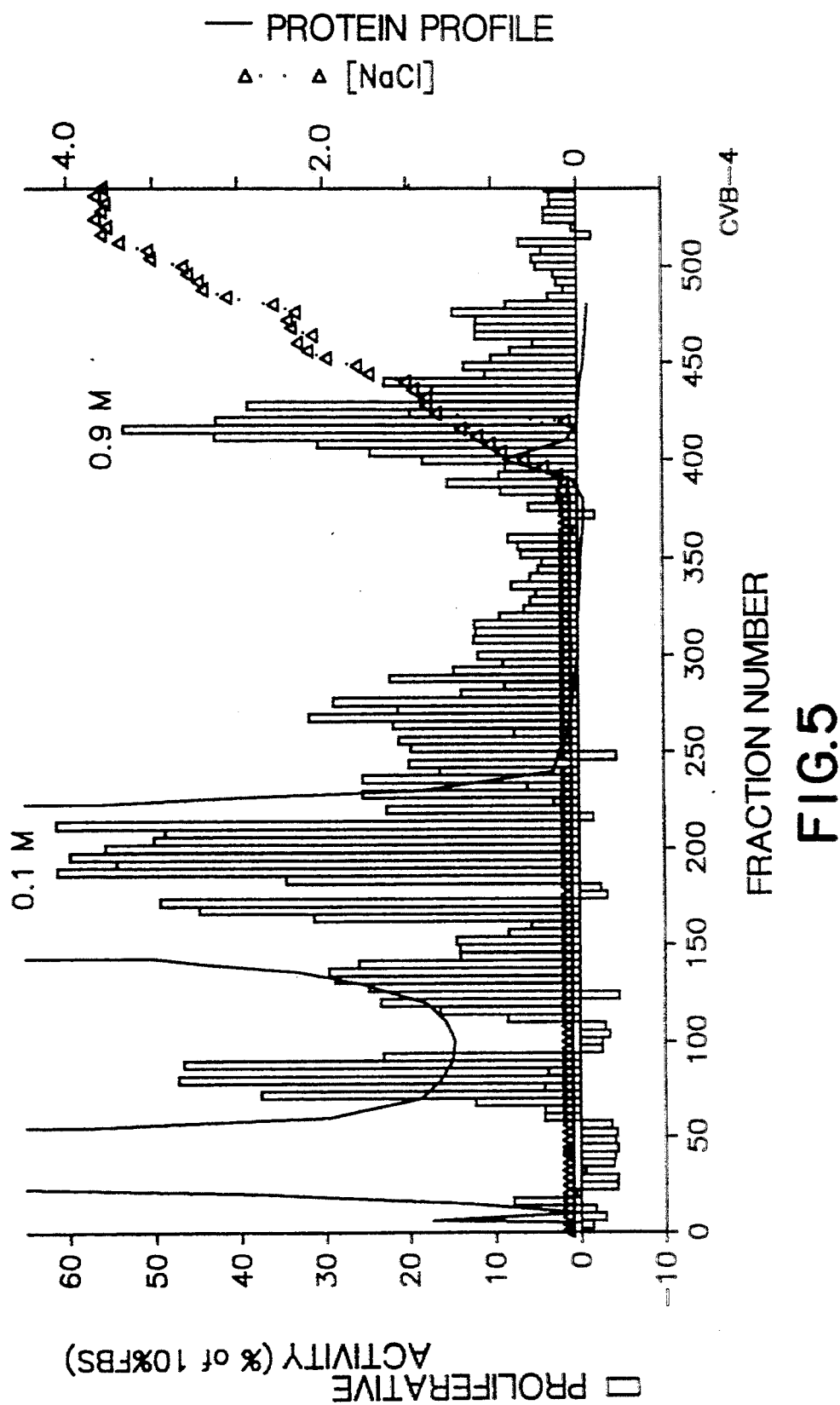
FIG. 5 describes the proliferative activity OT-2 on MG-63 cells after repeating heparin Sepharose chromatography.

FIG. 5 describes the elution profile of the second heparin Sepharose column and the results of the proliferation assay. The fractions containing the peak of biological activity (fractions 360 to 470), eluting at about 0.9M NaCl, are pooled and protein content assessed by reading absorbance at 280 and 260 nm. The total volume after pooling the fractions is 1000 ml with total protein of 61 mg. The specific activity of OT-2 at this stage of the isolation is 5408 U/mg.

Figure 6:
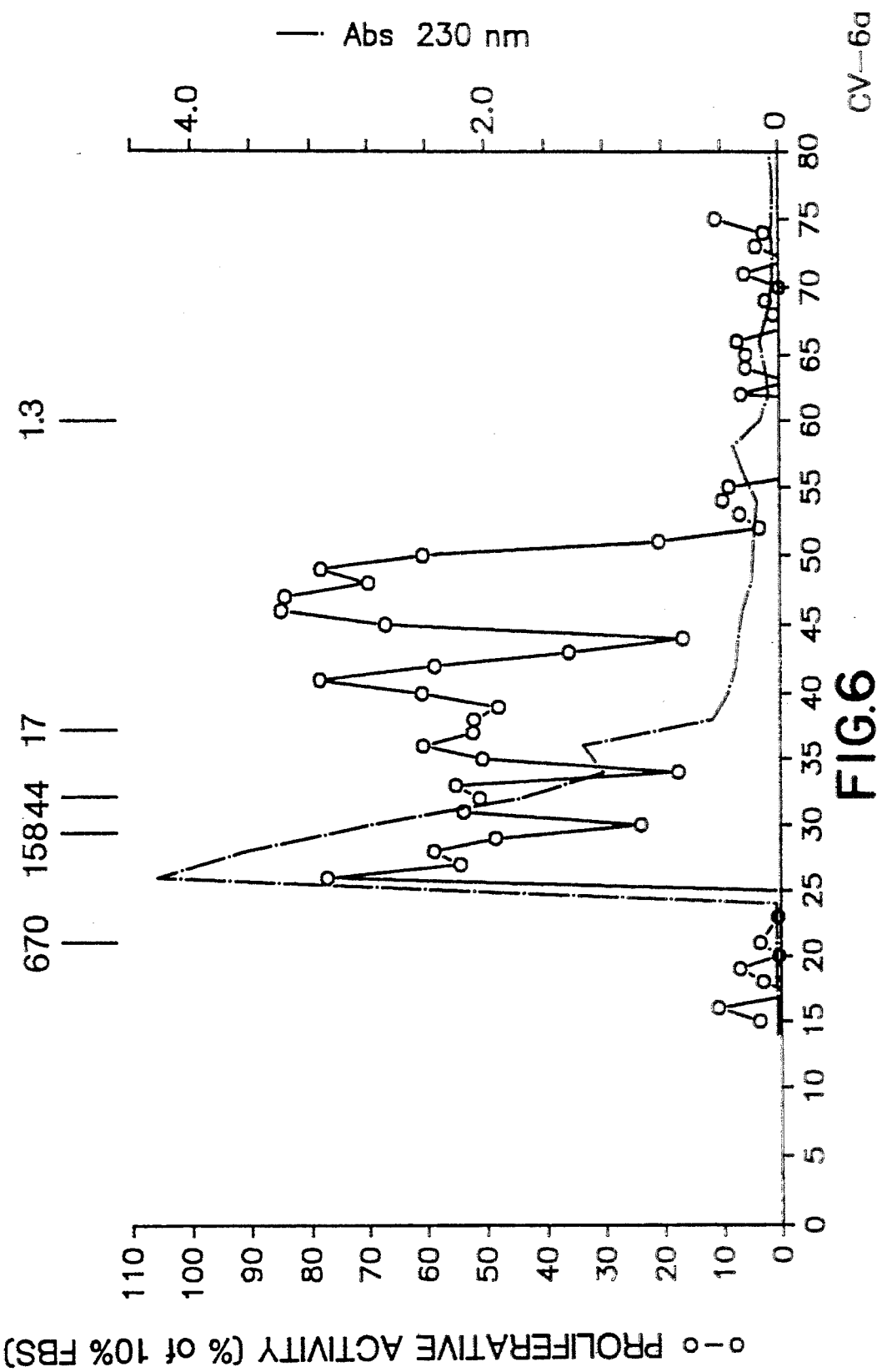
FIG. 6 describes the proliferative activity of OT-2 on MG-63 cells after Sephacryl S100 chromatography.
Figure 7:
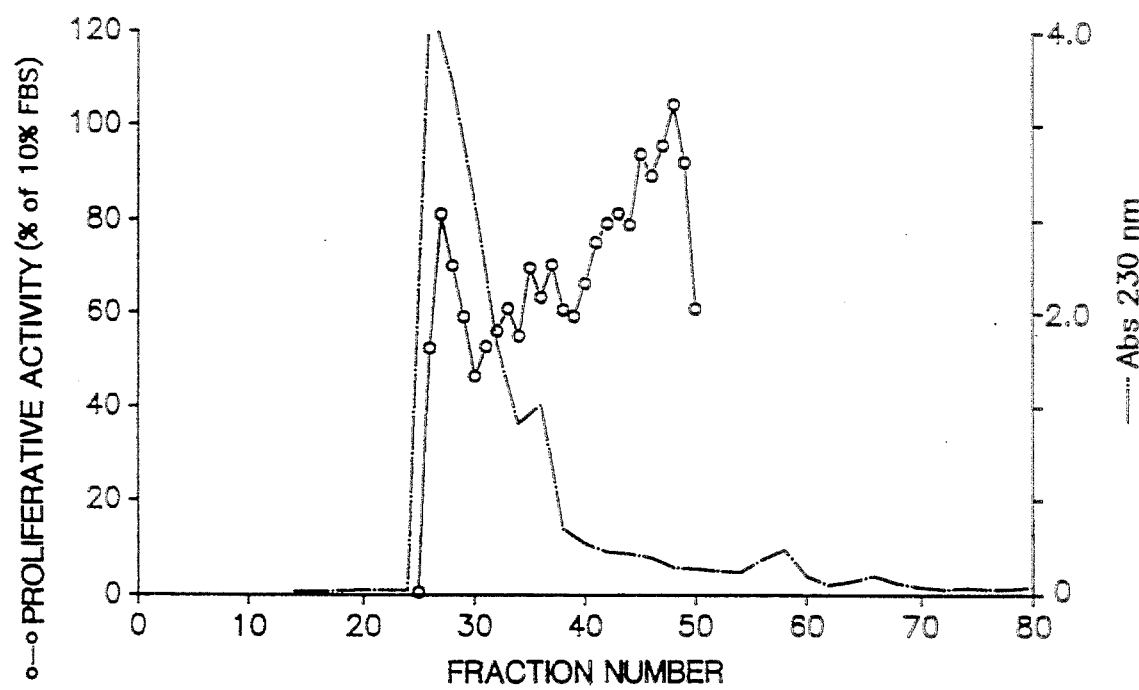
FIG. 7 describes the proliferative activity of OT-2 on C433 cells after Sephacryl S100 chromatography.

The pooled fractions are dialyzed against 50 mM NH$_4$HCO$_3$, lyophilized, reconstituted in 15 ml of 50 mM NH$_4$HCO$_3$ applied to a 2.5×100 cm column packed with Sephacryl S100, and eluted with 730 ml of 50 mM NH$_4$HCO$_3$. The fraction volume is 9.1 ml. The protein content is assessed by reading absorbance at 230 nm. FIG. 6 describes the elution profile and proliferative activity on MG-63 cells. The elution position of molecular weight standards from the Sephacryl S100 column is also shown in FIG. 6. 50 μl of 1% BSA are added to 500 μl of each fraction. The fractions are then lyophilized and reconstituted in 500 μl of DMEM/F12 media. After sterilization through 0.2 μm membrane filters, the samples are assayed for proliferative activity on C433 (FIG. 7) cells. Fractions 39–44 which exhibited proliferative activity in both MG-63 and C433 cells, but not MC3T3 cells, are pooled. The specific activity of OT-2 at this stage of the isolation is 37,600 U/mg.

Figure 8:
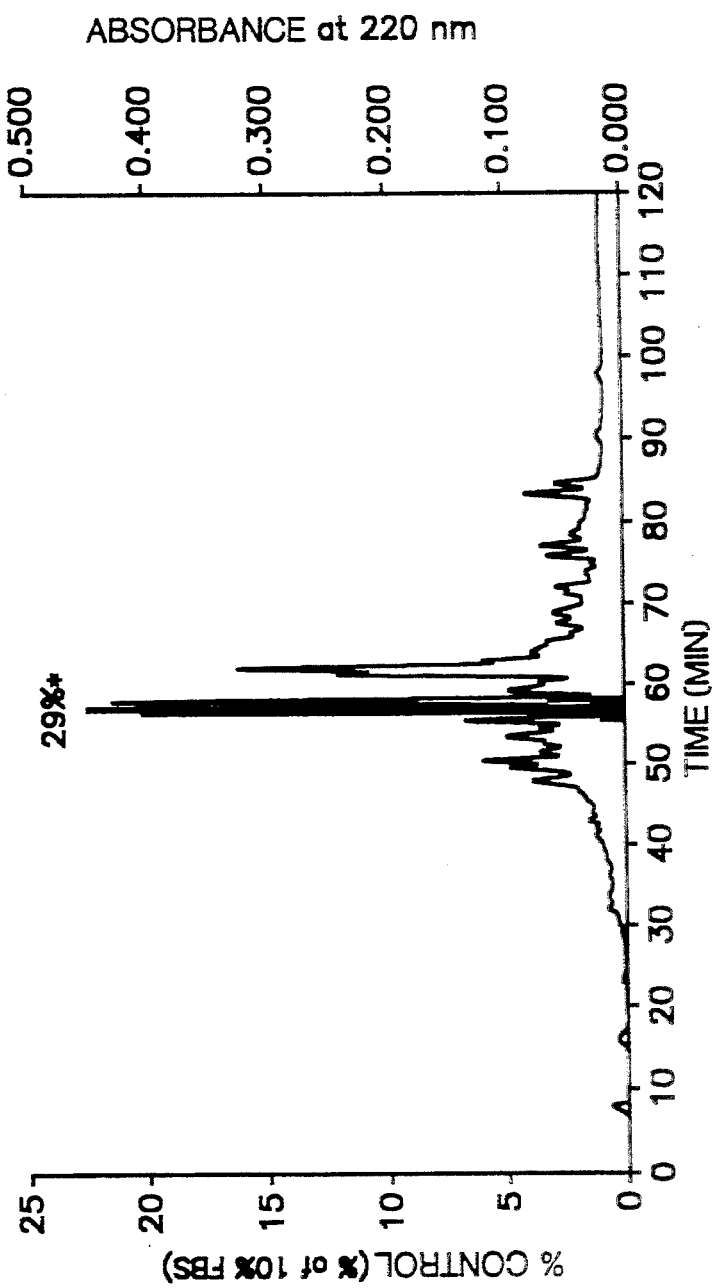
FIG. 8 describes the proliferative activity of OT-2 on C433 cells after chromatography on a C18 reverse phase HPLC column.

HPLC chromatography is performed using a reverse phase C$_{18}$ column (10×250 cm) eluted with a gradient of 0.1% TFA and 0.1% TFA/70% acetonitrile at a flow rate of 2 ml/min. The absorbance at 220 nm is monitored. To measure the biological activity in HPLC fractions, an aliquot of the fraction is lyophilized in the presence of carrier BSA (1%) and reconstituted in DMEM/F12 50/50 medium. Stimulation of proliferation in C433 cells and MG-63 cells is observed in the material which eluted at 29% acetonitrile. The activity on C433 cells is described on FIG. 8. Three tenths percent of the fractions is used to assay the proliferative activity of the eluant. The specific activity of OT-2 at this stage of the isolation is 231,000 U/mg.

Figure 9:
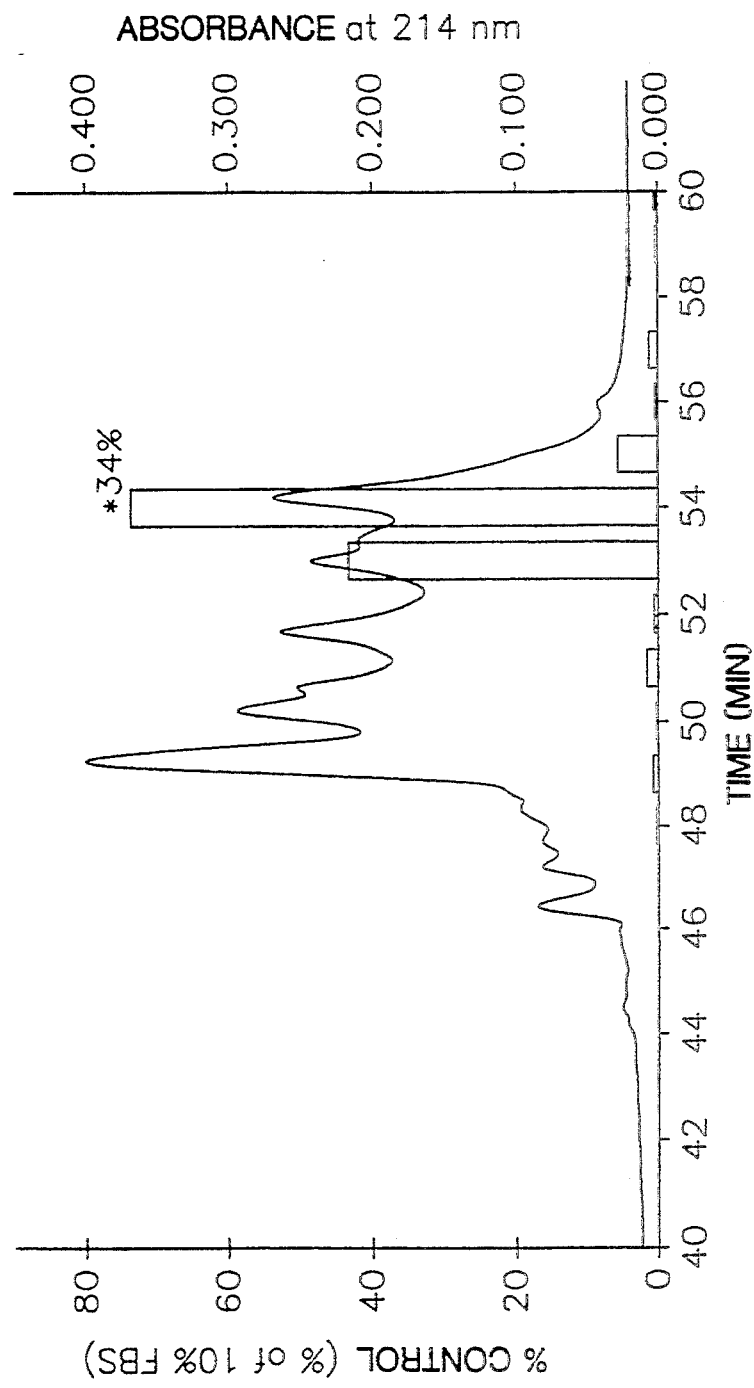
FIG. 9 describes the proliferative activity of OT-2 on C433 cells after chromatography on a C4 reverse phase HPLC column.

Fractions eluting from the C$_{18}$ column at 29% acetonitrile which stimulated the proliferation of both C433 and MG-63 cells are applied to a C4 reverse phase HPLC column (2.1×150 mm). Elution is performed with a gradient of 0.1% TFA and 0.1% TFA/70% acetonitrile at a flow rate of 0.15 ml/min. The absorbance is monitored at 214 nm. Seven percent of each fraction is used to assay biological activity. The biological activity eluted at 34% acetonitrile (FIG. 9). In comparison, human recombinant IGF-I eluted at 33% acetonitrile from this column. The specific activity of OT-2 at this stage of the isolation is 9.4×10$^6$ U/mg.

Figure 10:
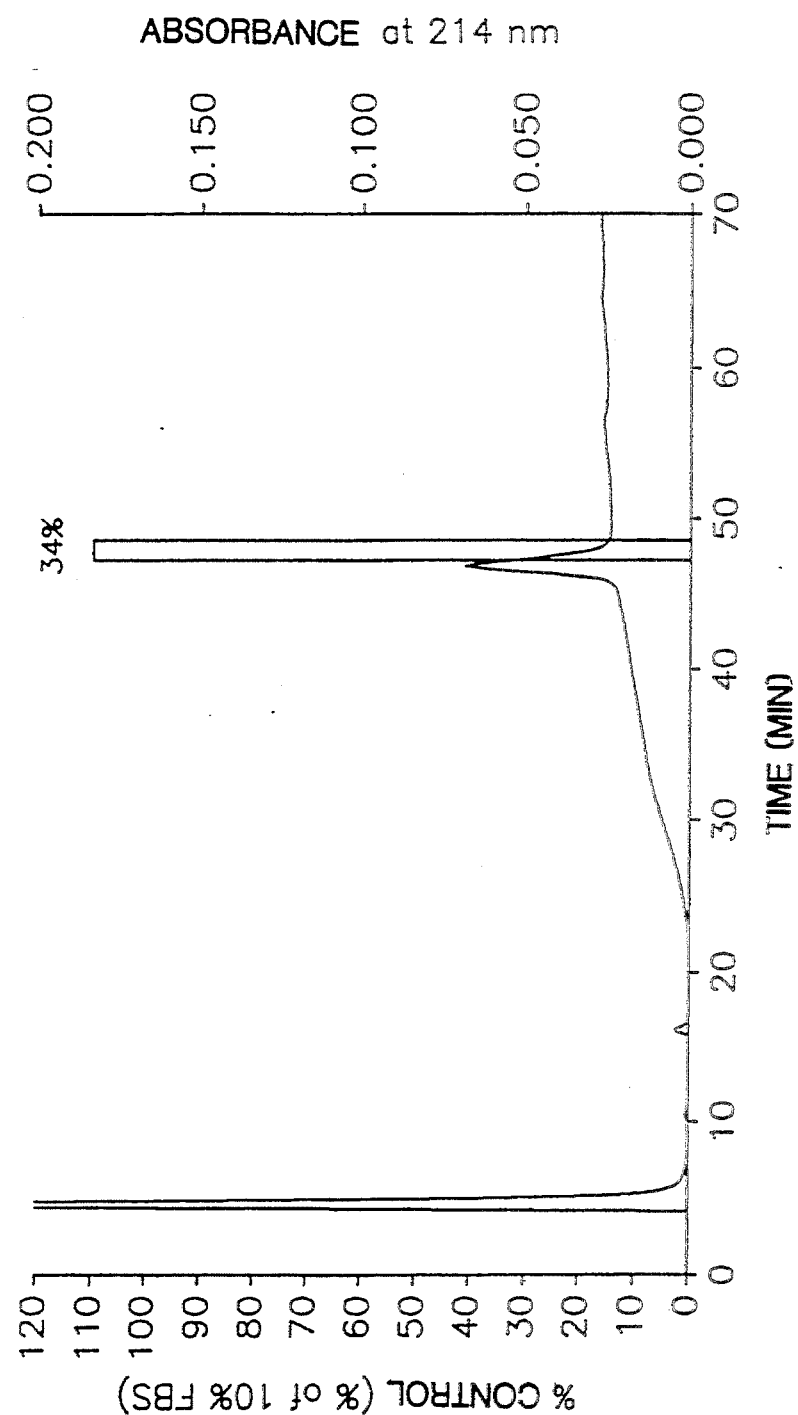
FIG. 10 describes proliferative activity of OT-2 on C433 cells after repeating the chromatography on a C4 reverse phase HPLC column.
Figure 11:
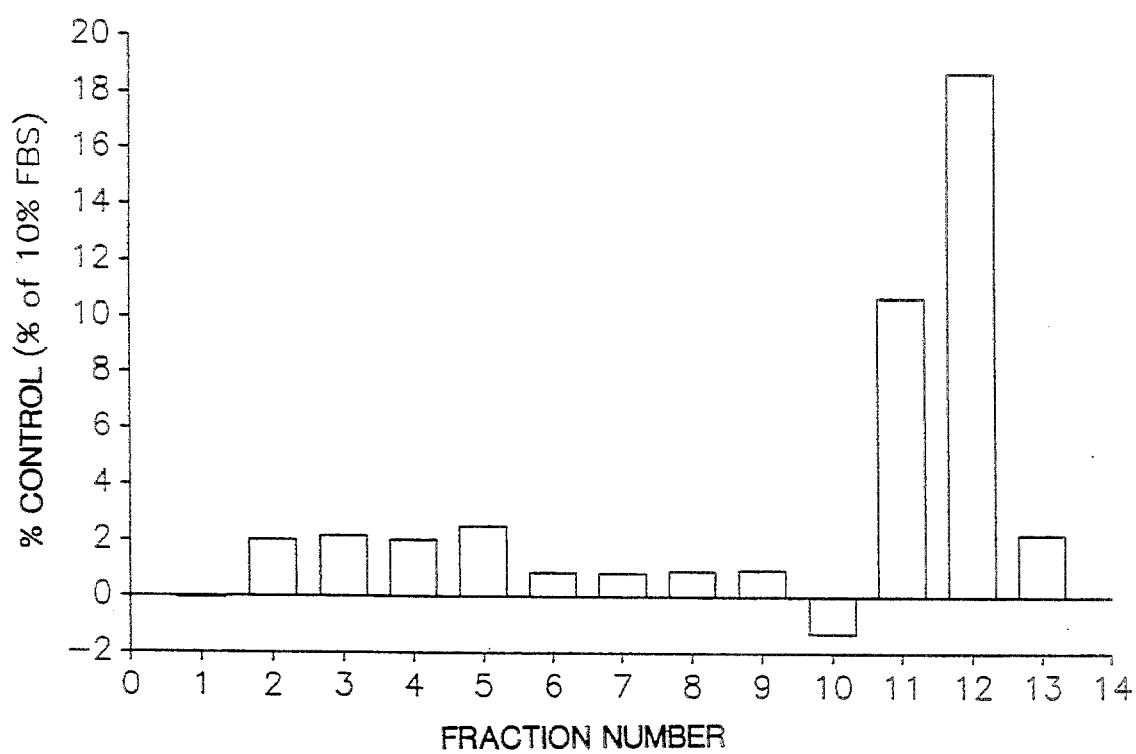
FIG. 11 describes the proliferative activity of OT-2 after chromatography on a C8 reverse phase HPLC column.
Figure 12:
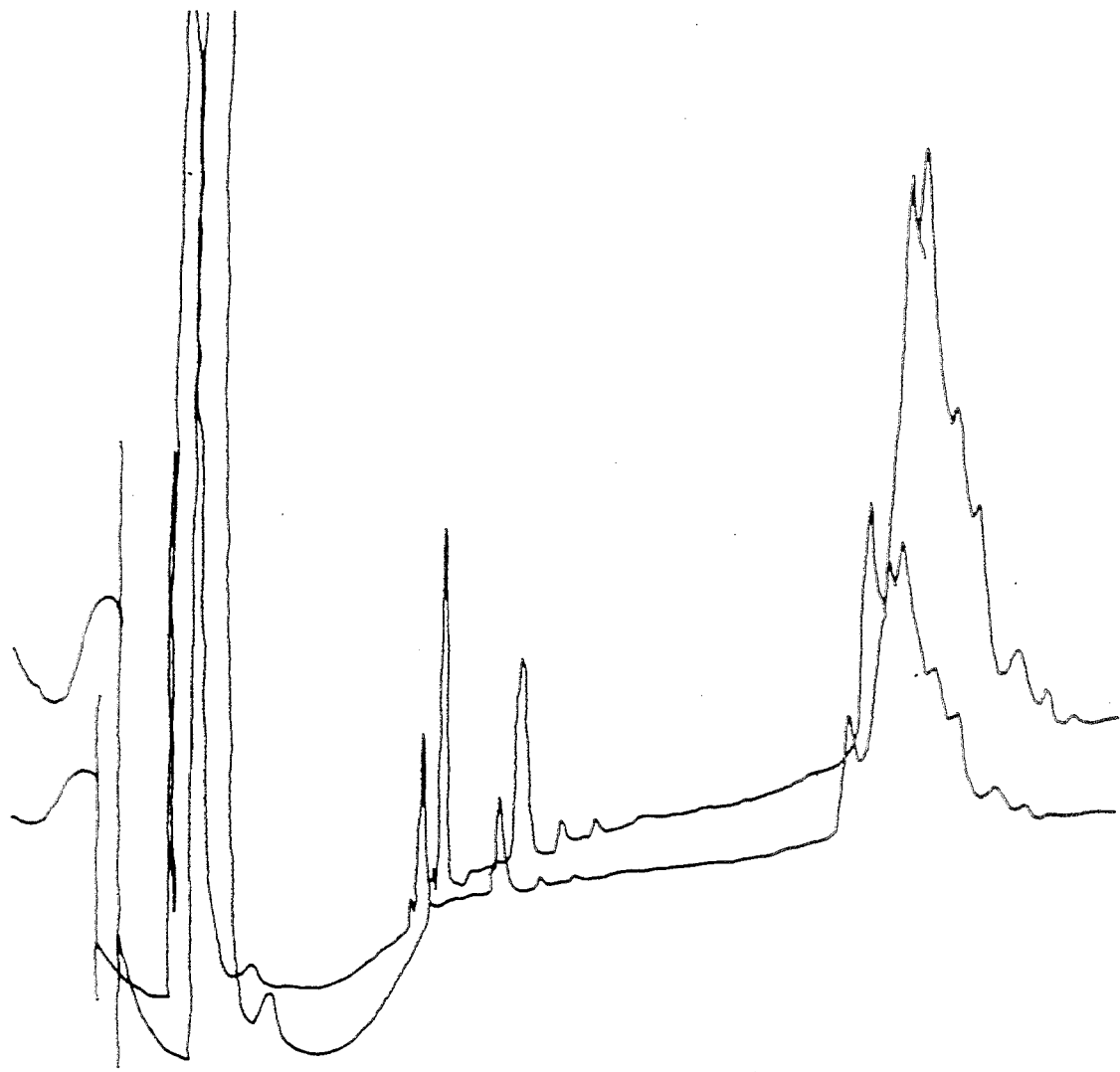
FIG. 12 describes the absorbance profile of OT-2 after chromatography on a C8 reverse phase HPLC column of fractions represented in FIG. 11.

After re-chromatography of the 34 % acetonitrile eluate on a second C4 reverse phase HPLC column, proliferative activity again eluted in the same position (FIG. 10). The specific activity of OT-2 at this stage of the isolation is 8.2×10$^7$ U/mg. This biological activity is re-chromatographed on a C8 reverse phase HPLC column analytical column (2.1×30 mm) with a gradient of 0.1% TFA and 0.1% TFA/70% acetonitrile at a flow rate of 0.15 ml/min. The absorbance is monitored at 214 nm. Fractions representing pronounced absorbance peaks are collected by hand. FIG. 12 describes the elution profile from the C8 reverse phase high pressure liquid chromatography (RPHPLC). Ten percent of each fraction is used to assay biological activity. One fraction (Fraction 12) eluting at 35% acetonitrile had proliferative activity for C433 cells (FIG. 11).

The partial amino acid sequence of fraction 12 is determined. This fraction is applied to a pulsed liquid microsequencer and is found to have an amino acid sequence, (X) F E T L F G A/V E D V I/D A L Q F V C G D [SEQ ID NO: 2], which is similar to, but distinct from, that of human, bovine, deer, and mouse IGF-I, which are identical at the N-terminal end. The initial N-terminal amino acid sequence is difficult to determine. It is assigned no designation for that reason. The proteinaceous factor comprising this partial amino acid sequence is herein referred to as OT-2. In addition to having an amino acid sequence distinct from that of human IGF-I, OT-2 elutes after IGF-I in both C$_{18}$ HPLC and MonoS columns. Antibodies which recognize OT-2, do not recognize IGF-i or IGF-II.

TABLE 1

Summary of purification of OT-2 (Antlerin 2)

| | Protein | Total Activity (Units)* | Specific Activity U/mg |
|---|---|---|---|
| Crude bone extract | 506 g | | |
| Heparin-Sepharose | 44.2 g | 2.25 × 10$^6$ | 51 |
| Heparin-Sepharose | 61 mg | 3.3 × 10$^5$ | 5408 |
| Sephacryl S100 | 2.25 mg | 84,600 | 37,600 |
| C18 Reverse Phase HPLC | 50 μg | 11,550 | 231,000 |
| C4 Reverse Phase HPLC | 1.17 μg | 11,000 | 9.4 × 10$^6$ |
| C4 Reverse Phase HPLC | 200 ng | 16,500 | 8.2 × 10$^7$ |

TABLE 1-continued

Summary of purification of OT-2 (Antlerin 2)

|  | Protein | Total Activity (Units)* | Specific Activity U/mg |
|---|---|---|---|
| C8 Reverse Phase HPLC | 13 ng | 582 | $4.3 \times 10^7$ |

*100 U represents the equivalent proliferative activity of 10% FBS.

EXAMPLE 4

Isolation of OT-3 from Deer Antler Tissue

Figure 13:
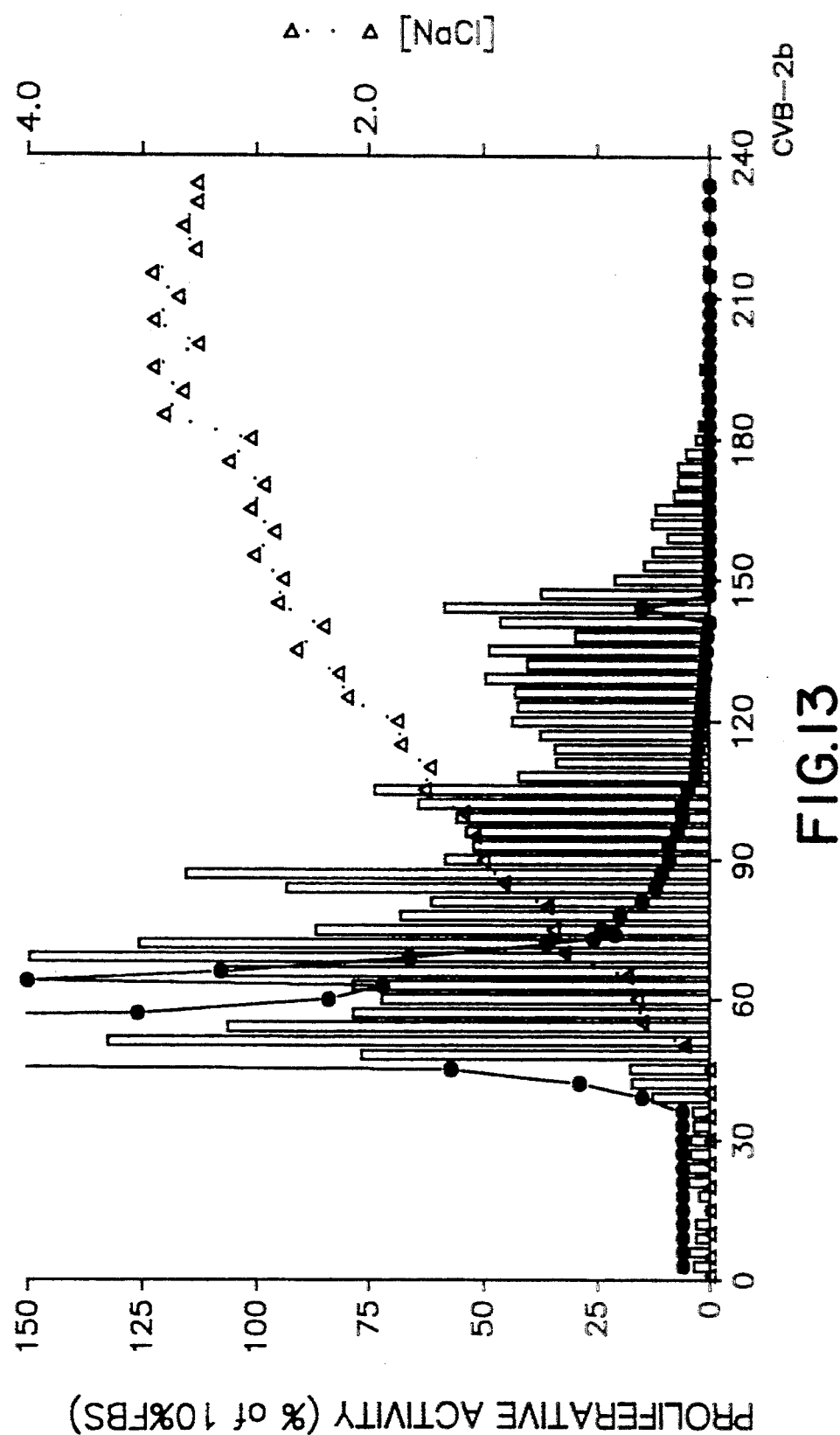
FIG. 13 describes the proliferative activity OT-3 on MC3T3 cells after heparin Sepharose chromatography.
Figure 14:
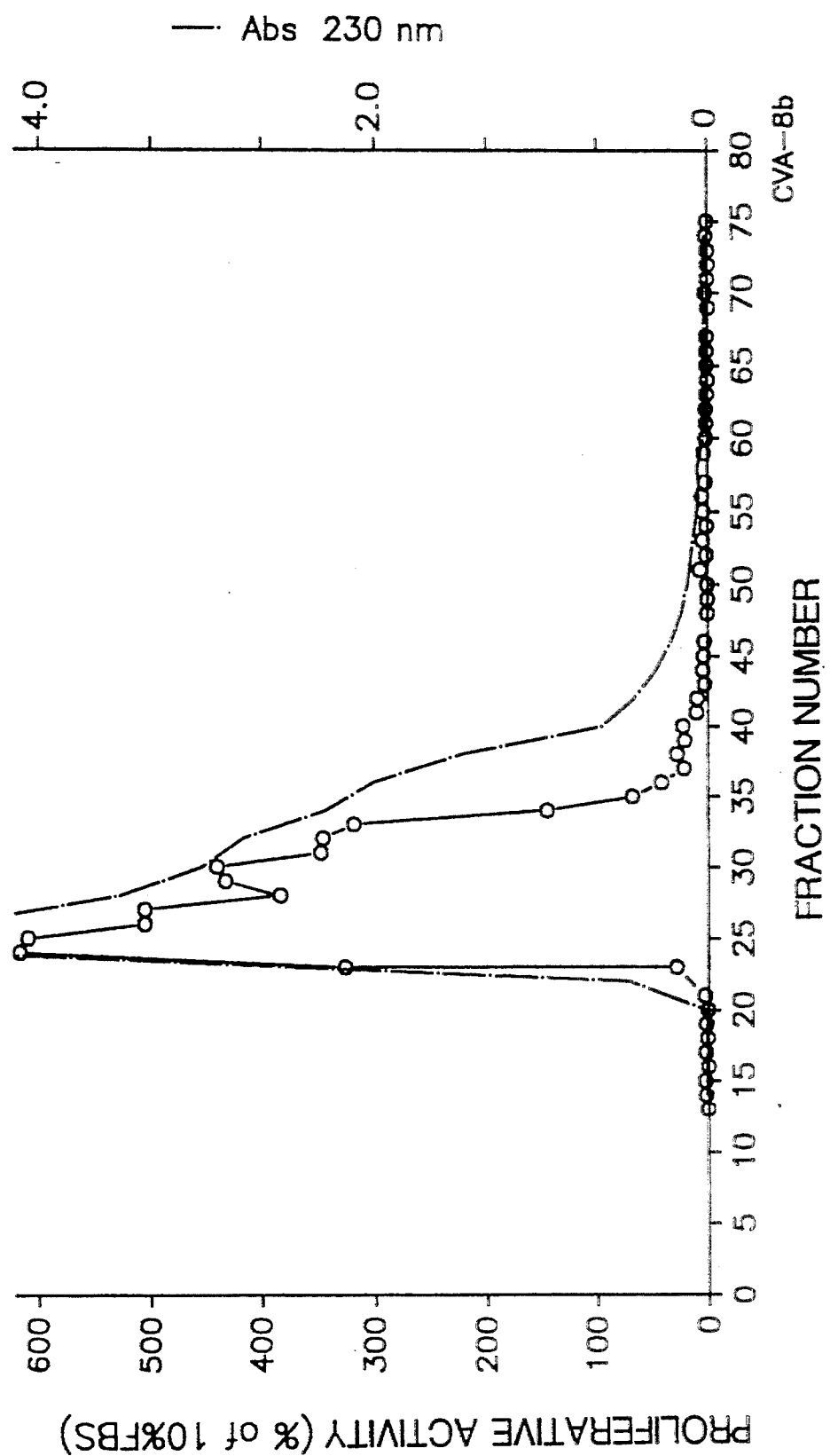
FIG. 14 describes the proliferative activity of OT-3 on MC3T3 cells after Sephacryl S100 chromatography.
Figure 15:
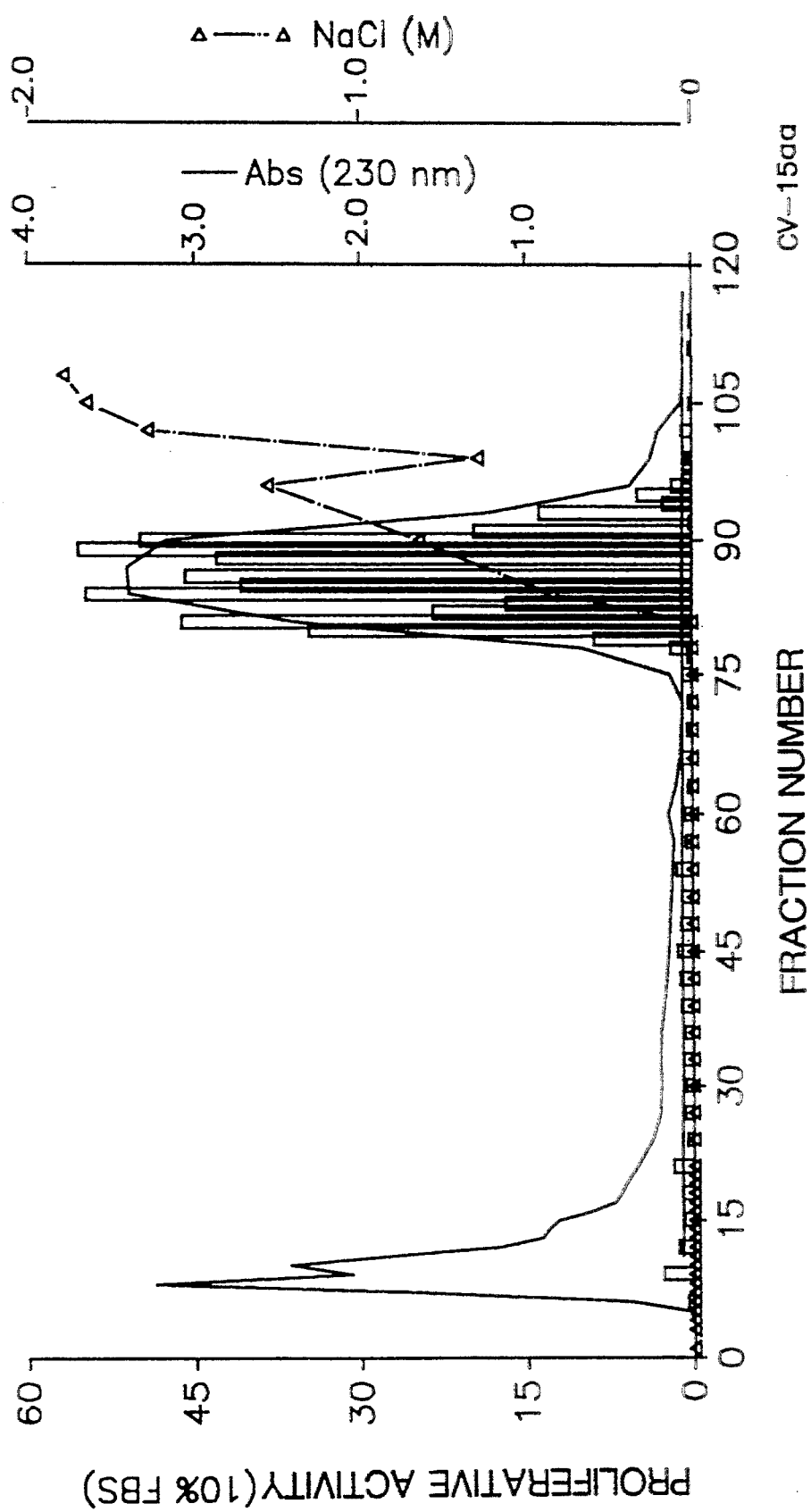
FIG. 15 describes the proliferative activity OT-3 on MC3T3 cells after Heparin Sepharose chromatography.
Figure 16:
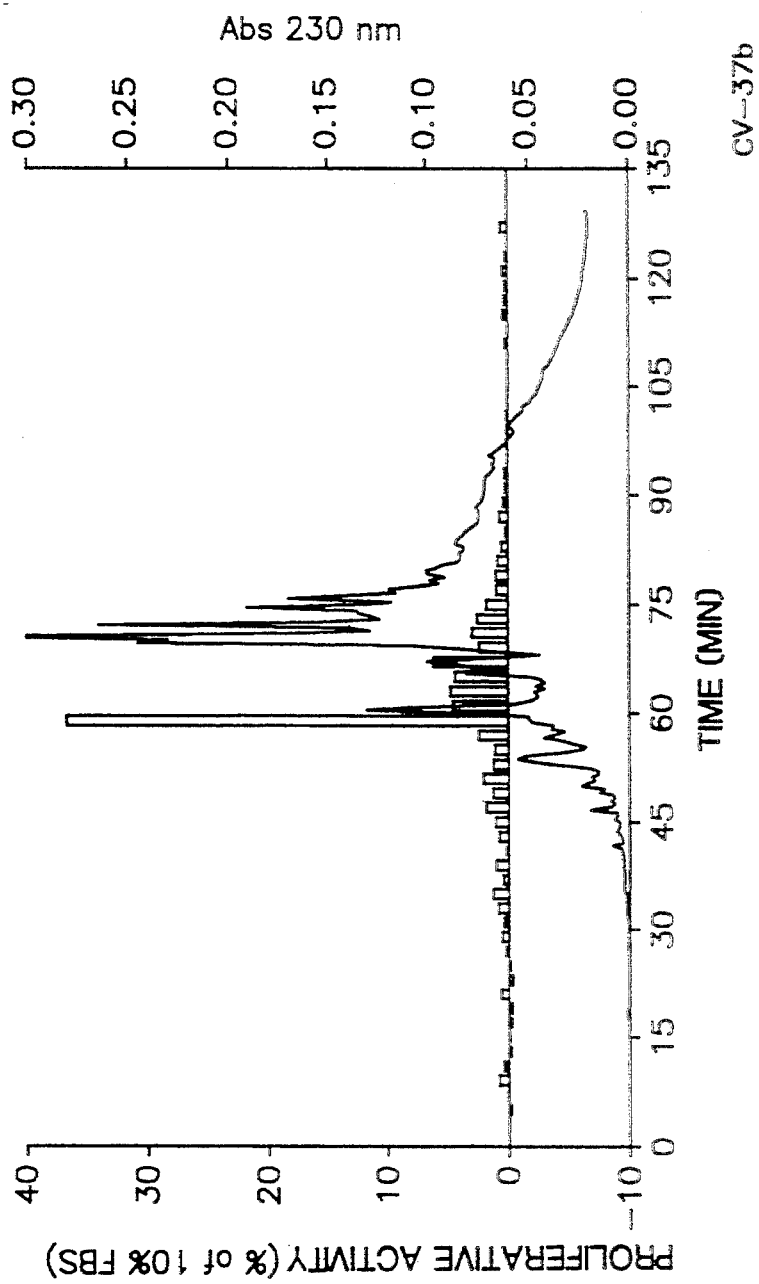
FIG. 16 describes the proliferative activity of OT-3 on MC3T3 cells after chromatography on a C18 reverse phase HPLC column.
Figure 17:
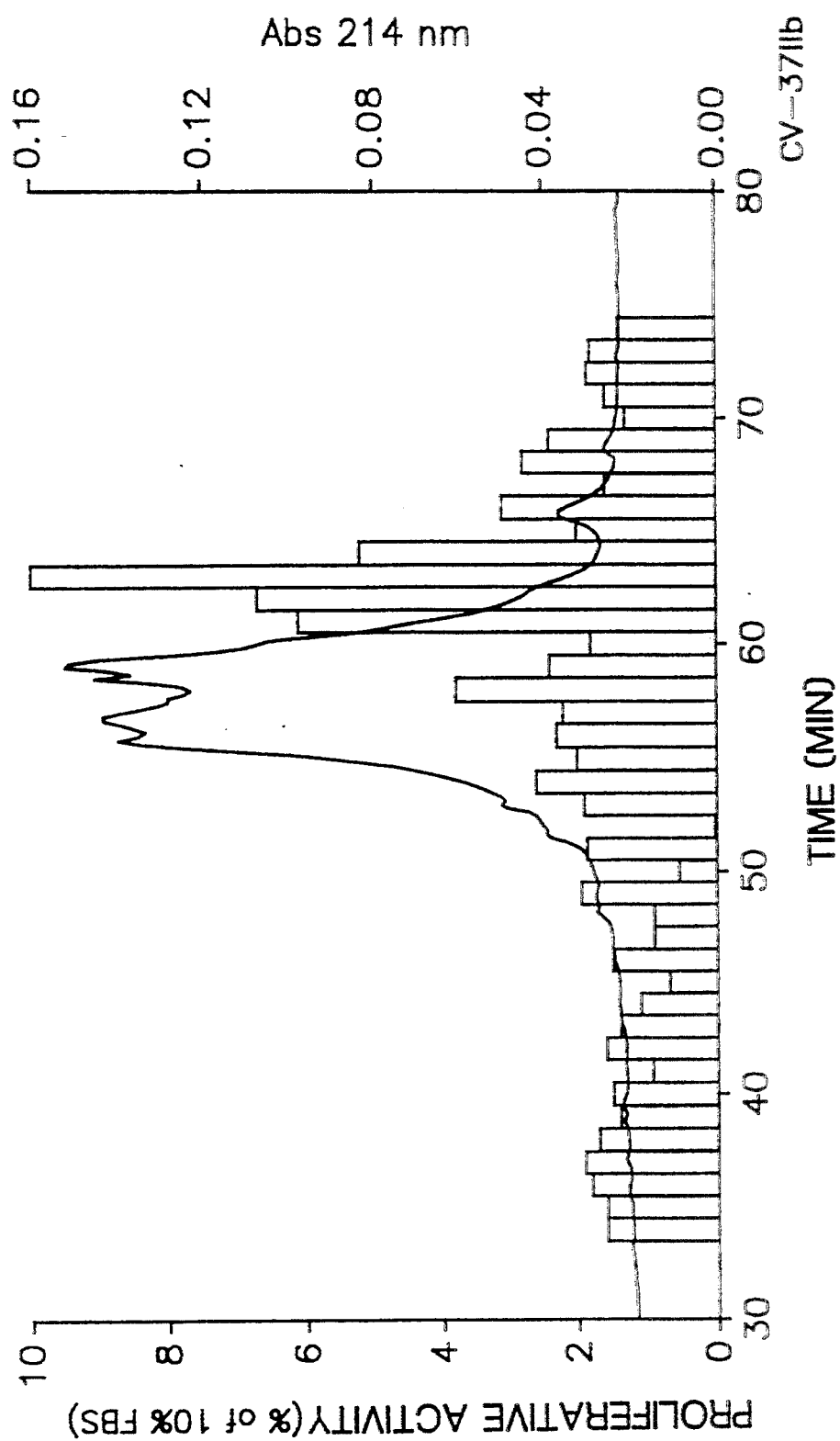
FIG. 17 describes the proliferative activity of OT-3 on MC3T3 cells after chromatography on a C4 reverse phase HPLC column.

Fractions 61–78 with MG-63 activity eluting at 0.4M NaCl from the first heparin Sepharose column of Example 3A are pooled, dialyzed in 50 mM ammonium bicarbonate and applied to a Sephacryl S-100 column prepared as in Example 4 (FIG. 13). Fractions 22–37 with MC3T3 activity eluting between 20–100 kD (FIG. 14) are pooled and reapplied to heparin Sepharose (FIG. 15). Fractions 83–94 containing biological activity eluted at 1.4M. These fractions are then pooled and applied to reverse phase HPLC on a $C_{18}$ column. The biological activity eluted at 32% acetonitrile (FIG. 16). FIG. 17 shows the elution profile of MC3T3 proliferative activity after C4 column chromatography performed as described in Example 3A. In the assay described herein and performed on OT-3, OT-3 did not stimulate proliferation of MG-63 or M433 cells.

EXAMPLE 5

Isolation of OT-4 from Deer Antler Cell Conditioned Medium

Deer Antler Cell Isolation

Antlers are cut from male red and axis deer during the early stage of antler growth (mid-May). The velvet is discarded and tissue fragments (about 1 cm³ volume) are isolated from the distal half of each antler and kept in cold αMEM medium. The fragments are then transferred to Petri dishes, finely minced with scalpels, and subjected to four consecutive 30 minute digestions in 0.25% collagenase, 0.25% trypsin Hanks balanced salt solution (5 ml/cm³ tissue) at 37° C. on a shaking platform. At the end of each digestion the cells in suspension are collected, washed with 10% FBS αMEM and seeded in the same medium in culture flasks.

Collection of Deer Antler Cell Conditioned Medium

Deer antler cells are seeded in roller bottles in 10% FBS αMEM. When confluent, the cells are washed 3 times with PBS and re-fed with serum free αMEM containing 0.1% BSA (0.3 ml/cm²). After 2 to 3 days, the conditioned medium is collected, clarified by centrifugation and stored at −20° C.

EXAMPLE 6

Purification of Biological Activity of OT-4

Fifteen liters of deer antler cell conditioned medium are thawed, passed through Whatman No. 4 filter paper to remove particulates and concentrated to 1.5 liters in 10 mM Tris HCl, pH 7.0 using an Omega cassette ultrafiltration apparatus with 3kD MW cut-off (Pharmacia LKB, Piscataway, N.J.). The conductivity of the concentrate is adjusted to that of 0.05M NaCl Tris buffer (10 mM Tris HCl, pH 7.0) using 4M NaCl Tris buffer and the sample is loaded on a heparin Sepharose CL-6B (Pharmacia LKB) column (5×6.5 cm) pre-equilibrated in 0.05M NaCl, Tris buffer. The unbound material is washed off the column with 1.2 liters of the same buffer, and the bound material eluted with 350 ml of 3M NaCl followed by 500 ml of 4M NaCl Tris buffer. The unbound and the 0.05M NaCl Tris wash are then reapplied to the same column and eluted with 300 ml of 3M NaCl and 300 ml of 4M NaCl Tris buffer.

Figure 18:
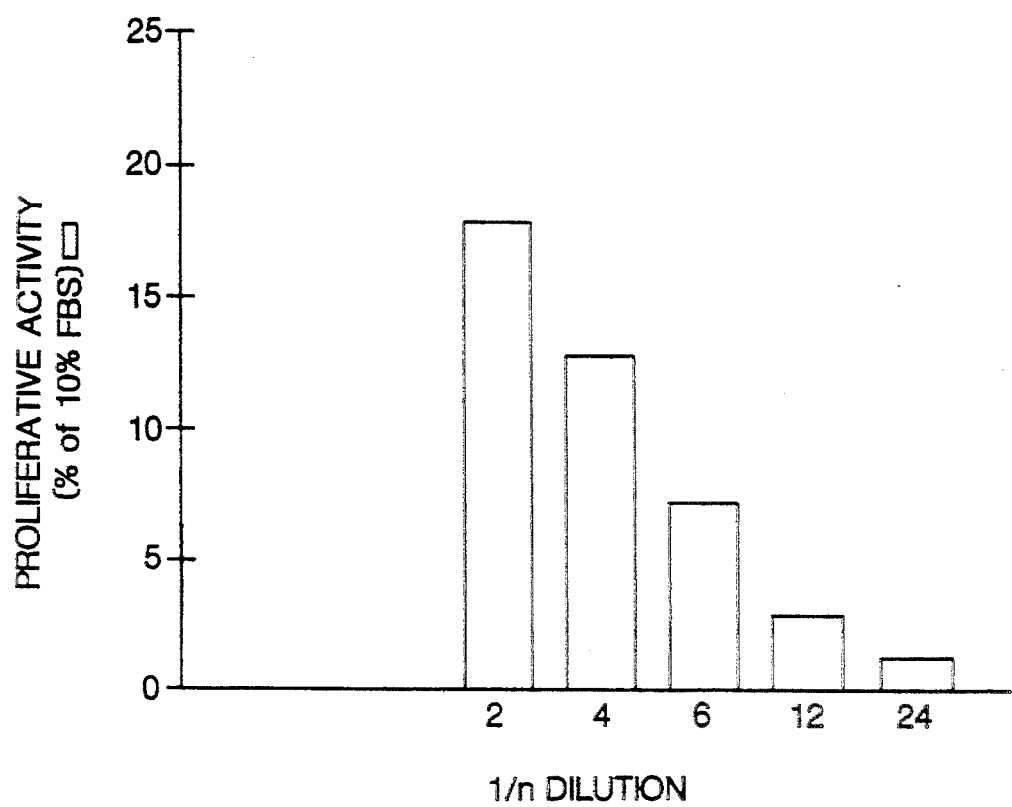
FIG. 18 describes the proliferative activity of the bound fraction of OT-4 on C433 cells assayed at 1:2 serial dilutions after heparin Sepharose chromatography.

The bound fractions of the first and second run are pooled and their absorbance at 260 and 280 nm read using BSA as a standard, giving a protein content of 335 mg/1430 ml. This material is dialyzed against 4 changes of 24 l of 50 mM $NH_4HCO_3$. Fifteen ml are lyophilized and resuspended in 3 ml of DMEM/F12 50/50 medium for assay of proliferative activity on C433 cells (FIG. 18). The specific activity of OT-4 at this stage of the isolation is approximately 4 U/mg protein.

The rest of the dialyzed material is lyophilized and redissolved in 32 ml of 4M urea. After a centrifugation to remove the insoluble matter, the sample is size fractionated on a 2.5×100 cm Sephacryl S-100 (Pharmacia LKB) column, using 10 mM Tris HCl, 4M urea pH 8.0. Each fraction had a volume of 8.3 ml, and its absorbance at 280 nm is recorded. For the assay of proliferative activity, 400 μl of every 2 consecutive fractions are pooled with 80 μl of 1% BSA and dialyzed against 2 changes of 4 l of PBS and 2 changes of 3 l of DMEM/F 12 50/50 medium. The samples are sterilized through 0.22 μm membranes and assayed in duplicate on C433 cells. The specific activity of OT-4 at this stage of the isolation is about 8 U/mg protein.

Figure 19:
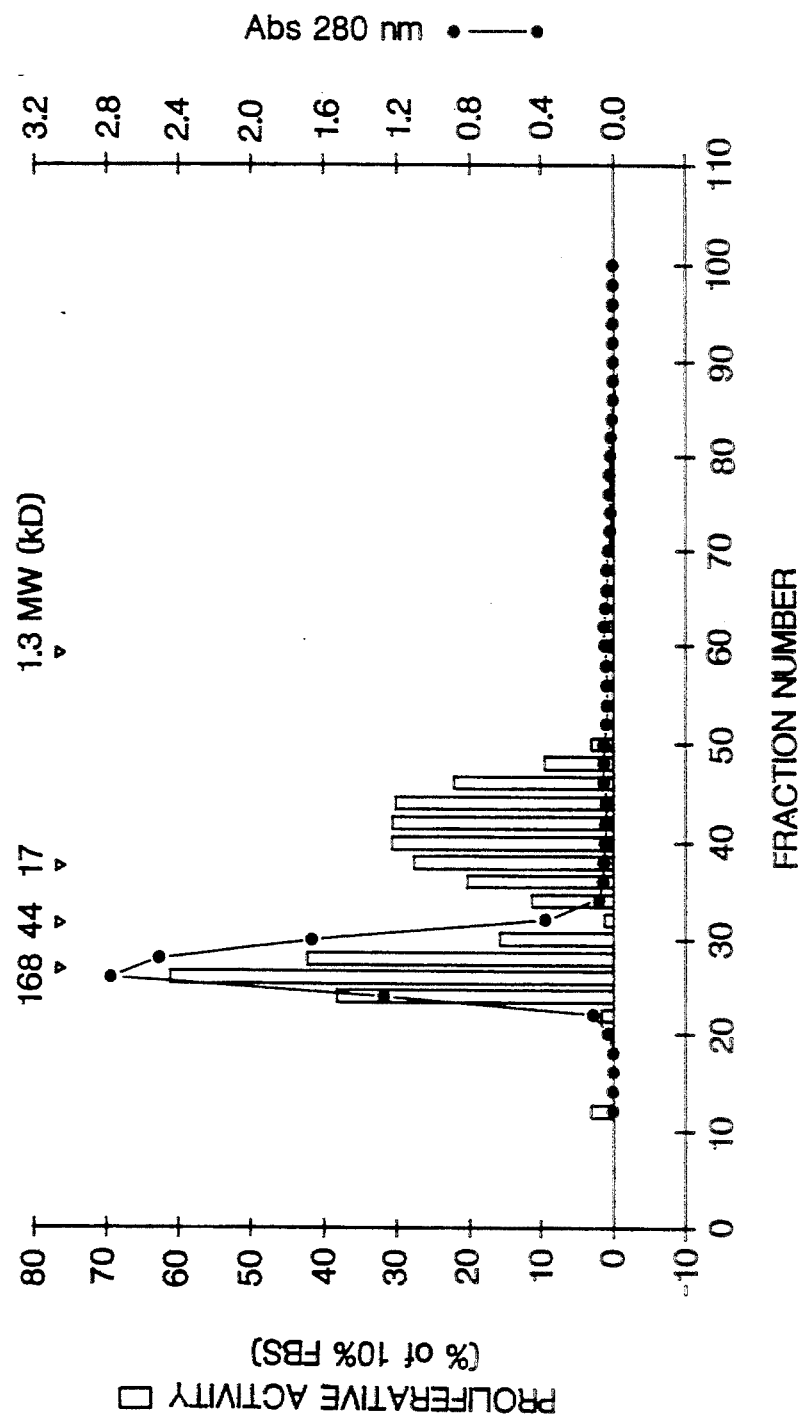
FIG. 19 describes the proliferative activity of OT-4 which migrated with fractions corresponding to MW of approximately 70,000 and approximately 6–7000 daltons after Sephacryl S100 chromatography.

FIG. 19 describes the elution profile from the Sephacryl S100 column and proliferative activity of eluted fractions. Two peaks having biological activity are observed; one having an apparent MW of 70 kD, and the second with a MW of approximately 6–7 kD.

Figure 20:
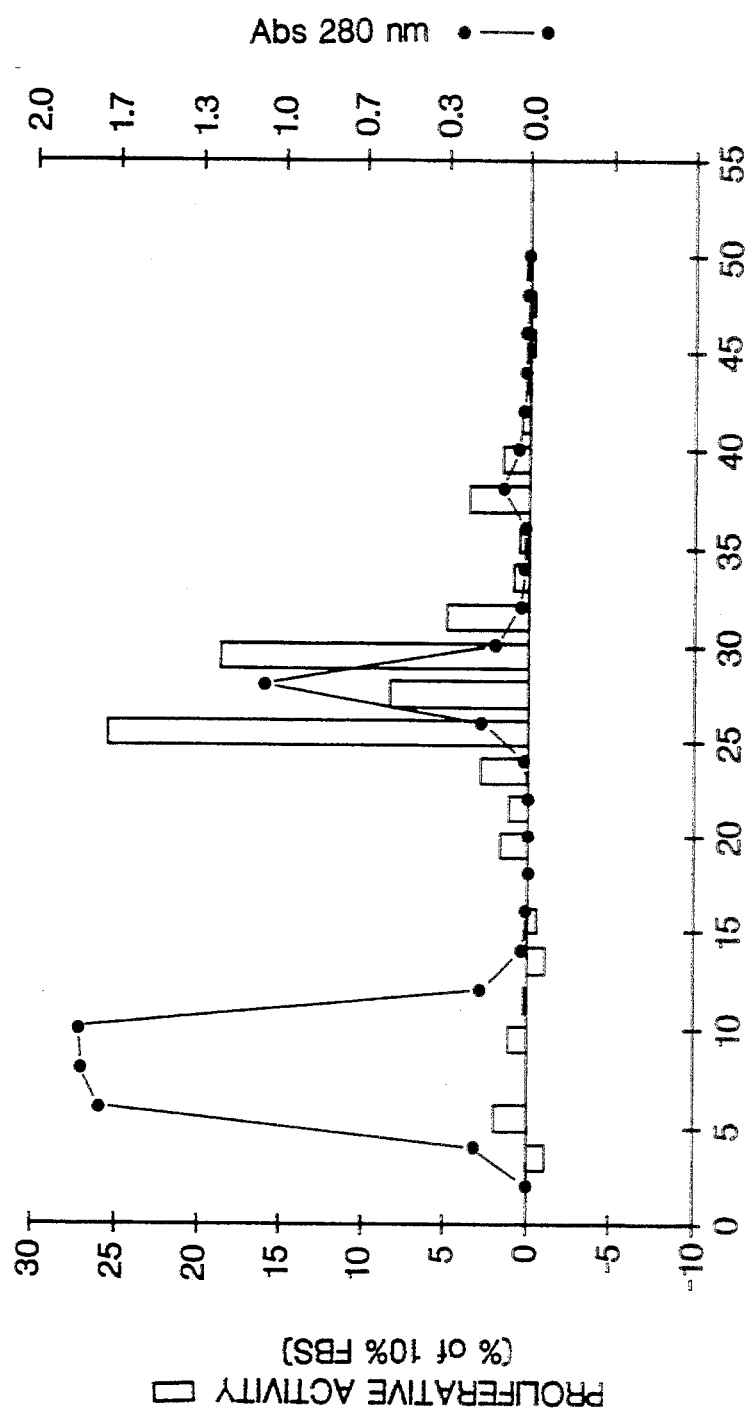
FIG. 20 describes the proliferative activity of the 6,000 dalton OT-4 after chromatography on SP Sephadex C50 column.

Fractions having an apparent molecular weight of 70 kD and exhibiting C433 proliferative activity are pooled and their protein content determined as 142 g, using absorbance readings at 280 and 260 nm with BSA as a standard. The sample is dialyzed against 1M acetic acid at a MW cut-off of 3.5 kD, and adjusted to 0.075M NaCl. This sample is subjected to cation exchange chromatography on a 2.5×8 cm SP Sephadex C50 column (Pharmacia LKB) equilibrated with 1M acetic acid, 0.075M NaCl pH 3.0. The sample is eluted with a 250 ml linear gradient from 1M acetic acid 0.075M NaCl pH 3.0 to 1M ammonium acetate 1.5M NaCl pH 9.0. Each fraction had a volume of 12.5 ml and its absorbance at 280 nm is measured. For the assay of proliferative activity, 400 μl of every 2 consecutive fractions are pooled with 88 μl of 1% BSA, dialyzed against PBS and DMEM/F 12 50/50 medium. After sterilization by filtration, the fractions are tested on C433 cells. The results are shown on FIG. 20. The specific activity of OT-4 at this stage of the isolation is 7.4 U/mg protein. The active fractions (26–32) eluting with the major bound protein peak are pooled, lyophilized, and redissolved in 90 ml of PBS and $H_2O$ to give a conductivity equal to that of 0.6M NaCl in PBS. The pH is adjusted to 7.4.

Figure 21:
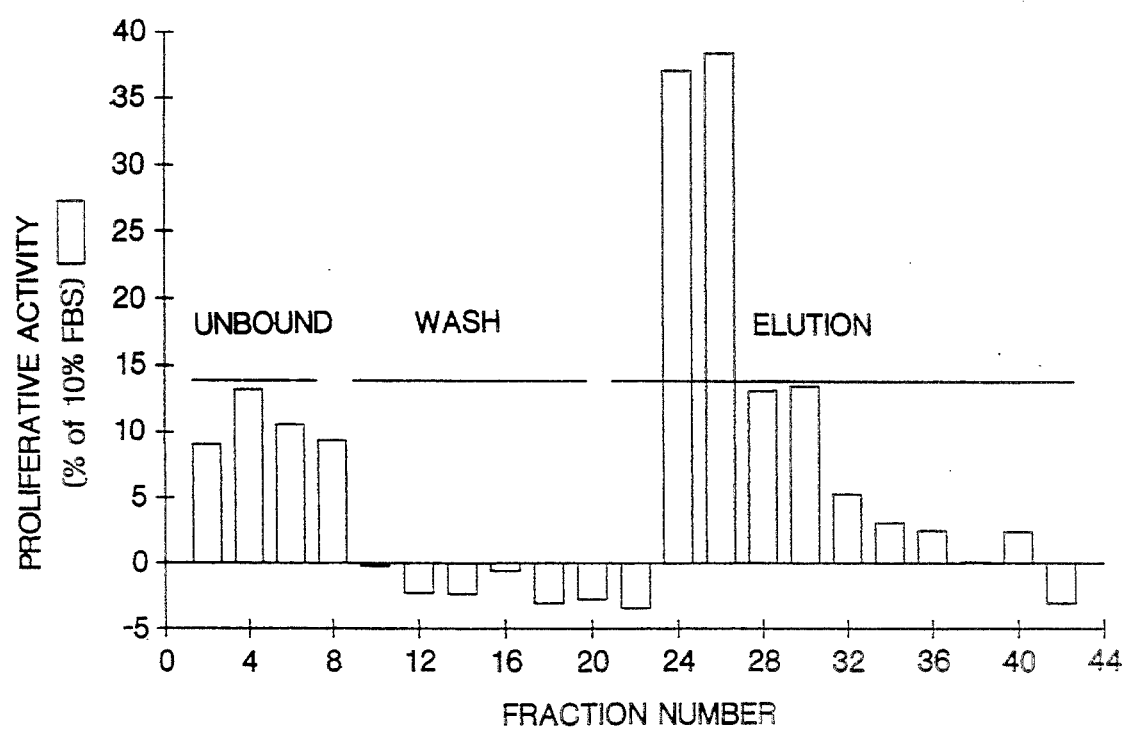
FIG. 21 describes the proliferative activity of the 6,000 dalton OT-4 after further chromatography on a IGF-BP3 affinity column.

The sample is applied to a 2 ml affinity column of amino link agarose (Pierce, Rockford, Ill.) carrying 0.66 mg of recombinant human IGF-binding protein 3 (IGF-BP3). The unbound material is washed out of the column with 16 ml of 0.6M NaCl PBS, and the bound material is eluted with 16 ml of 1M acetic acid pH 3.0. One ml fractions are collected. For the bioactivity assay 30 μl of every 2 consecutive fractions are pooled with 400 μl of 0.1% BSA and dialyzed against PBS and DMEM/F12 50/50 medium. After sterilization by filtration, the fractions are tested on C433 cells. The results are shown on FIG. 21. Proliferative activity for C433 cells is found predominantly in the bound fractions, although there is a small amount of activity in the unbound fractions, presumably because the column is overloaded.

Proliferative activity for C433 cells continued to be observed in both unbound and bound fractions after the unbound material is reapplied to affinity chromatography on the IGF-BP3 column a second and third time.

Figure 22:
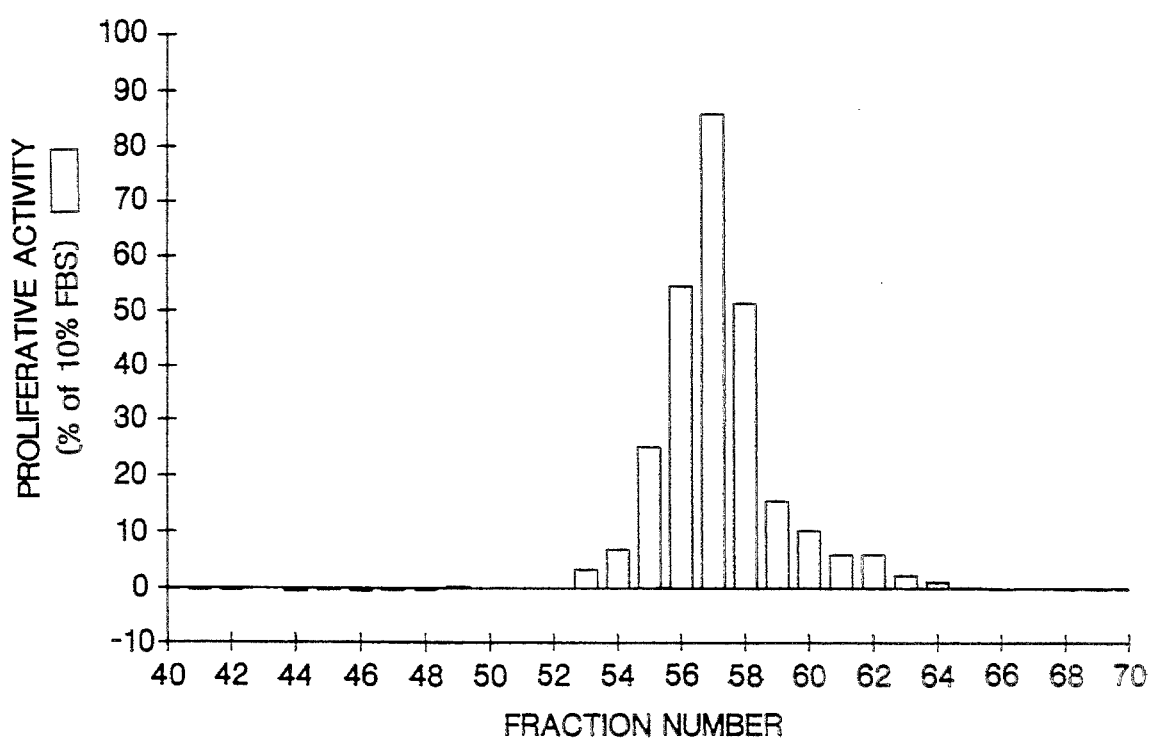
FIG. 22 describes the proliferative activity of the 6,000 dalton OT-4 after further chromatography on a C4 reverse phase HPLC column.
Figure 23:
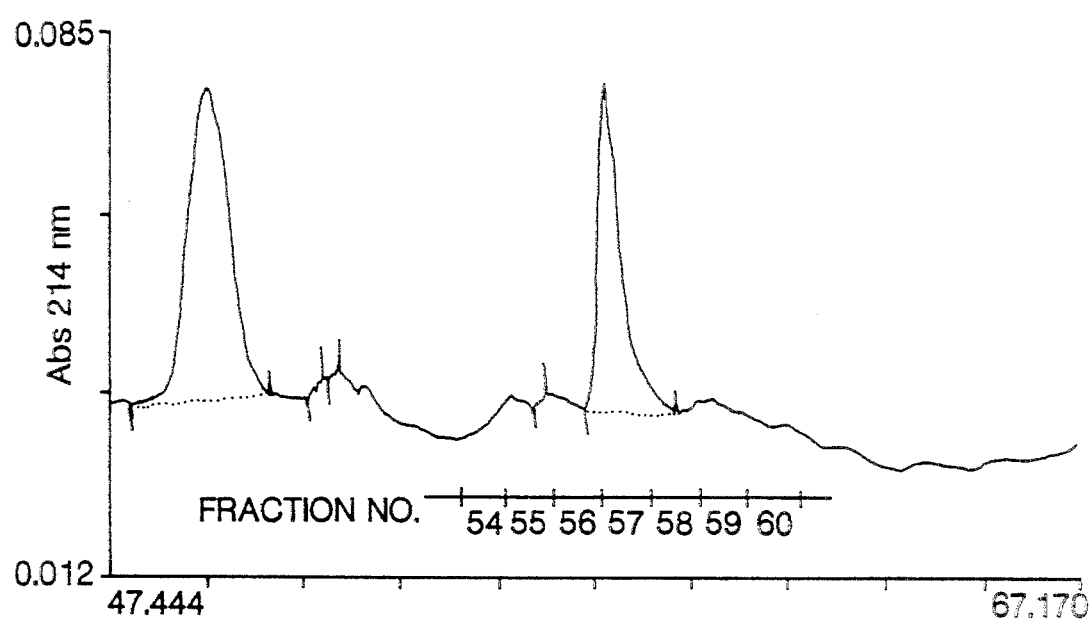
FIG. 23 describes the proliferative activity and absorbance profile of the 6,000 dalton OT-4 resulting from the fraction eluted in about 58 minutes after chromatography on a C4 reverse phase HPLC.

The bound fractions containing proliferative activity for C433, from the 3 consecutive affinity purification steps, are pooled, speed vacuum concentrated, made 0.1% in trifluoroacetic acid (TFA) (Pierce) and injected into a 2.1×150 mm C4 Vydac HPLC column (The Separation Group, Hespeda, Calif.) equilibrated with 7% acetonitrile (Bardick and Johnson, Muskegan, Mich.) 0.1% TFA in water. The HPLC apparatus is a System Gold by Beckman. The sample is eluted in 0.1% TFA by a gradient from 7 to 21% acetonitrile in 10 minutes, from 21 to 28% in 20 minutes, from 28 to 35% in 40 minutes and from 35 to 70% in 15 minutes. The flow is 0.150 ml/min, the absorbance at 214 nm is recorded, and 1 minute fractions are collected (FIG. 22). For the bioassay, 5 μl of each fraction are mixed with 250 μl 0.1% BSA, lyophilized, and redissolved in 250 μl of DMEM/F12 50/50 medium for assay on C433 cells. The specific activity of OT-4 at this stage of the isolation is $1.65 \times 10^6$ U/mg protein. The peak exhibiting biological activity elutes around 58 minutes at 31% acetonitrile (FIG. 23) and corresponds to a peak containing 600 μg of protein, estimated on the basis of a standard run of 1 μg of recombinant human TGFα.

Table 2 summarizes the purification procedure used to isolate and purify OT-4. Activity recovery is calculated as a percentage of the amount of total activity recovered after heparin Sepharose chromatography.

TABLE 2

| | Summary of Purification of Antlerin-4 | | | | |
|---|---|---|---|---|---|
| Chromatographic Step | Total protein (mg) | Total activity (U) | Specific activity (U/mg protein) | Activity recovery (%) | Fold purification (X) |
| Heparin-Sepharose | $335 \times 10^3$ | $1.3 \times 10^6$ | 3.9 | — | — |
| S100 Sephacryl | $142 \times 10^3$ | $1.2 \times 10^6$ | 8.5 | 92 | 2.2 |
| SP Sephadex | $54 \times 10^3$ | $4 \times 10^5$ | 7.4 | 31 | 1.9 |
| IGF-BP3 Affinity Column | — | $2.2 \times 10^6$ | — | 169 | — |
| C4RP HPLC | 0.6 | $9.9 \times 10^5$ | $1.6 \times 10^6$ | 76 | $4.1 \times 10^5$ |

*100 units represents the equivalent proliferative activity of 10% FBS

This active protein material is applied to a gas-phase microsequencer, and the sequence of the first 17 amino acids determined. This sequence is similar but distinct from that of human, bovine, deer, porcine, ovine and rat IGF-II, which are all identical in their first 19 residues. The sequence of this proteinaceous growth factor, referred to herein as OT-4, is given below, and compared with that of human IGF-II. In addition to the differences in the amino acid sequences between OT-4 and human IGF-II, antibodies which recognize OT-4, do not recognize IGF-I or IGF-II.

| | 1 | 2 | 3 | 4 | 5 | 6 | 7 | 8 | 9 | 10 |
|---|---|---|---|---|---|---|---|---|---|---|
| OT-4 [SEQ ID NO: 3] | A | Y | I | P | I | E | T | L | E | G |
| hIGF-II [SEQ ID NO: 4] | A | Y | R | P | S | E | T | L | C | G |

| | 11 | 12 | 13 | 14 | 15 | 16 | 17 | 18 | 19 |
|---|---|---|---|---|---|---|---|---|---|
| OT-4 | I/G | E | L | V | D/Q | T | G/L | Q | F |
| hIGF-II | G | E | L | V | D | T | L | Q | F |

EXAMPLE 7

Preparation of Monoclonal Antibodies to OT

Monoclonal antibodies (MAb) to OT are prepared by an in vitro immunization technique (Van Ness et al, 1983, Nature 301: 425–427). Spleen cells of 8 to 12 week-old female Balb/C mice are immunized with 250 pg synthetic 14-mer peptide of OT-2 in the presence of 100 mg N-acetylmuramyl-L-alanyl-D-isoglutamine (MDP, Sigma), 125 mg lipopolysaccharide (LPS, Difco) and 500 μl culture supernatants of concanavalin A (50 mg/ml)-stimulated spleen cells ($5 \times 10^6$/ml) in 5 ml IMDM supplemented with 20% FBS in 6-well plates for 4 days. The immunized spleen cells are then hybridized with mouse myeloma FO cells (kindly provided by Dr. Eguchi, Kaneka, Japan) at a ratio of 2:1 in the presence of 50% polyethylene glycol (1500, Boehringer-Manheim). After the hybridization, the cells are suspended in 120 ml IMDM supplemented with 10% FBS and 0.5 ml cell suspension are inoculated into each well in 48-well plates. After 24 hours, $5 \times 10^5$/well thymocytes in 0.5 ml HAT medium are plated onto each well as a feeder layer. The plates are cultured for 14 days in HAT medium (Flow) and then for 7 to 10 days in HT medium (Flow). The cells are fed fresh medium every 2 days. The culture supernatants, harvested from the wells in which growing hybddoma cells cover 50% of the surface area, are screened for their crossreactivity with the synthetic or 14-mer peptide (OT-2) by enzyme-linked immunosorbent assay (ELISA). The hybridoma produces monoclonal antibodies designated MAbOT-2 which recognizes OT-2 polypeptide but not IGF-I or IGF-II. The same procedure is followed to obtain a hybridoma producing monoclonal antibody which recognized OT-4.

EXAMPLE 8

Polyclonal Antibodies to OT

Rabbits (male, 6 to 8 week-old) are subcutaneously injected (10 sites/animal, 100 μl/site) with 1.3 mg keyhole limpet hemocyanin (KLH)-conjugated synthetic 11-mer peptide of OT-4 or 14-mer peptide of OT-2 and 2 ml complete Freund's adjuvant. Four weeks after the first immunization, animals are boosted intramuscularly with 1.3 mg KLH-conjugated synthetic 11-mer or 14-mer peptide and 2 ml incomplete Freund's adjuvant 3 times. At each booster, blood is drawn from an ear vein and tested for its titer against the synthetic 11-mer or 14-mer peptide by ELISA.

EXAMPLE 9

OT Assays

A. OT Enzyme-Linked Immunosorbent Assay (ELISA)

The ELISA of OT-2 and OT-4 is performed as follows:

ELISA plates (Falcon) are coated with 50 ng/50 µl/well synthetic 11-mer peptide of OT-4 or 14-mer peptide of OT-2 overnight at 4° C. The wells are washed with 200 µl/well phosphate-buffered saline (PBS) twice, incubated with 200 µl/well blocking buffer (1% bovine serum albumin in PBS) for 1 hour at 37° C. and rinsed with 250 µl washing buffer (0.05% Tween 20 in PBS). The plates are then incubated with 200 µl/well of 1/1000 dilution of polyclonal antibody or hybridoma supernatants to be tested overnight at 4° C. and rinsed with 250 µl/well washing buffer 3 times. After rinsing, the plates are incubated with 200 µl/well peroxidase-conjugated goat anti-rabbit immunoglobulin G antibodies for 1 hour at 37° C., rinsed with 250 µl/well washing buffer 5 times and incubated with 200 µl/well o-phenylenediamine dihydrochloride (OPD) solution (4 mg OPD and 10 µl 30% hydrogen peroxide in 10 ml water) for 10 to 20 minutes. The absorbance is read at 450 nm after 10 minutes and 20 minutes.

The results of a representative ELISA are shown on Table 3.

TABLE 3

| Con- | ELISA Assays for both OT-2 and OT-4 | | | |
|---|---|---|---|---|
| | Polyclonal AB to OT-2 | | Polyclonal AB to OT04 | |
| centration (ng/ml) | OT-2 $OD_{450}$ | IGF-I $OD_{450}$ | OT-4 $OD_{450}$ | IGF-II $OD_{450}$ |
| 1000 | 0.870 | 0.031 | 0.341 | 0.001 |
| 500 | 0.825 | 0.025 | 0.351 | 0.002 |
| 250 | 0.725 | 0.032 | 0.338 | 0.005 |
| 125 | 0.770 | 0.012 | 0.310 | 0.001 |
| 62.5 | 0.651 | 0.054 | 0.307 | 0.001 |
| 31.2 | 0.546 | 0.030 | 0.270 | 0.002 |
| 15.6 | 0.405 | 0.021 | 0.195 | 0.005 |
| 7.3 | 0.186 | 0.041 | 0.122 | 0.006 |
| 3.5 | 0.104 | 0.022 | 0.069 | 0.002 |
| 1.7 | 0.063 | 0.025 | 0.019 | 0.001 |
| 0.9 | 0.042 | 0.021 | 0.006 | 0.002 |

Antibodies directed to the OT-2 14 mer peptide or the OT-4 11-mer peptide do not cross react with either human IGF-I or II when tested in the ELISA assay.

B. OT-2 Radioimmunoassay (RIA)

The radioimmunoassay for OT-2 is performed in glass tubes by incubating 500 µl of the sample buffer containing 0.15M NaCl, 0.05M Tris, 2 mM EDTA and 2mg/ml gelatin at a pH of 7.5 in the presence or absence of unlabelled OT-2 with 100 µl of antibody solution containing 2.5 µl of the polyclonal antibody to OT-2, 25 µl of normal rabbit serum and 100 µl of sample buffer. After 24 hours of incubation at 4° C., 100 µl of sample buffer containing 20,000cpm of OT-2 conjugated to bovine serum albumin and labelled with $^{125}I$ is added and further incubated overnight at 4° C. One ml of the precipitating antibody solution containing 0.15M PBS with 5% polyethylene glycol and 12 µl of goat anti-rabbit antibody is added and is incubated for 1 hr at room temperature. The tubes are then centrifuged at 3000rpm at 4° C. for 30min. The supernatant is removed and the tubes are then capped and counted in a multichannel gamma counter. The competition of unlabelled OT-2 peptide is determined. The assay sensitivity is 1 ng/ml for the unlabelled peptide. As the data shown on Table 4 demonstrate, neither IGF-I nor IGF-II compete for the antibody to OT-2.

TABLE 4

| Competitive Radioimmunoassay for OT-2* | | |
|---|---|---|
| Concentration (ng/ml) | OT-2 precipitated cpm | IGF-I precipitated cpm |
| 0 | 2406 | 2406 |
| 0.010 | 2528 | 2359 |
| 0.060 | 2423 | 2458 |
| 0.30 | 2057 | 2589 |
| 1.6 | 1888 | 2456 |
| 8 | 1565 | 2508 |
| 40 | 1189 | 2470 |
| 200 | 1000 | 2368 |

*The assay was with $I^{125}$ labeled BSA congugated OT-2 and using the polyclonal antibody to OT-2

EXAMPLE 10

Technique for Testing Effects of Crude Antler Extract on Bone Growth

The short term effects of proteinaceous factor material extracted from antler are tested in ICR Swiss white mice, aged 4–6 weeks and weighing 13–26 gms using 4 mice per group. 200 mls of a soluable EDTA extract is prepared from antlers as described in Example 3. This material is extensively dialyzed against water then lyophilized to powder. Alternatively, 500 gms (wet weight) of deer antler (equivalent to one-half of an antler) which had been demineralized as described in Example 3 is defatted with a 1:1 chloroform/methanol solution. This material is then dried to a weight of 192 gms. The 192 gms of dried deer antler material is extracted with 4M urea with 0.5M $CaCl_2$, 0.1% sodium azide and NEM for 48 hrs. at room temperature in a volume 19–20 ml. The pelleted material which is not extracted is removed by centrifugation. The urea extract is dialyzed against 23 volumes of distilled water at 4° C. overnight after which a water insoluble precipitate extract is formed. This precipitate is then removed by centrifugation 40,000×g for 30 min. at 25° C. The precipitate is washed with 3×500 ml of $dH_2O$. Both the water insoluble precipitate and the water soluble extract are then lyophilized. 9.8 gms of the water insoluble urea extract and 6.2 gms of water soluble urea extract are obtained. The water insoluble fraction is tested for biological activity in vivo as described below.

A 25 mg/ml suspension of either water insoluble urea extract or EDTA soluble extract is made up in phosphate buffered saline and 40 µl/20 gm body weight (representing a dose of 50 mg/Kg body weight) of this material is injected over the calvaria of 5 week old mice once a day for 3 days. As a control 40 µl of a 25 mg/ml bovine serum albumin solution is injected over 5 week old mice once a day for 3 days. Four mice are taken at 7, 14, and 21 days after the initial injection and the calvaria removed. After fixation in 10% phosphate buffered formalin, the intact calvaria are decalcified in 14% EDTA. The occipital bone is then removed by cutting immediately behind and parallel to the lambdoid suture, and the frontal bone is removed by cutting anterior to the coronal suture using a scalpel blade. The bones are then bisected through the coronal plane and 3–4 mm strips of bone are dehydrated in graded alcohols, and embedded in paraffin. Five µm sections are then cut from each specimen and stained with hematoxylin and eosin.

Figure 24:
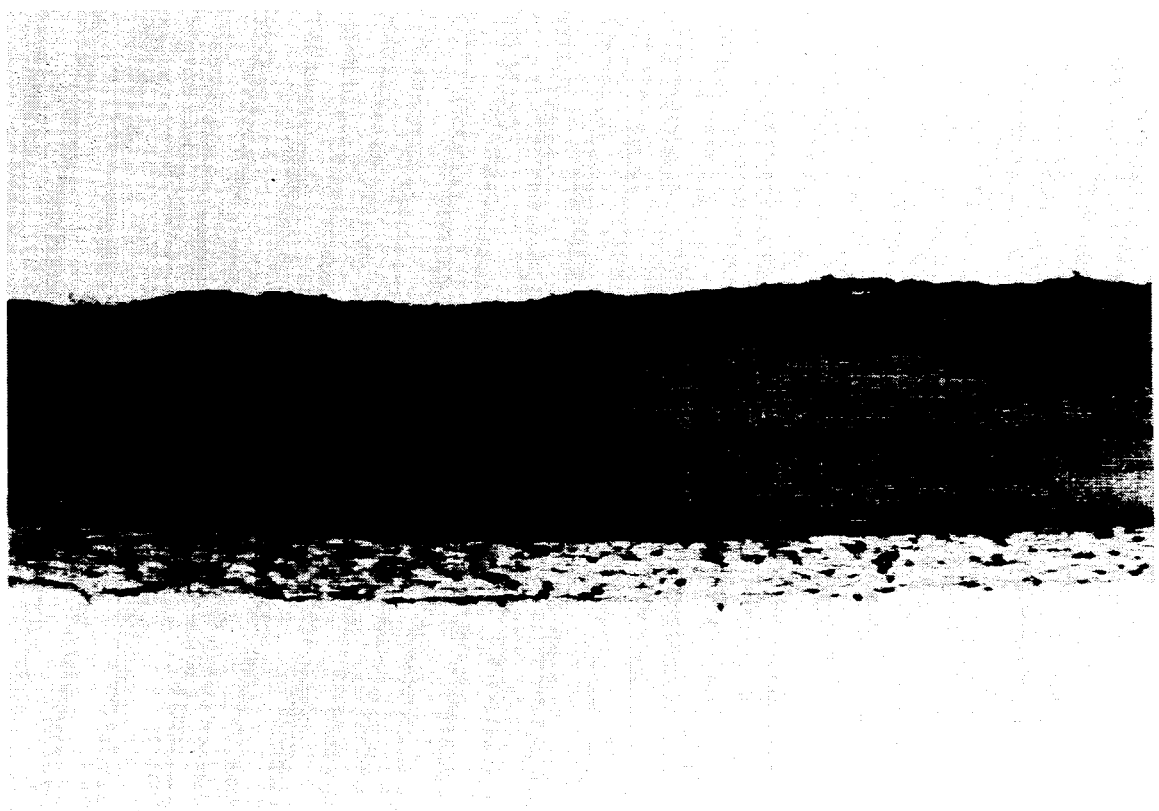
FIG. 24 describes the effect of injecting 40 $\mu$l of a 25 mg/ml solution of bovine serum albumin once a day for 7 days over the calvaria of 5 week old mice.
Figure 25:
FIG. 25 describes the effect of injecting 40 $\mu$l of a 25 mg/ml suspension of the water insoluble urea soluble deer antler extract once a day for 7 days over the calvaria of 5 week old mice.

Calvaria from animals which are injected with BSA have few or no changes compared to non-treated controls (FIG. 24). In mice treated with EDTA soluble or water insoluble urea extracted deer antler material, there is substantial new woven bone growth seen on the outer surface of the calvarial bone by day 7 (FIG. 25). By days 14 and 21 this new bone has the appearance of lameliar bone. These results show that proteinaceous material extracted from antler tissue are capable of promoting the formation of new lameliar bone. These extracts could be used therapeutically for the enhancement of bone growth and fracture repair in animals. Preferably, this antler extract can be used therapeutically to treat pathological bone conditions in mammals such as dogs, cats, horses, sheep, as well as humans.

EXAMPLE 11

Purification of Antlerin-2 Polyclonal Antibodies using Affinity Chromatography

The synthetic OT-2 14-mer peptide and OT-4 11-mer peptides are synthesized using F-MOC chemistry. Cysteine is added to the C-terminal end of half of the material. The C-terminal end is coupled through the sulfhydryl group to an affinity column. Once this peptide affinity column is made, 90 mls of rabbit serum containing polyclonal antibody to the 14-mer peptide of OT-2 or to the 11-mer peptide of OT-4 is ammonium sulphate precipitated, dialysed, and subjected to the peptide affinity column. The column is eluted with 0.1M glycine (pH 2.8) and approximately 9 mg of OT-2 purified antibody or approximately 2 mg of OT-4 antibody are retrieved. Both antibodies are solubilized to a concentration of 100 µg/ml and the titre of these antibody preparations is 1/10000 for OT-2 and 1/5000 for OT-4.

EXAMPLE 12

Affinity Purification of Antlerin-2 (OT-2).

The purified OT-2 antibody prepared as in Example 11 is coupled through an amino group to a second affinity matrix. The binding of the antibody to the column is greater than 4 mg. One ml of deer antler extract is processed through this antibody affinity column and no activity is present in the flow-through fraction. The bound fraction is eluted with 0.1M glycine. ELISA assay of the eluants indicates immunoreactive material eluting from the column.

EXAMPLE 13

Isolation of IGF-I from Deer Antler Tissue

Figure 26:
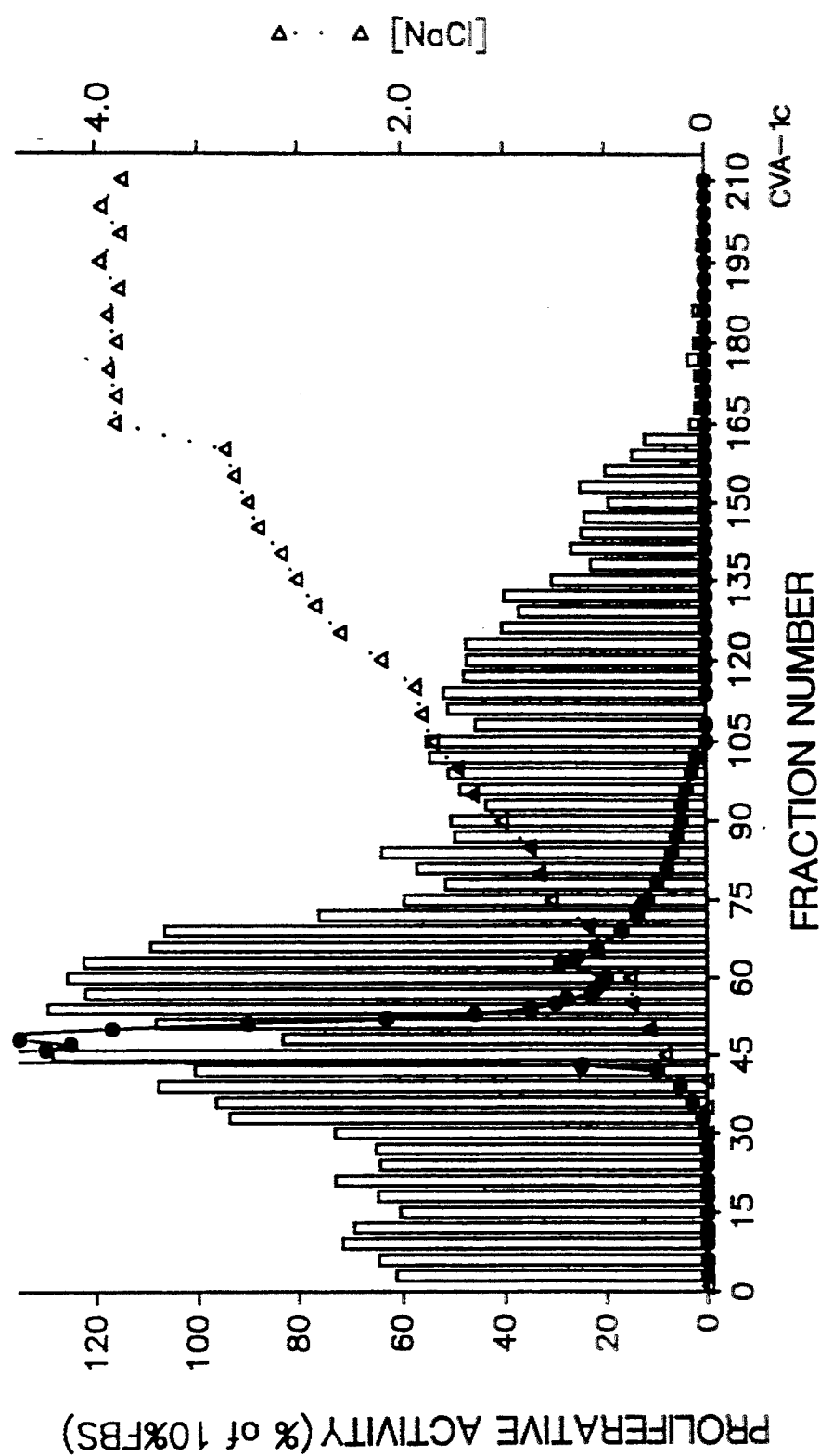
FIG. 26 describes the heparin Sepharose chromatography elution profiles of IGF-I and proliferative activity of EDTA-extracted antler preparations on C433 cells.
Figure 27:
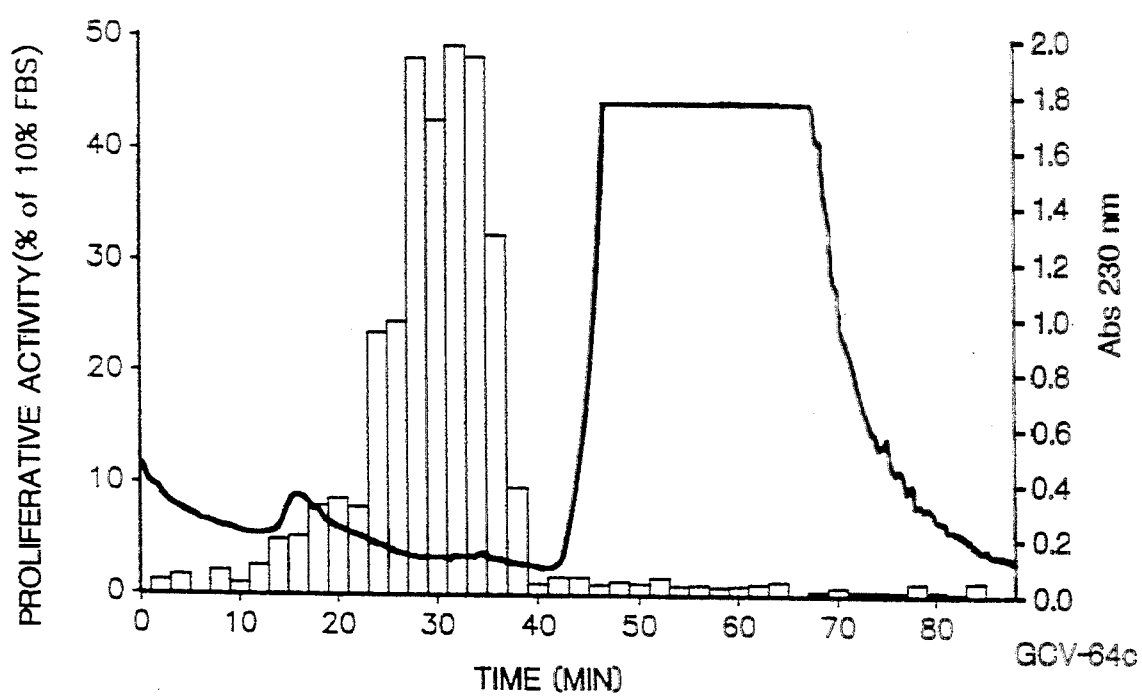
FIG. 27 describes the proliferative activity of IGF-I on C433 cells after Synchropak AX-300. This figure is representative of five other column runs either on AX-300 or DEAE Sephacel.
Figure 28:
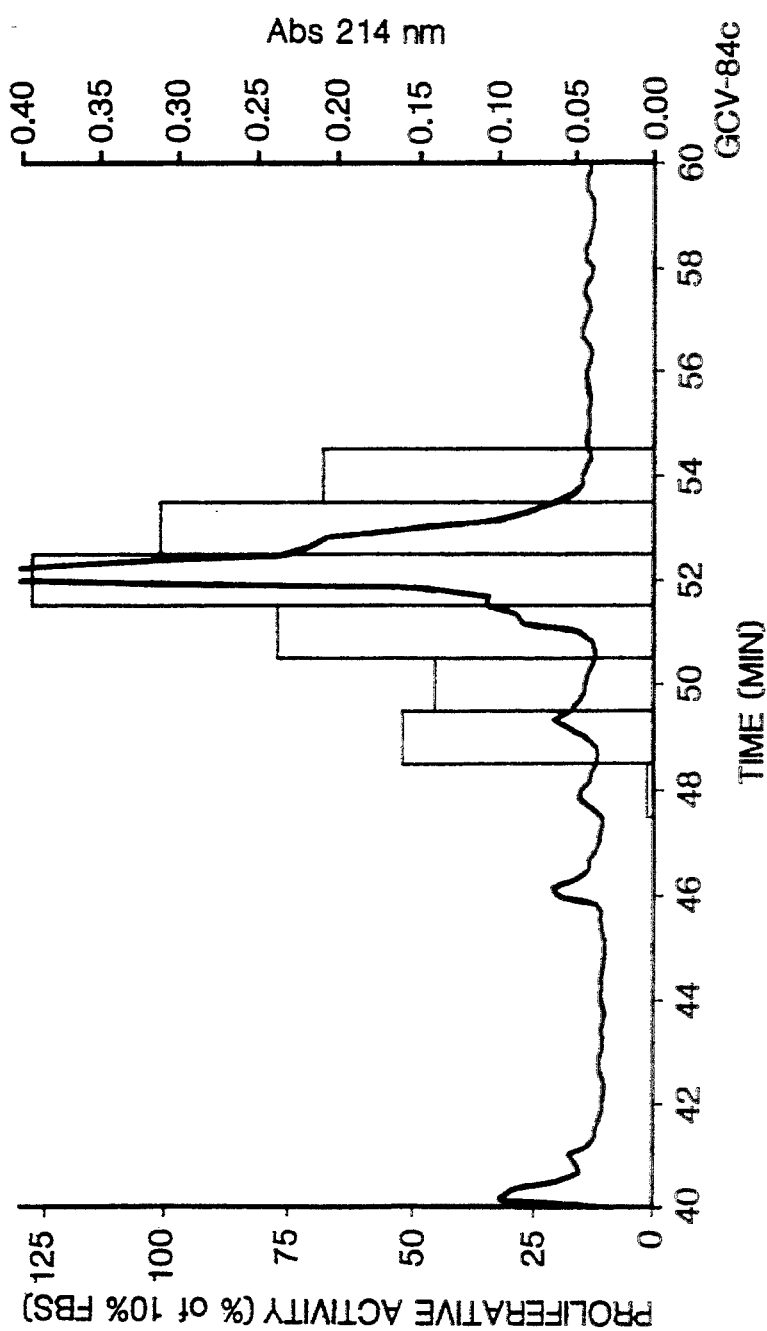
FIG. 28 describes the proliferative activity of IGF-I on C433 cells after chromatography on a C4 reverse phase HPLC column.
Figure 29:
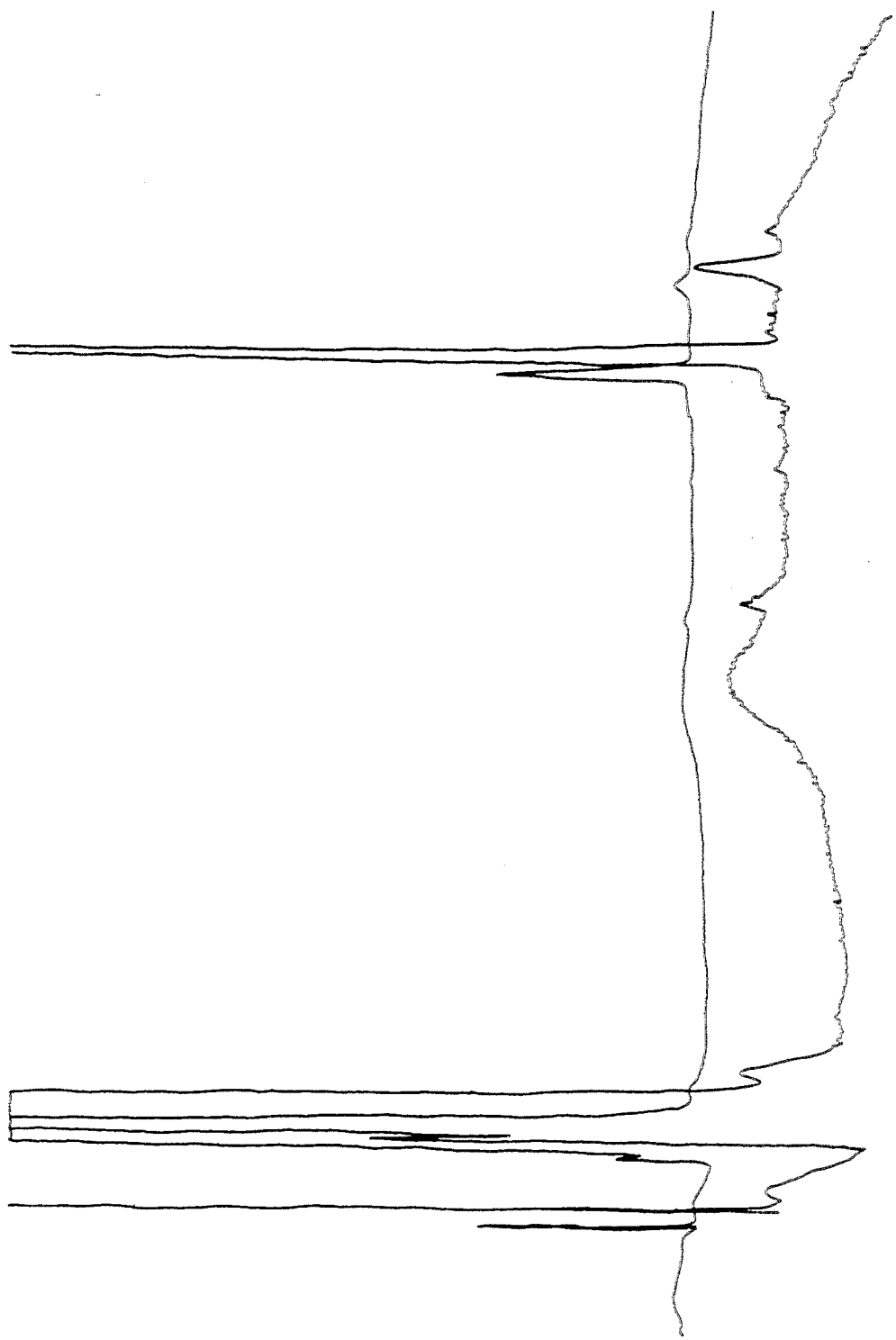
FIG. 29 describes the absorbance profile of IGF-I after chromatography on a C8 reverse phase HPLC column of fraction 52 shown in FIG. 28.

A soluble EDTA extract is prepared from antlers as described in Example 3 and chromatographed on a heparin Sepharose column as described in Example 3A. The unbound material is rechromatographed on the same column. Material exhibiting C433 proliferative activity which remains unbound or is eluted from the heparin Sepharose column at low salt concentration (<0.4M NaCl) (FIG. 26) are subjected to anion-exchange chromatography either on AX-300 Syncropak or DEAE Sephacel. Material exhibiting C433 proliferative activity which bound to these columns and is eluted at NaCl concentrations between 0.3–0.4M is pooled (FIG. 27) (6 separate column runs) and pooled material is dialyzed against 0.1M PBS containing additionally 0.6M NaCl, pH 7.6 (PBS/NaCl). After dialysis, the sample is applied to a 2 ml affinity column of amino link agarose (Pierce, Rockford, Ill.) to which is bound 0.66 mg of recombinant human IGF-binding protein 3 (IGF-BP3). The unbound material is washed out of the column with 16 ml of PBS/NaCl, and the bound material is eluted with 16 ml of 1M acetic acid, pH 3.0. One ml fractions are collected. Material exhibiting proliferative activity for C433 cells bound to the affinity column. Bound fractions with activity are speed-vacuum concentrated, reconstituted in 0.1% TFA and injected into reverse phase HPLC using a $C_{18}$ column (10×250 cm) with a gradient of 0.1% TFA and 0.1% TFA/70% acetonitrile at a flow rate of 2 ml/min. Absorbance is monitored at 220 nm. Biological activity in C433 cells is determined from an aliquot of each fraction (FIG. 28). The fraction eluting at 32% acetonitrile (52 minutes) is applied to a C8 RPH PLC (FIG. 29). The partial amino acid sequence of the peak eluting at 30% acetonitrile is determined. This fraction is applied to a pulsed liquid microsequencer and the amino acid sequence determined by the sequencer is identical to that of human IGF-I.

IGF-I [SEQ ID NO: 5]
GPETLCGAEL VDALQFVCGD
RGFYFNKPTG YGSSSRKAPQ
TGIVDECCFR SCDLRRLEMY CAPLKPAKSA

EXAMPLE 14

Isolation of IGF-II from Deer Serum

Figure 30:
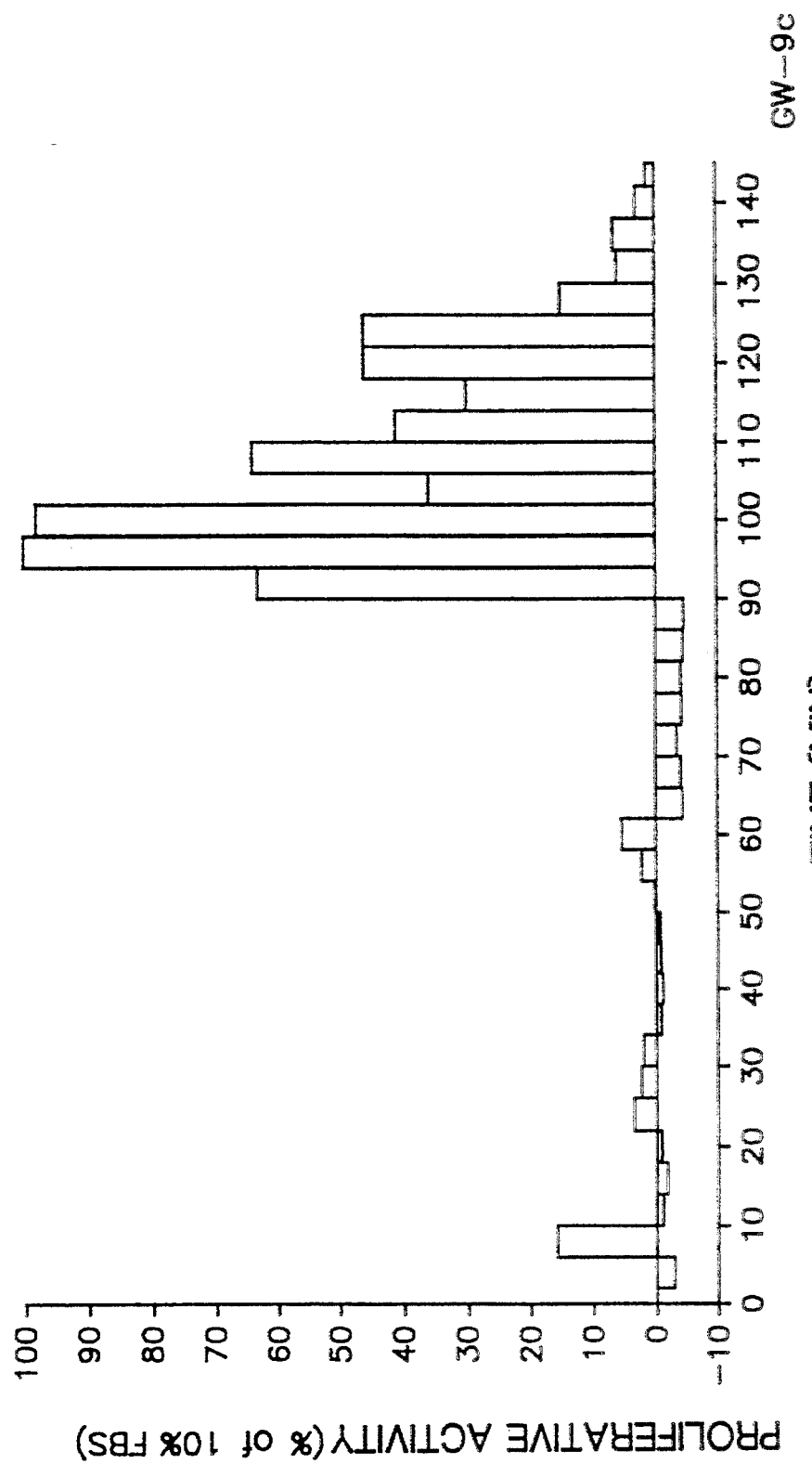
FIG. 30 describes the SP-Sephadex C50 elution profiles of deer IGF-II and proliferative activity of acid-treated deer antler serum on C433 cells.
Figure 31:
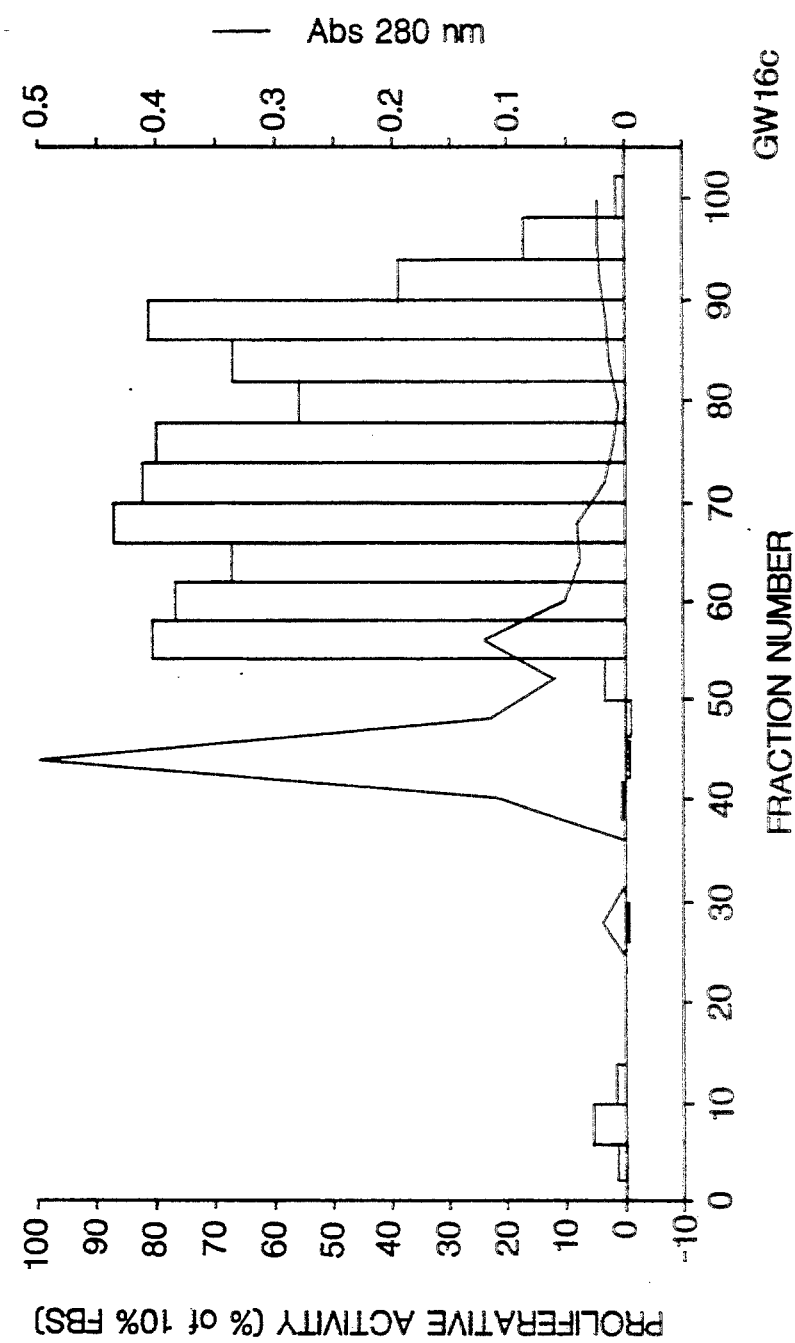
FIG. 31 describes the proliferative activity of deer IGF-II on C433 cells after Sephacryl S100 chromatography.
Figure 32:
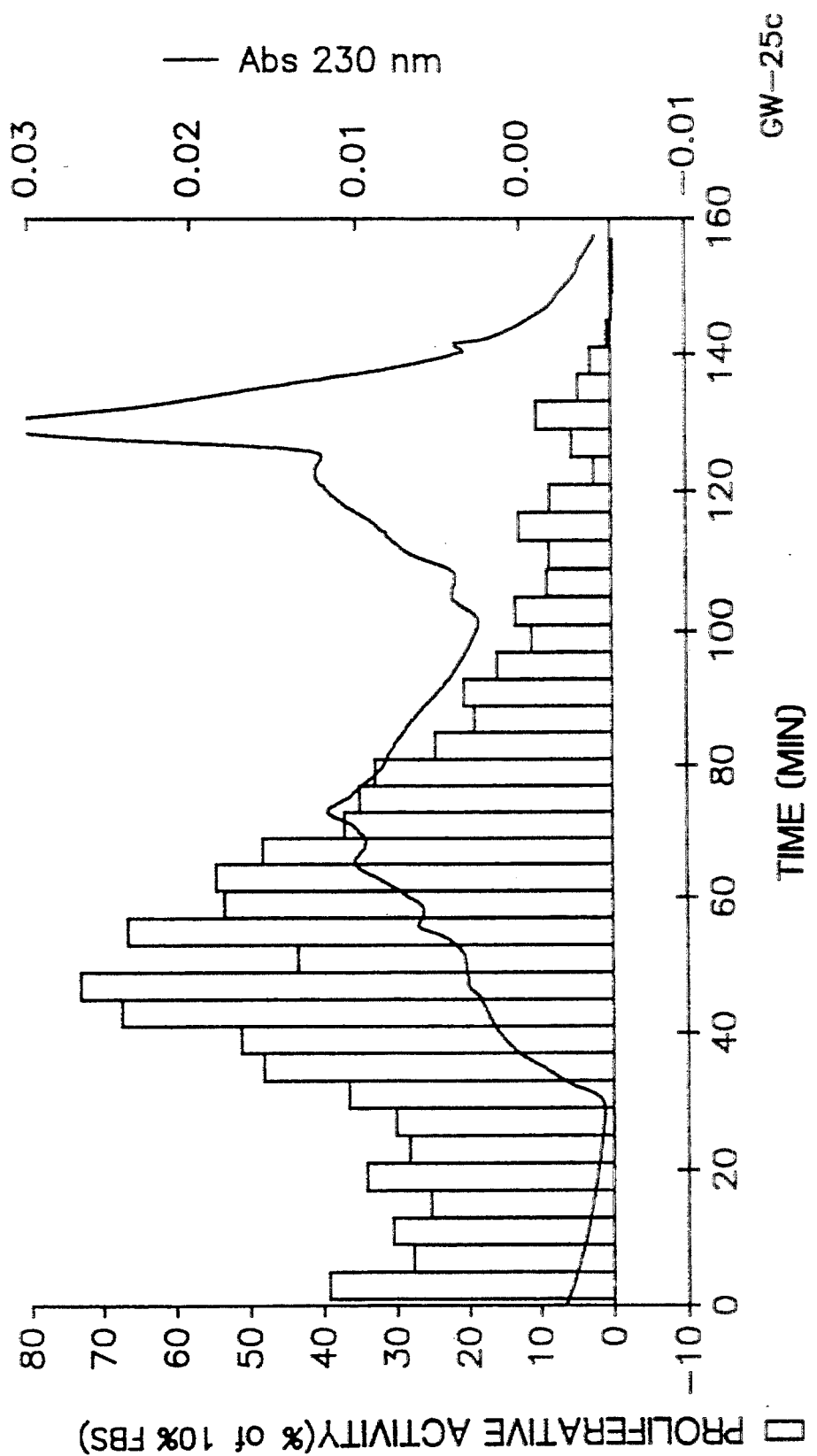
FIG. 32 describes the proliferative activity of deer IGF-II on C433 cells after Synchropak AX-300 chromatography.
Figure 33:
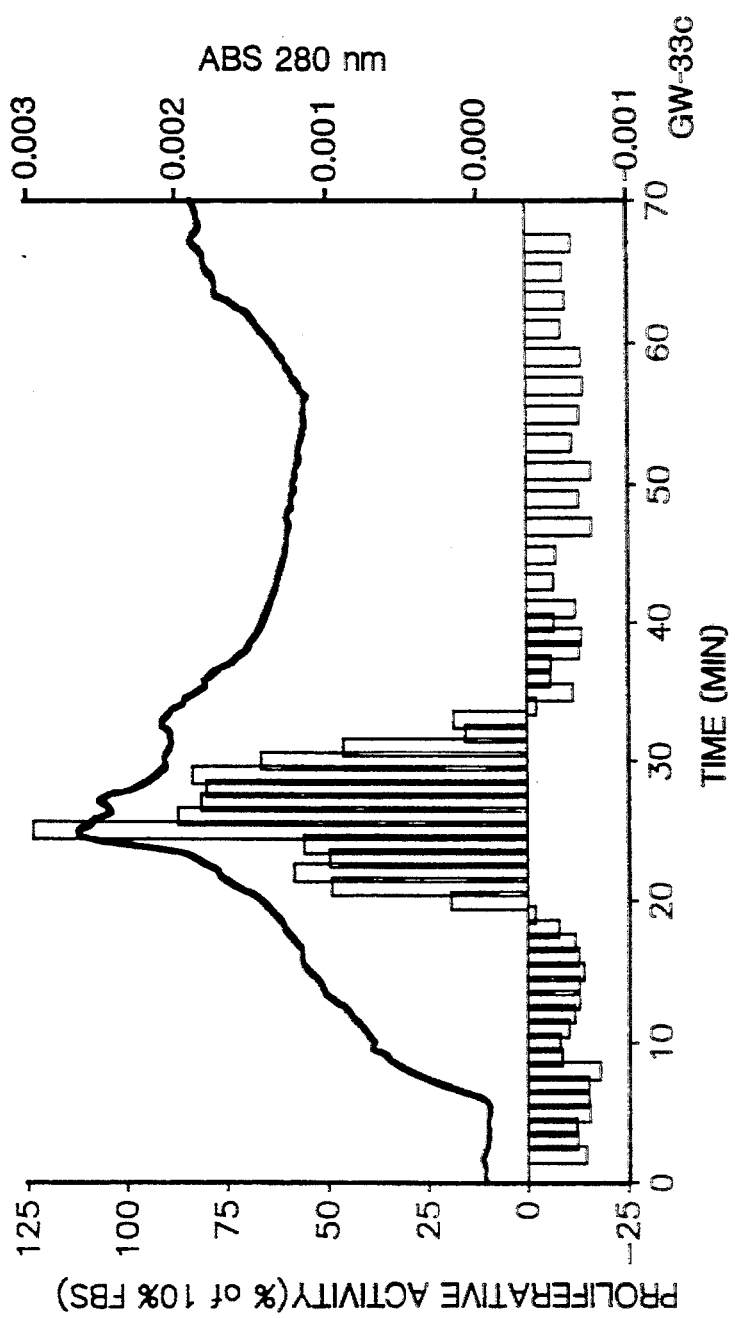
FIG. 33 describes the proliferative activity of deer IGF-II on C433 cells after chromatography on Mono-S FPLC column.
Figure 34:
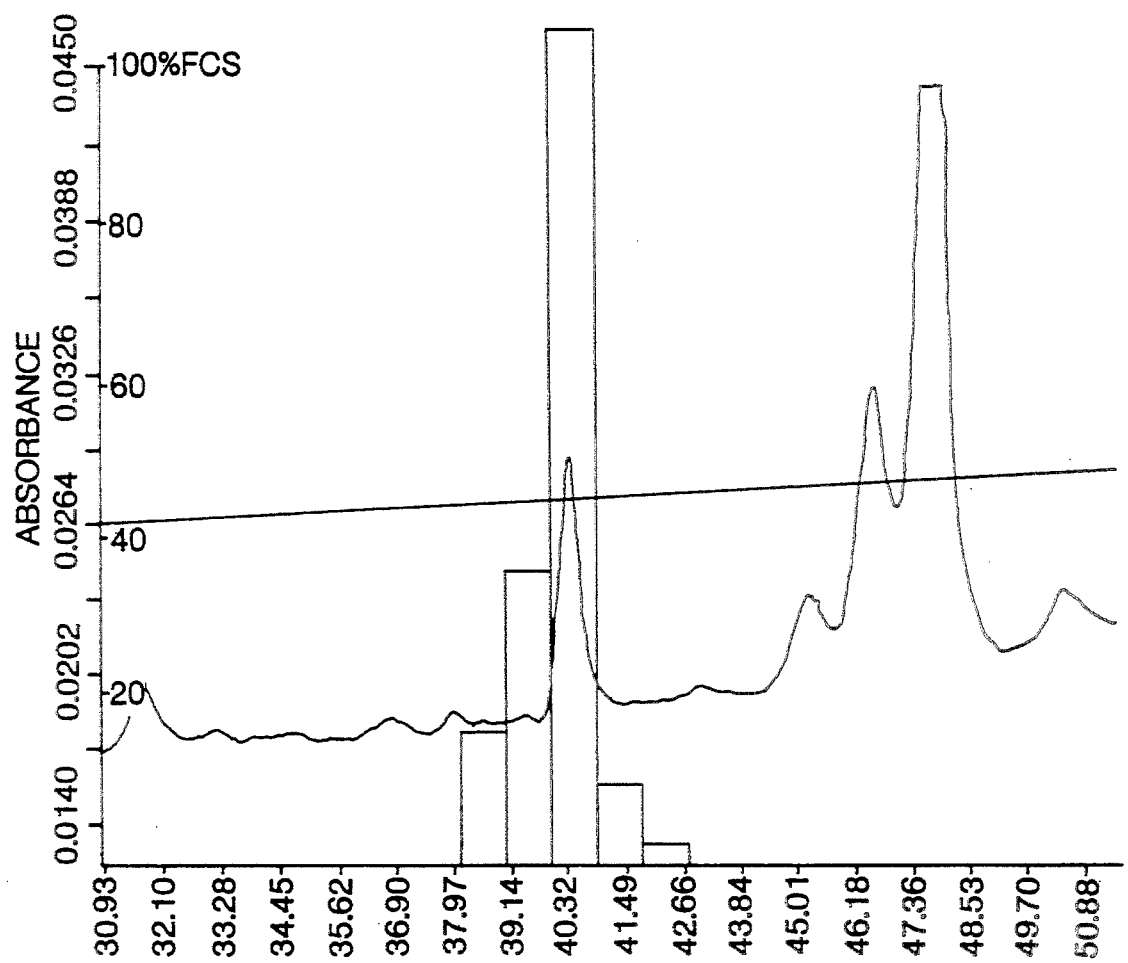
FIG. 34 describes the proliferative activity of deer IGF-II on C433 cells and absorbance profile after chromatography on a C18 reverse phase HPLC column.

Forty-five ml of deer antler serum collected during the antler growing season is dialyzed overnight against 1M acetic acid, 75 mM NaCl (pH 3). The dialyzate is applied to a 2.5×21 cm SP-Sephadex column, equilibrated with 1M acetic acid, 75 mM NaCl. Gradient elution is performed from the starting conditions to 2M NaCl, pH 9. Ten ml fractions are collected. To determine proliferative activity in C433 cells, 100 µl of 4 consecutive fractions are pooled, 0.1% BSA added and the pooled sample is dialyzed against PBS and DMEM/F12 50/50 medium. After sterilization by filtration through a 0.2 µm membrane, fractions are tested in C433 cells (FIG. 30). Active fractions eluting at 1.5M NaCl, pH 9, are pooled, dialyzed against 1M acetic acid and applied to a 2.5×120 cm Sephacryl S-100 column using the same initial buffer. Six ml fractions are collected and 125 µl of 4 consecutive fractions with 0.1% BSA are dialyzed against PBS and DMEM/F12 medium to determine proliferative activity (FIG. 31). Fractions eluting around 14 kDa from S-100 column are pooled, lyophilized, reconstituted in 20 mM Phosphate monobase pH 8.0 and applied to 1×25 cm Synchropak AX-300 column. Two ml fractions are collected and 100 µl of every 2 consecutive fractions with 0.1% BSA are pooled, dialyzed and tested for biological activity (FIG. 32). Fractions eluting at 0.5M NaCl from AX-300 column, are pooled, dialyzed against 10 mM ammonium acetate pH 4.8 and applied to a 0.5×5 cm FPLC Mono-S column (LKB Pharmacia). Elution is performed using a linear gradient from 10 mM to 1M ammonium acetate in 10% acetonitrile. Absorbance is recorded at 280 nm. One ml fractions are collected and C433 activity determined using an aliquot of each fraction (FIG. 33). Active fractions eluting at 0.35M ammonium acetate from Mono-S are speed-vacuum concentrated and applied to RPHPLC C18 4.6×150 mm Vydac column using acetonitrile/TFA gradient. Flow rate is 0.7 ml/min and absorbance is recorded at 214 nm. Seven hundred µl fractions are collected and 6 μl per fraction are tested for proliferative activity in C433 cells (FIG. 34). This active protein, eluting at 31% acetonitrile (700 ng total protein by measuring absorbance at 214 nm) is applied to a pulse liquid microsequencer, and the amino acid sequence of the first 28 amino acids is determined. This sequence is similar to, but not identical with, that of human, rat and mouse IGF-II. Another form of deer IGF-II has been cloned and the amino acid sequence encoded by the DNA is shown on Table 5. The sequences of these proteins are given below.

peptides of the present invention can be used to transform a host using any of the techniques commonly known to those of ordinary skill in the art.

A gene is a DNA sequence which encodes through its copy or messenger RNA a sequence of amino acids characteristic of a specific peptide. The term cDNA includes genes from which the intervening sequences have been removed.

Methods for preparing fused, operably linked genes and expressing them in bacteria are known and are shown, for example, in U.S. Pat. No. 4,366,246, herein

TABLE 5

| IGF-II | | | |
|---|---|---|---|
| DEER IGF-II, serum [SEQ ID NO: 6] | AYRPSETLXG | GELVDTLQFV | XGDXXFYF |
| DEER IGF-II, cloned [SEQ ID NO: 7] | AYRPSETLCG | GELVDTLQFV | CGDRGFYFSR |
| HUM IGF-II [SEQ ID NO: 8] | AYRPSETLCG | GELVDTLQFV | CGDRGFYFSR |
| MUS IGF-II [SEQ ID NO: 9] | AYGPGETLCG | GELVDTLQFV | CSDRGFYFSR |
| RAT IGF-II [SEQ ID NO: 10] | AYRPSETLCG | GELVDTLQFV | CSDRGFYFSR |
| DEER IGF-II, cloned | PSSRINRRSR | GIVEECCFRS | CDLALLETYC |
| HUM IGF-II | PASRVSRRSA | GIVEECCFRS | CDLALLETYC |
| MUS IGF-II | PSSRANRRSA | GIVEECCFRS | CDLALLETYC |
| RAT IGF-II | PSSRANRRSA | GIVEECCFRS | CDLALLETYC |
| DEER IGF-II, cloned | ATPAKSE | RDVS | |
| HUM IGF-II | ATPAKSE | | |
| MUS IGF-II | ATPAKSE | | |
| RAT IGF-II | ATPAKSE | | |

The present invention also relates to a nucleotide sequence encoding the biologically active polypeptides of the present invention. The DNA sequences which encode polypeptides of the present invention are described below:

incorporated by reference. The genetic constructs and methods described therein can be utilized for expression of the polypeptides of the present invention in prokaryotic or eukaryotic hosts. Hosts transformed with the nucleic acids encoding the polypeptides of the present

| ANTLERIN-1 (OT-1) | | | | | | | | | |
|---|---|---|---|---|---|---|---|---|---|
| [Amino acid SEQ ID NO: 1, Nucleic acid SEQ ID NO: 11] | | | | | | | | | |
| 1 | 2 | 3 | 4 | 5 | 6 | 7 | 8 | 9 | 10 |
| M | A | G | L | G | D | E | F | G | D |
| ATG | GCN | GGN | CTN TTR | GGN | GAY | GAR | TTY | GGN | GAY |

| OT-2 | | | | | | | | | |
|---|---|---|---|---|---|---|---|---|---|
| [Amino acid SEQ ID NO: 2, Nucleic acid SEQ ID NO: 12] | | | | | | | | | |
| 1 | 2 | 3 | 4 | 5 | 6 | 7 | 8 | 9 | 10 |
| (X) | F | E | T | L | F | G | A/V | E | D |
| (NNN) | TTY | GAR | ACN | CTN TTR | TTY | GGN | GYN | GAR | GAY |
| 11 | 12 | 13 | 14 | 15 | 16 | 17 | 18 | 19 | 20 |
| V | I/D | A | L | Q | F | V | C | G | D |
| GTN | GAY ATH | GCN | CTN TTR | CAR | TTY | GTN | TGY | GGN | GAY |

| OT-4 | | | | | | | | | |
|---|---|---|---|---|---|---|---|---|---|
| [Amino acid SEQ ID NO: 3, Nucleic acid SEQ ID NO: 13] | | | | | | | | | |
| 1 | 2 | 3 | 4 | 5 | 6 | 7 | 8 | 9 | 10 |
| A | Y | I | P | I | E | T | L | E | G |
| GCN | TAY | ATH | CCN | ATH | GAR | ACN | CTN TTR | GAR | GGN |
| 11 | 12 | 13 | 14 | 15 | 16 | 17 | 18 | 19 | |
| I/G | E | L | V | D/Q | T | G/L | Q | F | |
| ATH GGN | GAR | CTN TTR | GTN | GAY CAR | ACN | GGN CTN TTR | CAR | TTY | | wherein Y is selected from T or C, R is selected from A or G, H is selected from A, T or C, and N is selected from G, A, T or C and G, A, T and C represent guanine, adenine, thymidine, and cytosine. The biologically active polypeptides of the present invention may also be prepared utilizing recombinant DNA technology. A recombinant DNA molecule coding for any of the polypeptides invention are particularly useful for the production of polypeptides of the present invention The invention extends to any host modified according to the methods of ordinary skill in the art, such as, for example, by transfer of genetic material using an expression plasmid or lysogenic phage, and which yields a prokaryote or eukaryote expressing the gene for any of the antler-derived bone growth factors of the present invention.

Especially preferred is the use of a vector containing coding sequence for the polypeptides of the present invention for purposes of prokaryote transformation.

The term "host" as used herein is meant to include not only prokaryotes but also eukaryotes such as yeast as well as plant and animal cells. The term "prokaryote" is meant to include all bacteria which can be transformed with the DNA for the expression of the polypeptides of the present invention. Prokaryotic hosts may include Gram negative as well as Gram positive bacteria, such as *E. coli, S. typhimudum, Serratia marcescens,* and *Bacillus subtilis*. In addition to prokaryotes, eukaryotic microbes, such as cultures, may also be used. The term "eukaryote" is meant to include all yeasts, fungi, animal and plant cells which can be transformed with the DNA for the expression of the polypeptides of the present invention. Eukaryotic hosts may include yeasts such as *Pichia pastoris* or mammalian cells. *Saccharomyces cerevisiae,* or common baker's yeast, is the most commonly used among eukaryotic microorganisms, although a number of other strains and organisms are commonly available. Yeast promoters suitable for the expression of foreign DNA sequences in yeast include the promoters for 3-phosphoglycerate kinase or other glycolytic enzymes. Suitable expression vectors may also contain termination signals which provide for the polyadenylation and termination of the mRNA transcript of the cloned gene. Any vector containing a yeast-compatible promoter, origin of replication, and appropriate termination sequence is suitable for expression of the polypeptides of the present invention.

A cloning vehicle is a plasmid or phage DNA or other DNA sequence which is able to replicate in a host cell which is characterized by one or a small number of endonuclease recognition sites at which such DNA sequences may be cut in a determinable fashion without loss of an essential biological function of the DNA, and which contains a marker suitable for use in the identification of transformed cells. Markers, for example, are tetracycline resistance, neomycin resistance, or ampicillin resistance. The word "vector" is sometimes used for cloning vehicle.

An expression vehicle is a vehicle similar to a cloning vehicle but which is capable of expressing a given structural gene in a host, normally under control of certain control sequences. "Expression vectors" refer to vectors which are capable of transcribing a DNA sequences contained therein, where such sequences are linked to other regulatory sequences capable of affecting their expression.

The expression vector typically contains an origin of replication, promoter(s), terminator(s), a ribosome binding site, as well as specific genes which are capable of providing phenotypic selection in transformed cells. These expression vectors must be replicable in the host organisms or systems either as episomes, bactedophage, or as an integral part of the chromosomal DNA. The transformed hosts can be fermented and cultured according to means known in the art to achieve optimal cell growth.

Examples of promoters which can be used in the invention include, but are not limited to: rec A, trp, lac, tac, bacteriophage lambda pR or pL, MMTV, SV40. Examples of some of the plasmids or bacteriophages which can be used in the invention are listed in Maniatis et al., *Molecular Cloning,* Cold Spring Harbor Laboratories, 1982, and others are known to those of skill in the art and can be easily ascertained.

Recombinant vectors and methodology disclosed herein are suitable for use in host cells covering a wide range of prokaryotic and eukaryotic organisms. Prokaryotic cells are preferred for the cloning of DNA sequences and in the construction of vectors. For example, *E. coli* K12 strain HB101 (ATCC no. 33694), is particularly useful. Of course, other microbial strains may also be used.

Cell lines derived from multicellular organisms may also be used as hosts. In principle, any such cell culture is workable, whether from a vertebrate or invertebrate source. However, interest has been greatest in vertebrate cells, and propagation of vertebrate cells in culture (tissue culture) has become a routine procedure in recent years. Examples of such useful hosts are the VERO, HeLa, mouse C127, Chinese hamster ovary (CHO), WI38, BHK, COS-7, and MDCK cell lines. Expression vectors for such cells ordinarily include an origin of replication, a promoter located in front of the gene to be expressed, RNA splice sites (if necessary), and transcriptional termination sequences.

For use in mammalian cells, the control functions (promoters and enhancers) on the expression vectors are often provided by viral material. For example, commonly used promoters are derived from polyoma, Adenovirus 2, and most frequently, Simian Virus 40 (SV40). Eukaryotic promoters, such as the promoter of the murine metallothionein gene [Paulakis and Hamer, *Proc. Natl. Acad. Sci.* 80:397–401 (1983)], may also be used. Further, it is also possible, and often desirable, to utilize the promoter or control sequences which are naturally associated with desired gene sequence, provided such control sequences are compatible with the host system. To increase the rate of transcription, eukaryotic enhancer sequences can be obtained from a variety of animal cells or oncogenic retroviruses such as the murine sarcoma virus.

An origin of replication may be provided either by construction of the vector to include an exogenous origin, such as that provided by SV40 or other viral sources, or may be provided by the host cell chromosomal replication mechanism. If the vector is integrated into the host cell chromosome, the latter is often sufficient.

Host cells can synthesize the polypeptides of the present invention which can be of a variety of chemical compositions. The polypeptide may be produced having methionine as its first amino acid. This methionine is present by virtue of the ATG start codon naturally existing at the origin of the structural gene or by being engineered before a segment of the structural gene. The protein may also be intracellularly or extracellularly cleaved, giving rise to the amino acid which is found naturally at the amino terminus of the polypeptide. The polypeptide may be produced together with either its own or a heterologous signal peptide, the signal polypeptide being specifically cleavable in an intra- or extracellular environment. Finally, the polypeptides of the present invention may be produced by direct expression in mature form without the necessity of cleaving away any extraneous polypeptide.

Recombinant host cells refer to cells which have been transformed with vectors constructed using recombinant DNA techniques. As defined herein, the polypeptides of the present invention are produced as a consequence of this transformation. The polypeptides of the present invention or fragments thereof produced by such cells are referred to as "recombinant polypeptides of the present invention."

Several groups of workers have isolated mixtures of messenger RNA (mRNA) from eukaryotic cells and employed a series of enzymatic reactions to synthesize double-stranded DNA copies which are complementary to this mRNA mixture. In the first reaction, mRNA is transcribed into a single-stranded complementary DNA by an RNA-directed DNA polymerase, also called reverse transcriptase. Reverse transcriptase synthesizes DNA in the 5'-3' direction, utilizes deoxyribonucleoside 5'-triphosphates as precursors, and requires both a template and a primer strand, the latter of which must have a free 3'-hydroxyl terminus. Reverse transcriptase products, whether partial or complete copies of the mRNA template, often possess short, partially double-stranded hairpins ("loops") at their 3' termini. In the second reaction, these "hairpin loops" can be exploited as primers for DNA polymerases. Preformed DNA is required both as a template and as a primer in the action of DNA polymerase. The DNA polymerase requires the presence of a DNA strand having a free 3'-hydroxyl group, to which new nucleotides are added to extend the chain in the 5'-3' direction. The products of such sequential reverse transcriptase and DNA polymerase reactions still possess a loop at one end. The apex of the loop or "fold-point" of the double-stranded DNA, which has thus been created, is substantially a single-strand segment. In the third reaction, this single-strand segment is cleaved with the single-strand specific nuclease S1 to generate a "blunt-end" duplex DNA segment. This general method is applicable to any mRNA mixture, and is described by Buell, et al., *J. Biol. Chem.*, 253:2483 (1978).

The resulting double-stranded cDNA mixture (ds-cDNA) is inserted into cloning vehicles by any one of many known techniques, depending at least in part on the particular vehicle used. In general, methods can be found in Maniatis, et al., supra, and *Methods In Enzymology*, Volumes 65 and 68 (1980); and 100 and 101 (1983). In general, the vector is linearized by at least one restriction endonuclease, which will produce at least two blunt or cohesive ends. The ds-cDNA is ligated with or joined into the vector insertion site.

Once the DNA segments are inserted, the cloning vehicle is used to transform a suitable host. These cloning vehicles usually impart an antibiotic resistance trait on the host. Such hosts are generally prokaryotic cells.

If prokaryotic cells or other cells which contain substantial cell wall material are employed, the most common method for transformation with the expression vector is calcium chloride pretreatment as described by Cohen, R. N., et al., *Proc. Nat'l. Acad. Sci. USA*, 69:2110 (1972). If cells without cell wall barriers are used as host cells, transfection is carded out by the calcium phosphate precipitation method described by Graham and Van der Eb, *Virology*, 52:456 (1973). Other methods for introducing DNA into cells such as electroporation, nuclear injection, viral infection or protoplast fusion may be successfully used. At this point, only a few of the transformed or transfected hosts contain the desired cDNA. The sum of all transformed or transfected hosts constitutes a "gene library". The overall ds-cDNA library created by this method provides a representative sample of the coding information present in the mRNA mixture used as the starting material.

Clones containing part or the entire cDNA encoding the polypeptides of the present invention are identified with specific oligonucleotide probes deduced from a partial amino acid sequence of the polypeptides of the present invention. This method of identification requires that the oligonucleotide probe be designed such that it specifically hybridizes to the cDNA of the present invention. Clones containing cDNA sequences encoding the polypeptides of the present invention are isolated as follows.

Individual transformed or transfected cells are grown as colonies on or transferred to a membrane such as, for example, a nitrocellulose filter. These colonies are lysed; the DNA released is bound tightly to the membrane by heating. The filter paper is then incubated with a labeled oligonucleotide probe which is complementary to the structural gene of interest. The probe hybridizes with the cDNA for which it is complementary, and is identified by autoradiography. The corresponding clones are characterized in order to identify one or a combination of clones which contain all of the structural information for the desired protein.

Clones containing additional sequences may also be identified using as a probe the cDNA insert isolated during the initial screening of the cDNA library. Nucleotide sequencing techniques are used to deduce the sequence of amino acids encoded by the cDNA fragments.

The nucleic acid sequence coding for the protein of interest is isolated and reinserted into an expression vector. The expression vector brings the cloned gene under the regulatory control of specific prokaryotic or eukaryotic control elements which allow the efficient expression (transcription and translation) of the ds-cDNA. Thus, this general technique is only applicable to those proteins for which at least a portion of their amino acid or DNA sequence is known and for which an oligonucleotide probe is available. See, generally, Maniatis, et al., supra.

More recently, methods have been developed to identify specific clones by probing bacterial colonies or phage plaques with antibodies specific for the encoded protein of interest. This method can only be used with "expression vector" cloning vehicles since elaboration of the protein product is required. The structural gene is inserted into the vector adjacent to regulatory gene sequences that control expression of of the protein. The cells are lysed, either by chemical methods or by a function supplied by the host cell or vector, and the protein is detected by a specific antibody and a detection system such as enzyme immunoassay. An example of this is the lambda gt 11 system described by Young and Davis, *Proc. Nat'l. Acad. Sci. USA*, 80:1194–1198 (1983) and Young and Davis, *Science*, 222:778 (1983).

By providing the DNA sequences, and recombinant DNA molecules, the present invention also provides probes and methods to identify cells containing or lacking these sequences, and means to administer these sequences to cells. This will enable the establishment of systems in which the recombinant protein is produced after transfection of an expression vector into appropriate host cells. Additionally, the present invention provides a means to inhibit the expression of the novel sequences by providing an antisense RNA sequence which, when administered to a cell, or when the DNA encoding said antisense RNA is administered to a cell, said DNA sequence will produce an antisense RNA which can bind to and therefore block the expression of the RNA encoding the novel polypeptides of the present invention.

EXAMPLE 16

A. cDNA Cloning of Deer Antler IGF-like Growth Factors

A cDNA library is prepared from fresh-frozen, rapidly growing deer antler tips by a modification [Ray and Ray (1991) *Nucl. Acids Res.* 19: 4559] of the method of Gubler and Hoffman as described in (1983) *Gene* 25: 263-269. Deer antler tips are stored at −80° C. then homogenized with a Tekmar tissue homogenizer in RNAzol B (Tel-Test, Inc.). RNAzol [Chomczynski and Sacchi, (1987) *Anal. Biochem.* 162: 156-159] is a mixture of guanidine isothiocyanate and phenol that fosters the formation of complexes between guanidium salts and RNA, destroys hydrophilic interactions between nucleic acids and proteins and facilitates the separation of RNA from other cellular constituents. The RNAzol (20 ml/g of tissue) is used to extract total RNA from the antler tips after 0.1 volume of chloroform has been added; DNA and proteins extract into the organic phase and interface whereas RNA remains in the aqueous phase relatively free from contaminants. The aqueous phase (~½ of the original volume) is precipitated with an equal volume of 2-propanol, pelleted by centrifugation and the RNA pellet is washed in 75% ethanol, dried and resuspended in sterile water. The RNA is further purified by extraction with an equal volume of phenol:chloroform (1:1; v/v) and reprecipitated with 0.2M NaCl and 2.5 volumes of ethanol. The total RNA preparation is further enriched for messenger RNA by selecting for the 3' polyA tract found on most messenger RNAs using an affinity column packed with oligo(dT) cellulose [Maniatis, et al., ed. (1982) in Molecular Cloning: A Laboratory Manual]. Complementary DNAs are prepared from deer antler tip polyA(+) RNA by synthesizing first-strand cDNA using the catalytic activity of AMV reverse transcriptase and oligo(dT) as primer (~0.1 g of resin/mg total RNA). The product of this reaction is used to synthesize a second strand of cDNA using the specific RNA/DNA hybrid activity of RNase H (0.3 units/ml) to generate primers and using the polymerizing activity of *E. coli* DNA polymerase. The newly synthesized population of double-stranded cDNA molecules is an accurate representation of the messenger RNA molecules found in rapidly growing deer antler tips. The cDNA molecules (~2.0 ug) are repaired at their termini using T4 DNA polymerase and ligated to hemi-phosphorylated, double-stranded EcoRI-NotI adaptor oligonucleotides (100-fold molar excess) that are blunt-ended and phosphorylated at the NotI end and have a protruding, unphosphorylated 5' overhang at the EcoRI end. The ligated material was then size-fractionated on a 0.8% agarose gel and cDNA molecules >1 kb in size are purified by electroelution and ethanol precipitation as described in Maniatis. The material is then phosphorylated using T4 polynucleotide kinase as described in Maniatis. The purified cDNA (~150 ng) is ligated into the EcoRI site of the cloning vector lambda ZAPII (Stratagene) using a molar ratio of ~1:3 (insert to vector). The library of recombinant lambda phage (~1.5 million independent clones) are packaged, plated and amplified in 14 separate fractions using the *E. coli* host strain XL-1 Blue as described in Maniatis. Each separate fraction contained between 40,000 and 150,000 clones. After determining that >80% of randomly chosen, rescued clones contained recombinant inserts and that the test inserts ranged in size from <1 kb to >7 kb, the bulk of the library is pooled; small aliquots of the separate amplified fractions are saved for experiments where analytical techniques can facilitate focusing on one fraction or another.

B. Polymerase Chain Reaction (PCR) Detection of IGF-like cDNA Clones

The deer antler tip cDNA library fractions are screened by polymerase chain reaction (PCR) (Saiki, et al. (1988) *Science* 239: 487-491) for detection of deer IGF-I and IGF-II sequences. Since deer IGFs have not previously been cloned, the oligonucleotides used for amplifying IGF sequences are designed from IGF-I and IGF-II regions highly conserved among different species. Specific IGF-I and IGF-II reactions are carried out separately. The IGF-I reactions utilize a sense-strand IGF-I specific oligonucleotide (with the sequence 5'-CTGGATCCAGAGACCCTCTGCGGGGC-3', [SEQ ID NO: 14]) and a downstream anti-sense primer (with the sequence 5'-CTGCGGAATTCAGCACTCATCCACGAT-3', [SEQ ID NO: 15]) that should prime both IGF-I and IGF-II sequences. The IGF-II reactions utilize a sense-strand IGF-II-specific primer (with the sequence 5'-ATGGGGATCCCAGTGGGGAAGTCGAT-3', [SEQ ID NO: 16]) and the same general downstream anti-sense IGF primer used for the IGF-I reactions. The sense primers has an engineered BamHI site and the anti-sense primer had an engineered EcoRI site for ease in subcloning. Electrophoresed, amplified DNA products of the expected size (~150 bp) are obtained from IGF-I reactions from several of the library fractions. A single reaction, fraction 11, produces an IGF-II-specific product (~200 bp). The IGF-I and IGF-II PCR products are specifically probed with a radiolabelled internal IGF-specific oligonucleotide (with the sequence 5'-CTCTTCAGTTCGTCTGTGGAGACAGCGGCTT-3', [SEQ ID NO: 17]). All PCR experiments contain a single internal positive control using a human IGF-I plasmid as template; this control has the potential for contaminating other reactions and obscuring the IGF-I, but not the IGF-II, results.

C. Partial Nucleotide Sequence of PCR-amplified Deer Antler IGF-I-like DNA

A specific PCR product for IGF-I is amplified from several deer antler tip cDNA library fractions. The ~150 bp product from fraction 3 of the cDNA library prepared in Example 16A is digested with BamHI and EcoRI and subcloned into M13 mp18 for propagation and sequence analysis. The insert is sequenced using dideoxy chain termination [Sanger, et al. (1977) *Proc. Natl. Acad. Sci. USA* 74: 5463-5467] and the nucleotide sequence through this short, relatively conserved amplified region of deer IGF differs from human IGF-I by a single nucleotide. The deduced amino acid sequence of the deer IGF-I PCR-amplified clone is identical in this short region to human IGF-I (see Example 13).

D. Cloning of a cDNA for Deer IGF-II

Fraction 11 of the deer antler tip cDNA library is screened for the cDNA clone detected in the PCR analysis. The IGF-II specific sense strand oligonucleotide used for PCR experiments is radiolabelled and used to screen ~300,000 amplified phage plaques from fraction 11. A single hybridizing clone is detected, purified with one round of plaque purification and rescued into pBluescript plasmid vector. The insert from this plasmid (pdIGFII) is subcloned into the EcoRl site of M13 mp18. Preliminary nucleotide sequence at the 5' and 3' termini of the clone indicates that deer IGF-II is highly similar, but not identical, to IGF-II in humans, sheep and cattle in its 5' and 3' untranslated regions. Preliminary nucleotide sequence analysis through a portion of the coding region also reveals that deer IGF-II is highly similar, yet distinct, from IGF-II in other species and the deduced amino acid sequence of deer IGF-II is also highly similar, but not identical, to the amino acid sequence of IGF-II from certain other species. The comparison of the partial cDNA sequences and deduced amino acid sequences of deer IGF-II versus human IGF-II is presented in Table 6.

C.F.R. §1.14 and 35 U.S.C. §122, or if and when such access is required by the Budapest Treaty. All restriction on availability of said cultures to the public will be irrevocably removed upon the granting of a patent based upon the application and said cultures will remain permanently available for a term of at least five years after the most recent request for the furnishing of samples and in any case for a period of at least 30 years after the date of the deposits. Should the cultures become nonviable or be inadvertently destroyed, they will be replaced with viable cultures(s) of the same taxonomic description.

| Strain/Plasmid | ATCC No. | Deposit Date |
|---|---|---|
| pdIGF-II | | |
| MAbOT-2 | | |

One skilled in the art will readily appreciate the pres-

TABLE 6

| Comparison of cDNA and Amino Acid Sequences of Deer and Human IGF-II | | | | | | | | | | |
|---|---|---|---|---|---|---|---|---|---|---|
| Deer | A | Y | R | P | S | E | T | L | C | G | G |
| IGFII | GCT | TAC | CGC | CCC | AGT | GAG | ACC | tTG | TGC | GGC | GGG |
| [Amino acid SEQ ID NO: 18, Nucleic acid SEQ ID NO: 19] | | | | | | | | | | |
| Human | GCT | TAC | CGC | CCC | AGT | GAG | ACC | cTG | TGC | GGC | GGG |
| IGFII | A | Y | R | P | S | E | T | L | C | G | G |
| [Amino acid SEQ ID NO: 21, Nucleic acid SEQ ID NO: 20] | | | | | | | | | | |
| Deer | E | L | V | D | T | L | Q | F | V | C | G |
| IGFII | GAG | CTG | GTG | GAC | ACC | CTC | CAG | TTt | GTC | TGT | GGG |
| HIGFII | GAG | CTG | GTG | GAC | ACC | CTC | CAG | TTc | GTC | TGT | GGG |
|  | E | L | V | D | T | L | Q | F | V | C | G |
| Deer | D | R | G | F | Y | F | S | R | P | S | S |
| IGFII | GAC | CGC | GGC | TTC | TAC | TTC | AGC | cGa | CCa | tCc | AGC |
| HIGFII | GAC | CGC | GGC | TTC | TAC | TTC | AGC | aGg | CCc | gCa | AGC |
|  | D | R | G | F | Y | F | S | R | P | A | S |

Deposit of Strains Useful in Practicing the Invention

Deposits of biologically pure cultures of the following strains will be made under the Budapest Treaty with the American Type Culture Collection, 12301 Parklawn Drive, Rockville, Md. The accession numbers indicated were assigned after successful viability testing, and the requisite fees were paid.

Access to said cultures will be available during pendency of the patent application to one determined by the Commissioner of the United States Patent and Trademark Office to be entitled thereto under 37 ent invention is well adapted to carry out the objects and obtain the ends and advantages mentioned, as well as those inherent therein. The peptides, antibodies, methods, procedures and techniques described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

What is claimed as new and intended to be covered by letters patent of the United States is:

1. A process for purifying a proteinaceous material comprising the amino acid sequence M-A-G-L-G-D-E-F-G-D (SEQ ID NO: 1), said proteinaceous material possessing the biological activity of stimulating thymidine incorporation in osteoblast-like cells, said process comprising:

a. applying an antler tissue EDTA extract to heparin Sepharose CL-6B and eluting with a linear gradient of 0.1–3.0M NaCl;

b. applying the eluted material of step (a) with said biological activity to Sephacryl S-100 and eluting;

c. applying the eluted material of step (b) with said biological activity to a reverse phase HPLC C18 column and eluting using a gradient of 0.1% TFA and 0.1% TFA/70% acetonitrile at a flow rate of 2 ml/minute;
d. applying the eluted material of step (c) with said biological activity to a reverse phase HPLC C8 column and eluting using a gradient of 0.1% TFA and 0.1% TFA/70% acetonitrile at a flow rate of 0.15 ml/minute; and
e. collecting the eluted material of step (d) with said biological activity.

2. A process for purifying a proteinaceous material comprising the amino acid sequence (X) F-E-T-L-F-G-A/V-E-D-V-I/D-A-L (SEQ ID NO: 2), said proteinaceous material possessing the biological activity of stimulating thymidine incorporation in osteoblast-like cells, said process comprising:
   a. applying an antler tissue EDTA extract to heparin Sepharose CL-6B and eluting with a linear gradient of 0.1–3.0M NaCl;
   b. applying the eluted material of step (a) with said biological activity to Sephacryl S-100 and eluting with 500 mM NH₄HCO₃;
   c. applying the eluted material of step (b) with said biological activity to a reverse phase HPLC C18 column and eluting using a gradient of 0.1% TFA and 0.1% TFA/70% acetonitrile at a flow rate of 2 ml/minute;
   d. applying the eluted material of step (c) with said biological activity to a reverse phase HPLC C4 column and eluting using a gradient of 0.1% TFA and 0.1% TFA/70% acetonitrile at a flow rate of 0.15 ml/minute;
   e. applying the eluted material of step (d) with said biological activity to a reverse phase HPLC C8 column and eluting using a gradient of 0.1% TFA and 0.1% TFA/70% acetonitrile at a flow rate of 0.15 ml/minute; and
   f. collecting the eluted material of step (e) with said biological activity.

3. A process for purifying a proteinaceous material comprising the amino acid sequence A-Y-I-P-E-T-L-E-G-I/G-E-L-V-D/Q-T-G/L-Q-F (SEQ ID NO: 3), said proteinaceous material possessing the biological activity of stimulating thymidine incorporation in osteoblast-like cells, said process comprising:
   a. applying a cultured deer antler cell conditioned medium to heparin Sepharose CL-6B and eluting with 3.0M NaCl followed by 4M NaCl Tris buffer;
   b. applying the eluted material of step (a) with said biological activity to Sephacryl S-100 and eluting;
   c. applying the eluted material of step (b) with said biological activity to a Sephadex C50 column and eluting with a linear gradient from 1M acetic acid 0.075M NaCl pH 3.0 to 1M ammonium acetate 1.5M NaCl pH 9.0;
   d. applying the eluted material of step (c) with said biological activity to an amino link agarose column carrying IGF-BP₃ and eluting with 1M acetic acid;
   e. applying the eluted material of step (d) with said biological activity to a reverse phase HPLC C4 column and eluting with 0.1% TFA and a gradient of 7–35% acetonitrile at a flow rate of 0.15 ml/minute; and
   f. collecting the eluted material of step (e) with said biological activity.

* * * * *